United States Patent
Kretschmer et al.

(10) Patent No.: US 11,206,831 B2
(45) Date of Patent: Dec. 28, 2021

(54) SUBSTITUTED OXADIAZOLES FOR COMBATING PHYTOPATHOGENIC FUNGI

(71) Applicant: BASF SE, Ludwigshafen (DE)

(72) Inventors: Manuel Kretschmer, Washington, DC (US); Wassilios Grammenos, Ludwigshafen (DE); Christine Wiebe, Ludwigshafen (DE); Ian Robert Craig, Ludwigshafen (DE); Ana Escribano Cuesta, Ludwigshafen (DE); Violeta Terteryan-Seiser, Ludwigshafen (DE); Marcus Fehr, Ludwigshafen (DE); Tobias Mentzel, Limburgerhof (DE); Maria Angelica Quintero Palomar, Limburgerhof (DE); Thomas Grote, Ludwigshafen (DE); Erica Cambeis, Ludwigshafen (DE); Bernd Mueller, Ludwigshafen (DE); Christian Harald Winter, Mumbai (IN); Jan Klaas Lohmann, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 835 days.

(21) Appl. No.: 15/780,994

(22) PCT Filed: Nov. 16, 2016

(86) PCT No.: PCT/EP2016/077821
§ 371 (c)(1),
(2) Date: Jun. 1, 2018

(87) PCT Pub. No.: WO2017/093019
PCT Pub. Date: Jun. 8, 2017

(65) Prior Publication Data
US 2020/0281204 A1   Sep. 10, 2020

(30) Foreign Application Priority Data
Dec. 3, 2015 (EP) ..................... 15197814

(51) Int. Cl.
*A01N 43/82* (2006.01)
*C07D 271/06* (2006.01)

(52) U.S. Cl.
CPC .......... *A01N 43/82* (2013.01); *C07D 271/06* (2013.01)

(58) Field of Classification Search
CPC .............. A01N 43/82; C07D 271/06
See application file for complete search history.

(56) References Cited

U.S. PATENT DOCUMENTS 4,871,753 A   10/1989 Rohr
8,481,576 B2   7/2013 Netz et al.

FOREIGN PATENT DOCUMENTS

| EP | 0276432 A2 | 8/1988 |
|---|---|---|
| KR | 20140048235 A | 4/2014 |
| WO | 9730047 A1 | 8/1997 |
| WO | WO-2011/088181 A1 | 7/2011 |
| WO | WO-2013/008162 A1 | 1/2013 |
| WO | 13064079 A1 | 5/2013 |
| WO | 13080120 A1 | 6/2013 |
| WO | WO-2014/128136 A1 | 8/2014 |
| WO | 15185485 A1 | 12/2015 |
| WO | 17076739 A1 | 5/2017 |
| WO | 17076740 A1 | 5/2017 |
| WO | 17076742 A1 | 5/2017 |
| WO | 17076757 A1 | 5/2017 |
| WO | 17076935 A1 | 5/2017 |
| WO | 17081309 A1 | 5/2017 |
| WO | 17081310 A1 | 5/2017 |
| WO | 17081311 A1 | 5/2017 |
| WO | 17081312 A1 | 5/2017 |
| WO | 17085098 A1 | 5/2017 |
| WO | 17085100 A1 | 5/2017 |

(Continued)

OTHER PUBLICATIONS

International Search Report, issued in PCT/EP2016/077821, dated Dec. 21, 2016.

(Continued)

*Primary Examiner* — Yong L Chu
(74) *Attorney, Agent, or Firm* — Marshall, Gerstein & Borun LLP

(57) ABSTRACT

The present invention relates to novel oxadiazoles of formula I, or the N-oxides and/or their agriculturally useful salts and to their use for controlling phytopathogenic fungi, or to a method for combating phytopathogenic harmful fungi, which process comprises treating the fungi or the materials, plants, the soil or seeds to be protected against fungal attack, with an effective amount of at least one compound of formula I, or an N-oxide, or an agriculturally acceptable salt thereof; the present invention also relates to mixtures comprising at least one such compound of formula I and at least one further pesticidally active substance selected from the group consisting of herbicides, safeners, fungicides, insecticides, and plant growth regulators; and to agrochemical compositions comprising at least one such compound of formula I and to agrochemical compositions further comprising seeds.

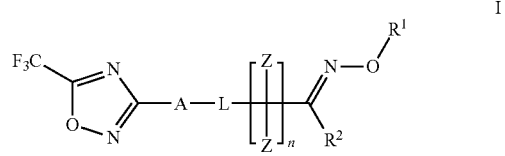

23 Claims, No Drawings

(56) References Cited

FOREIGN PATENT DOCUMENTS

| WO | 17093019 A1 | 6/2017 |
|---|---|---|
| WO | 17148797 A1 | 9/2017 |
| WO | 17178245 A1 | 10/2017 |
| WO | 17211649 A1 | 12/2017 |
| WO | 17211650 A1 | 12/2017 |
| WO | 17211652 A1 | 12/2017 |

OTHER PUBLICATIONS

International Preliminary Report on Patentability, issued in PCT/EP2016/077821, dated Jun. 5, 2018.
Search Report, issued in EP Application No. 15197814.5, dated Feb. 25, 2016.
Tale et al., "Syntehsis and Anti-Bacterial, Anti-Fungal Activity of Novel 1,2,4-Oxadiazole," Journal of Chemical and Pharmaceutical Research, vol. 3, Issue 2, (2011), pp. 496-505.

SUBSTITUTED OXADIAZOLES FOR COMBATING PHYTOPATHOGENIC FUNGI

This application is a National Stage application of International Application No. PCT/EP2016/077821, filed Nov. 16, 2016. This application also claims priority under 35 U.S.C. § 119 to European Patent Application No. 15197814.5, filed Dec. 3, 2015.

The present invention relates to novel oxadiazoles of formula I, or the N-oxides and/or their agriculturally useful salts and to their use for controlling phytopathogenic fungi, or to a method for combating phytopathogenic harmful fungi, which process comprises treating the fungi or the materials, plants, the soil or seeds to be protected against fungal attack, with an effective amount of at least one compound of formula I, or an N-oxide, or an agriculturally acceptable salt thereof; the present invention also relates to mixtures comprising at least one such compound of formula I and at least one further pesticidally active substance selected from the group consisting of herbicides, safeners, fungicides, insecticides, and plant growth regulators; and to agrochemical compositions comprising at least one such compound of formula I and to agrochemical compositions further comprising seeds.

EP 276432 A2 relates to 3-phenyl-5-trifluoromethyloxadiazole derivatives and to their use to combat phytopathogenic microorganisms. WO 2013/080120 relates to other trifluoromethyloxadiazole derivatives and their use as pharmaceuticals, particular for the treatment of neurodegeneration, muscle atrophy or diabetes/metabolic syndrome. WO 2015/185485 was published after the date of filing of the present application and describes the use of certain substituted oxadiazoles for combating phytopathogenic fungi.

In many cases, in particular at low application rates, the fungicidal activity of known fungicidal compounds is unsatisfactory. Based on this, it was an objective of the present invention to provide compounds having improved activity and/or a broader activity spectrum against phytopathogenic fungi. This objective is achieved by the oxadiazoles of formula I and/or their agriculturally useful salts for controlling phytopathogenic fungi.

The compounds according to the invention differ from those described in EP 276432 A2 or WO 2015/185485 in the nature of the radical

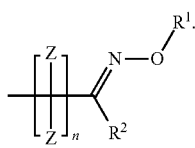

Likewise, the compounds according to the invention differ from those described in WO 2013/080120 in the nature of the oxime group $C(=NOR^1)R^2$.

Accordingly, the present invention relates to compounds of formula I, or the N-oxides, or the agriculturally acceptable salts thereof

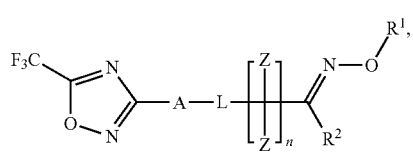

I wherein:
A is a phenyl ring or a 5- or 6-membered aromatic heterocycle, wherein the ring member atoms of the aromatic heterocycle include besides carbon atoms 1, 2, 3 or 4 heteroatoms selected from N, O and S as ring member atoms; and wherein the phenyl ring or the aromatic heterocycle is unsubstituted or substituted by 1, 2, 3 or 4 identical or different groups $R^A$; wherein
$R^A$ is halogen, cyano, $diC_1$-$C_6$-alkylamino, $C_1$-$C_6$-alkyl, $C_1$-$C_6$-alkoxy, $C_1$-$C_6$-alkyl-thio, $C_1$-$C_6$-alkylsulfinyl, $C_1$-$C_6$-alkylsulfonyl, $C_2$-$C_{O6}$-alkenyl, $C_2$-$C_6$-alkynyl, $C_3$-$C_8$-cycloalkyl or $C_3$-$C_8$-cycloalkoxy; and wherein any of the aliphatic or cyclic moieties are unsubstituted or substituted by 1, 2, 3, 4 or up to the maximum possible number of identical or different groups $R^a$; wherein
$R^a$ is halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_4$-alkoxy-$C_1$-$C_4$-alkyl or $C_3$-$C_8$-cycloalkyl;
L is #-C(=X)-NR- or #-NR-C(=X)-, wherein # denotes the position to which the cyclic group A is attached to; and wherein
X is O or S; and
R is hydrogen, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkenyl, C(=O)-($C_1$-$C_6$-alkyl), C(=O)-($C_1$-$C_6$-alkoxy), phenyl-$C_1$-$C_4$-alkyl, heteroaryl-$C_1$-$C_4$-alkyl, phenyl, naphthyl or a 3- to 10-membered saturated, partially unsaturated or aromatic mono- or bicyclic heterocycle; wherein the heteroaryl group in heteroaryl-$C_1$-$C_4$-alkyl is a 5- or 6-membered aromatic heterocycle, wherein the ring member atoms of said 5- or 6-membered aromatic heterocycle include besides carbon atoms 1, 2, 3 or 4 heteroatoms selected from N, O and S as ring member atoms; and wherein the ring member atoms of said 3- to 10-membered saturated, partially unsaturated or aromatic mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and
wherein any of the above-mentioned aliphatic or cyclic groups are unsubstituted or substituted by 1, 2, 3 or up to the maximum possible number of identical or different groups $R^{1a}$; wherein
$R^{1a}$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_4$-alkylamino, $diC_1$-$C_4$-alkylamino, $C_1$-$C_6$-alkylthio, $C_1$-$C_6$-haloalkylthio, $C_3$-$C_8$-cycloalkyl, $NHSO_2$-$C_1$-$C_4$-alkyl, (C=O)-$C_1$-$C_4$-alkyl, C(=O)-$C_1$-$C_4$-alkoxy, $C_1$-$C_6$-alkylsulfonyl, hydroxy$C_1$-$C_4$-alkyl, C(=O)-$NH_2$, C(=O)-NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, $diC_1$-$C_4$-alkylamino-$C_1$-$C_4$-alkyl, aminocarbonyl-$C_1$-$C_4$-alkyl or $C_1$-$C_4$-alkoxy-$C_1$-$C_4$-alkyl;
n is 0, 1, 2 or 3;
Z, which may be the same or different to any other Z, is hydrogen, halogen, $C_1$-$C_6$-alkyl, $C_1$-$C_6$-alkoxy, $C_1$-$C_6$-alkylthio, $C_2$-$C_6$-alkenyl, $C_2$-$C_6$-alkynyl, $C_3$-$C_8$-cycloalkyl, $C_3$-$C_8$-cyclo-alkenyl, phenyl-$C_1$-$C_4$-alkyl, heteroaryl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the aliphatic or cyclic groups are unsubstituted or substituted by 1, 2, 3, 4 or up to the maximum possible number of identical or different groups $R^{1a}$, or two radicals Z that are bound to the same carbon atom may form together with said carbon atom a $C_3$-$C_8$-cycloalkyl;

$R^1$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cyclo-alkenyl, phenyl, phenyl-$C_1$-$C_4$-alkyl, or a three- to ten-membered saturated, partially unsaturated or aromatic mono- or bicyclic heterocyclyl which, in addition to carbon atoms, contains one to four heteroatoms from the group consisting of O, N and S as ring members; and wherein any of the above-mentioned aliphatic or cyclic groups are unsubstituted or substituted by 1, 2, 3 or up to the maximum possible number of identical or different groups $R^{1a}$; and $R^2$ is hydrogen, halogen, cyano, amino, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, C(=O)—($C_1$-$C_6$-alkyl), C(=O)—($C_1$-$C_6$-alkoxy), $C_1$-$C_4$-alkylamino, di$C_1$-$C_4$-alkylamino, phenyl-$C_1$-$C_4$-alkyl, heteroaryl-$C_1$-$C_4$-alkyl, phenyl, naphthyl or a 3- to 10-membered saturated, partially unsaturated or aromatic mono- or bicyclic heterocycle; wherein the heteroaryl group in heteroaryl-$C_1$-$C_4$-alkyl is a 5- or 6-membered aromatic heterocycle, wherein the ring member atoms of said 5- or 6-membered aromatic heterocycle include besides carbon atoms 1, 2, 3 or 4 heteroatoms selected from N, O and S as ring member atoms; and wherein the ring member atoms of said 3- to 10-membered saturated, partially unsaturated or aromatic mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein any of the above-mentioned aliphatic or cyclic groups are unsubstituted or substituted by 1, 2, 3 or up to the maximum possible number of identical or different groups $R^{1a}$.

In respect of the variables, the embodiments of the intermediates obtained during preparation of compounds I correspond to the embodiments of the compounds of formula I. The term "compounds I" refers to compounds of formula I.

Agriculturally acceptable salts of the compounds I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of acceptable acid addition salts are primarily chloride, bromide, fluoride, hydrogen-sulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound I with an acid of the corresponding anion, preferably of hydrochloric acid, hydro-bromic acid, sulfuric acid, phosphoric acid or nitric acid.

Compounds I can exist as one or more stereoisomers. The various stereoisomers include enantiomers, diastereomers, atropisomers arising from restricted rotation about a single bond of asymmetric groups and geometric isomers. They also form part of the subject matter of the present invention. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, e.g. a racemate, individual stereoisomers, or as an optically active form.

Compounds I can be present in different crystal modifications whose biological activity may differ. They also form part of the subject matter of the present invention.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, for example methyl, ethyl, propyl, 1-methylethyl, butyl, 1-methyl-propyl, 2-methylpropyl, and 1,1-dimethylethyl.

The term "$C_1$-$C_6$-haloalkyl" refers to a straight-chained or branched alkyl group having 1 to 6 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl and chlorodifluoromethyl.

The term "$C_1$-$C_6$-alkoxy" refers to a straight-chain or branched alkyl group having 1 to 6 carbon atoms (as defined above) which is bonded via an oxygen, at any position in the alkyl group, for example methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy group as defined above, wherein some or all of the hydrogen atoms may be replaced by halogen atoms as mentioned above, for example, $OCH_2F$, $OCHF_2$, $OCF_3$, $OCH_2Cl$, $OCHCl_2$, $OCCl_3$ or OCHFCl.

The terms "phenyl-$C_1$-$C_4$-alkyl or heteroaryl-$C_1$-$C_4$-alkyl" refer to alkyl having 1 to 4 carbon atoms (as defined above), wherein one hydrogen atom of the alkyl radical is replaced by a phenyl or heteroaryl radical respectively.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_4$-alkylthio-$C_1$-$C_4$-alkyl" refers to alkyl having 1 to 4 carbon atoms (as defined above), wherein one hydrogen atom of the alkyl radical is replaced by a $C_1$-$C_4$-alkylthio group.

The term "$C_1$-$C_6$-alkylthio" as used herein refers to straight-chain or branched alkyl groups having 1 to 6 carbon atoms (as defined above) bonded via a sulfur atom. Accordingly, the term "$C_1$-$C_6$-haloalkylthio" as used herein refers to straight-chain or branched haloalkyl group having 1 to 6 carbon atoms (as defined above) bonded through a sulfur atom, at any position in the haloalkyl group.

The term "$C_1$-$C_6$-alkylsulfinyl" refers to straight-chain or branched alkyl groups having 1 to 6 carbon atoms (as defined above) bonded through a —S(=O)— moiety, at any position in the alkyl group, for example methylsulfinyl and ethylsulfinyl, and the like.

The term "$C_1$-$C_6$-alkylsulfonyl" refers to straight-chain or branched alkyl groups having 1 to 6 carbon atoms (as defined above), bonded through a —S(=O)$_2$— moiety, at any position in the alkyl group, for example methylsulfonyl.

The term "hydroxy$C_1$-$C_4$-alkyl" refers to alkyl having 1 to 4 carbon atoms, wherein one hydrogen atom of the alkyl radical is replaced by a OH group.

The term "amino$C_1$-$C_4$-alkyl" refers to alkyl having 1 to 4 carbon atoms, wherein one hydrogen atom of the alkyl radical is replaced by a $NH_2$ group.

The term "$C_1$-$C_4$-alkylamino" refers to refers to amino, wherein one hydrogen atom of the amino radical is replaced by a $C_1$-$C_4$-alkyl group. Likewise the term "di$C_1$-$C_4$-alkylamino" refers to refers to amino, wherein both hydrogen atoms are replaced by $C_1$-$C_4$-alkyl groups.

The term "$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a $C_1$-$C_4$-alkyl-NH— group which is bound through the nitrogen. Likewise the term "di$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a ($C_1$-$C_4$-alkyl)$_2$N-group which is bound through the nitrogen.

The term "aminocarbonyl-$C_1$-$C_4$-alkyl" refers to alkyl having 1 to 4 carbon atoms, wherein one hydrogen atom of the alkyl radical is replaced by a —(C=O)—$NH_2$ group.

The term "$C_2$-$C_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_3$-$C_8$-cycloalkyl" refers to monocyclic saturated hydrocarbon radicals having 3 to 8 carbon ring members such as cyclopropyl ($C_3H_5$), cyclobutyl, cyclopentyl, cyclohexyl, cycloheptyl or cyclooctyl.

The term "$C_3$-$C_8$-cycloalkyloxy" refers to a cycloalkyl radical having 3 to 8 carbon atoms (as defined above), which is bonded via an oxygen.

The term "C(=O)—$C_1$-$C_4$-alkyl" refers to a radical which is attached through the carbon atom of the C(=O) group as indicated by the number valence of the carbon atom.

The term "aliphatic" refers to compounds or radicals composed of carbon and hydrogen and which are non-aromatic compounds. An alicyclic compound or radical is an organic compound that is both aliphatic and cyclic. They contain one or more all-carbon rings which may be either saturated or unsaturated, but do not have aromatic character.

The terms "cyclic moiety" or "cyclic group" refer to a radical which is an alicyclic ring or an aromatic ring, such as, for example, phenyl or heteroaryl.

The term "and wherein any of the aliphatic or cyclic groups are unsubstituted or substituted by 1, 2, 3, 4 or up to the maximum possible number of identical or different groups $R^{1a}$" refers to aliphatic groups, cyclic groups and groups, which contain an aliphatic and a cyclic moiety in one group, such as in, for example, phenyl-$C_1$-$C_4$-alkyl; therefore a group which contains an aliphatic and a cyclic moiety both of these moieties may be substituted or unsubstituted independently of each other.

The term "heteroaryl" refers to aromatic monocyclic or polycyclic ring systems including besides carbon atoms, 1, 2, 3 or 4 heteroatoms independently selected from the group consisting of N, O and S.

The term "phenyl" refers to an aromatic ring systems including six carbon atoms (commonly referred to as benzene ring).

The term "5- or 6-membered heteroaryl" or the term "5- or 6-membered aromatic heterocycle" refer to aromatic ring systems including besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

In respect of the variables, the embodiments of the intermediates correspond to the embodiments of the compounds I. Preference is given to those compounds I and, where applicable, also to compounds of all sub-formulae provided herein, e. g. formulae I.A.1 to I.B.3.d, wherein variables such as A, $R^A$, $R^a$, L, X, n, Z, R, $R^1$, $R^2$ and $R^{1a}$ have independently of each other or more preferably in combination (any possible combination of 2 or more substituents as defined herein) the following meanings:

In one embodiment of the invention A is a phenyl ring which is unsubstituted or substituted by 1, 2, 3 or 4 identical or different groups $R^A$ as defined or preferably defined herein.

In another aspect of the invention A is a phenyl ring wherein the moiety L is attached to the phenyl ring in para-position with regard to the oxadiazole group (1,4-phenylene) and which is unsubstituted or substituted by 1, 2, 3 or 4 identical or different groups $R^A$ as defined or preferably defined herein.

In one aspect of the invention A is a phenyl ring wherein the moiety L is attached to the phenyl ring in meta-position with regard to the oxadiazole group (1,3-phenylene) and which is unsubstituted or substituted by 1, 2, 3 or 4 identical or different groups $R^A$ as defined or preferably defined herein.

In another embodiment A is a 6-membered aromatic heterocycle, wherein the ring member atoms of the heterocyclic ring include besides carbon atoms 1 or 2 nitrogen atoms as ring member atoms; and wherein A is unsubstituted or substituted by 1, 2 or 3 identical or different groups $R^A$ as defined or preferably defined herein.

In a further embodiment A is a 6-membered aromatic heterocycle, wherein the ring member atoms of the heterocyclic ring include besides carbon atoms 1 or 2 nitrogen atoms as ring member atoms; and wherein A is unsubstituted or substituted by 1, 2 or 3 identical or different groups $R^A$ as defined or preferably defined herein and wherein the moiety L is attached to the 6-membered aromatic heterocycle in para-position with regard to the oxadiazole group.

In another embodiment A is a 6-membered aromatic heterocycle, wherein the ring member atoms of the heterocyclic ring include besides carbon atoms 1 or 2 nitrogen atoms as ring member atoms; and wherein A is unsubstituted or substituted by 1, 2 or 3 identical or different groups $R^A$ as defined or preferably defined herein and wherein the moiety L is attached to the 6-membered aromatic heterocycle in meta-position with regard to the oxadiazole group.

In still another embodiment A is a pyridine ring which is unsubstituted or substituted by 1, 2 or 3 identical or different groups $R^A$ as defined or preferably defined herein and wherein the moiety L is attached to the pyridine ring in para-position with regard to the oxadiazole group.

In one further aspect A is a pyridine ring which is unsubstituted or substituted by 1, 2 or 3 identical or different groups $R^A$ as defined or preferably defined herein and wherein the moiety L is attached to the pyridine ring in meta-position with regard to the oxadiazole group.

In a further preferred embodiment A is a 5-membered aromatic heterocycle, wherein the ring member atoms of the heterocycle include besides carbon atoms 1, 2, 3 or 4 heteroatoms selected from N, O and S as ring member atoms; and wherein A is unsubstituted or substituted by 1, 2, 3 or 4 identical or different groups $R^A$ as defined or preferably defined herein.

In a further embodiment A is a thiophene, pyrazole, oxazole, isoxazole, thiazole or isothiazole ring; and wherein A is unsubstituted or substituted by 1, 2, 3 or 4 identical or different groups $R^A$ as defined or preferably defined herein.

In still a further embodiment A is a thiophene, pyrazole, oxazole, isoxazole, thiazole or isothiazole ring; wherein the oxadiazole group and the moiety L are attached to the thiophene ring in 2,5-position or the oxadiazole group and the moiety L are attached to the pyrazole, isothiazole or isoxazole ring in 3,5-position or the oxadiazole group and the moiety L are attached to the thiazole or oxazole ring in 2,4- or 2,5-position; and wherein A is unsubstituted or substituted by 1, 2, 3 or 4 identical or different groups $R^A$ as defined or preferably defined herein.

In one embodiment A is a thiophene ring; wherein the oxadiazole ring and the moiety L are attached to the thiophene ring in either 2,5-; 3,5 or 5,3-position; and wherein the thiophene ring is unsubstituted or substituted by 1, 2, 3 or 4 identical or different groups $R^A$ as defined or preferably defined herein.

In a further embodiment A is a phenyl, thiophene or pyridine ring; and wherein A is unsubstituted or substituted by 1 or 2 identical or different groups $R^A$ as defined or preferably defined herein.

In a preferred embodiment of the invention $R^A$ is halogen, cyano, $C_1$-$C_6$-alkyl, $C_1$-$C_6$-alkoxy, $C_2$-$C_6$-alkenyl, $C_2$-$C_6$-alkynyl or $C_3$-$C_8$-cycloalkyl; and wherein the aliphatic and alicyclic moieties are unsubstituted or substituted by 1, 2, 3 or 4 identical or different groups $R^a$ as defined or preferably defined herein. In another preferred embodiment of the invention $R^A$ is halogen, cyano, $C_1$-$C_6$-alkyl, $C_1$-$C_6$-alkoxy, $C_2$-$C_6$-alkenyl, $C_2$-$C_6$-alkynyl or $C_3$-$C_8$-cycloalkyl; and wherein the aliphatic and alicyclic moieties are unsubstituted or substituted by 1, 2, 3 or 4 identical or 10 different groups selected from halogen, cyano, $C_1$-$C_6$-alkyl, $C_1$-$C_6$-alkoxy and $C_3$-$C_8$-cycloalkyl, in particular fluorine.

More preferably $R^A$ is halogen, cyano, $C_1$-$C_6$-alkyl, $C_1$-$C_6$-haloalkyl, $C_1$-$C_6$-alkoxy or $C_1$-$C_6$-haloalkoxy; in particular halogen, $C_1$-$C_6$-alkyl or $C_1$-$C_6$-haloalkyl; more particularly chlorine, fluorine, methyl, trifluoromethyl, difluoromethyl or fluoromethyl. Even more preferably $R^A$ is chlorine, fluorine or methyl.

According to a further embodiment, A is unsubstituted, more preferably A is phenyl which is unsubstituted.

In a preferred embodiment of the invention $R^a$ is halogen, cyano, $C_1$-$C_6$-alkyl, $C_1$-$C_6$-alkoxy or $C_3$-$C_8$-cycloalkyl. More preferably $R^a$ is halogen, in particular fluorine.

In one embodiment the invention relates to compounds of formula I, or the N-oxides, or the agriculturally acceptable salts thereof, wherein the cyclic moiety A is defined as described in (A.1) to (A.11),

(A.1)

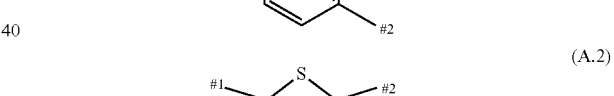
(A.2)

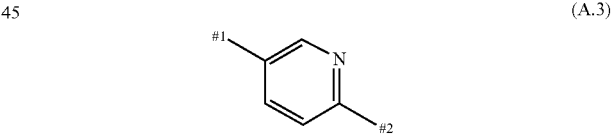
(A.3)

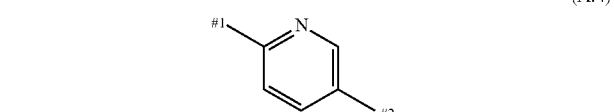
(A.4)

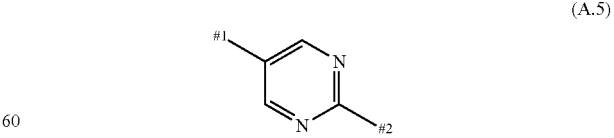
(A.5)

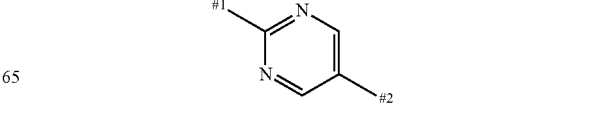
(A.6)

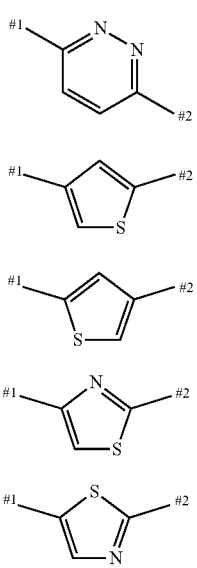

wherein #1 denotes the position which is bound to the trifluoromethyloxadiazole moiety and #2 denotes the position, which is connected to the moiety L in formula I; and wherein the cyclic moiety A is unsubstituted or substituted by 1 or 2 identical or different groups $R^A$ and wherein $R^A$ is as defined or preferably defined herein. In another embodiment the cyclic moieties A as defined in any one of (A.1) to (A.11) is unsubstituted or substituted by 1 or 2 identical or different groups $R^A$; and wherein $R^A$ is chlorine, fluorine or methyl. In a preferred embodiment the cyclic moiety A as defined in any one of (A.1) to (A.11) is unsubstituted.

In a preferred embodiment X is O.

In another embodiment L is #-C(=X)—NR—, wherein # denotes the position to which the cyclic group A is attached to; more preferably L is #-C(=O)—NR—, which compounds are of formula I.A:

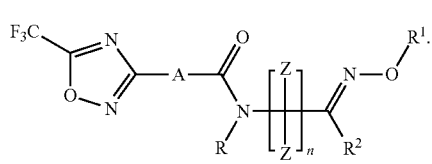

In another embodiment L is #-NR—C(=X)—, wherein # denotes the position to which the cyclic group A is attached to; more preferably L is #-NR—C(=O)—, which compounds are of formula I.B:

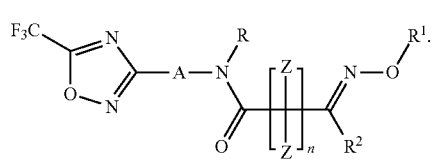

In another aspect of the invention R is hydrogen, $C_1$-$C_6$-alkyl, $C_1$-$C_6$-alkoxy, $C_2$-$C_6$-alkenyl, ethynyl, propargyl, $C_3$-$C_8$-cycloalkyl, $C_3$-$C_8$-cycloalkenyl; and wherein any of the aliphatic or cyclic groups are unsubstituted or substituted by 1, 2, 3, 4 or up to the maximum possible number of identical or different groups $R^{1a}$ as defined or preferably defined herein.

Preferably, R is hydrogen, $C_1$-$C_6$-alkyl, $C_2$-$C_6$-alkenyl, ethynyl, propargyl or $C_3$-$C_8$-cycloalkyl; and wherein any of the aliphatic or cyclic groups are unsubstituted or substituted by 1, 2, 3 or up to the maximum possible number of identical or different radicals $R^{1a}$ selected from halogen, cyano, $C_1$-$C_6$-alkyl, $C_1$-$C_6$-alkoxy and $C_3$-$C_8$-cycloalkyl; more preferably halogen, in particular fluorine. In another preferred aspect of the invention R is hydrogen, methy or ethyl; in particular hydrogen.

In one embodiment of the invention $R^{1a}$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_4$-alkylamino, di$C_1$-$C_4$-alkylamino, $C_1$-$C_6$-alkylthio, $C_1$-$C_6$-haloalkylthio or $C_3$-$C_8$-cycloalkyl. In another embodiment $R^{1a}$ is halogen, cyano, $NO_2$, OH, SH, $NH_2$, $C_1$-$C_6$-alkyl, $C_1$-$C_6$-haloalkyl, $C_1$-$C_6$-alkoxy or $C_1$-$C_6$-haloalkoxy; more preferably $R^{1a}$ is halogen, cyano, $NO_2$, OH, SH, $NH_2$, $C_1$-$C_4$-alkyl or $C_1$-$C_4$-alkoxy; even more preferably $R^{1a}$ is halogen; in particular $R^{1a}$ is fluorine.

In one embodiment of the invention n is 0, 1 or 2. In a preferred embodiment n is 0 or 1, in particular n is 1.

In another embodiment L is #-C(=O)—NR—, wherein # denotes the position to which the cyclic group A is attached to, n is 0, and which compounds are of formula I.A.1:

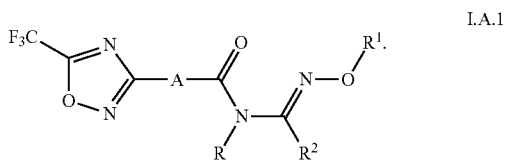

In a further embodiment L is #-C(=O)—NR—, wherein # denotes the position to which the cyclic group A is attached to, n is 1, and which compounds are of formula I.A.2:

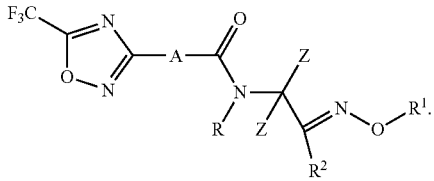

In a further embodiment L is #-C(=O)—NR—, wherein # denotes the position to which the cyclic group A is attached to, n is 2, and which compounds are of formula I.A.3:

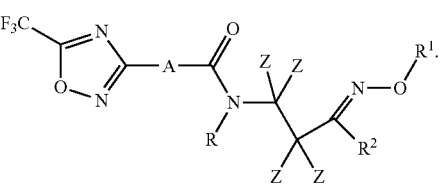

In one embodiment of the invention Z, which may be the same or different to any other Z, is hydrogen, halogen, $C_1$-$C_6$-alkyl, $C_1$-$C_6$-alkoxy, $C_3$-$C_8$-cycloalkyl, phenyl-$C_1$-$C_4$-alkyl; and wherein any of the aliphatic or cyclic groups are unsubstituted or substituted by 1, 2, 3, 4 or up to the maximum possible number of identical or different groups $R^{1a}$, or two radicals Z that are bound to the same carbon atom may form together with said carbon atom a $C_3$-$C_8$-cycloalkyl.

In another embodiment Z, which may be the same or different to any other Z, is hydrogen, halogen, $C_1$-$C_6$-alkyl, $C_1$-$C_6$-alkoxy, $C_3$-$C_8$-cycloalkyl; and wherein any of the aliphatic or cyclic groups are unsubstituted or substituted by 1, 2, 3, 4 or up to the maximum possible number of identical or different groups $R^{1a}$, or two radicals Z that are bound to the same carbon atom may form together with said carbon atom a cyclopropyl.

In a further embodiment Z, which may be the same or different to any other Z, is hydrogen, halogen, $C_1$-$C_4$-alkyl wherein any of the aliphatic groups are unsubstituted or substituted by 1 or 2 identical or different groups $R^{1a}$ selected from halogen; or two radicals Z that are bound to the same carbon atom may form together with said carbon atom a cyclopropyl.

More preferably Z, which may be the same or different to any other Z, is hydrogen or methyl; in particular Z is hydrogen.

In a further embodiment L is #-C(=O)—NR—, wherein # denotes the position to which the cyclic group A is attached to, n is 1 and both Z are hydrogen, which compounds are of formula I.A.2.a:

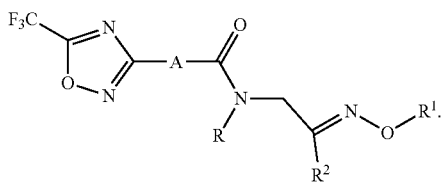

I.A.2.a

In a further embodiment L is #-C(=O)—NR—, wherein # denotes the position to which the cyclic group A is attached to, n is 1 and one Z is hydrogen and one Z is methyl, which compounds are of formula I.A.2.b:

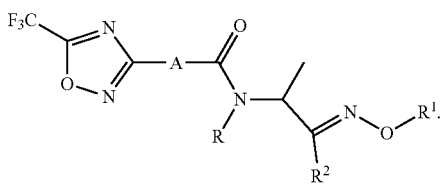

I.A.2.b

In a further embodiment L is #-C(=O)—NR—, wherein # denotes the position to which the cyclic group A is attached to, n is 1 and both Z are methyl, which compounds are of formula I.A.2.c:

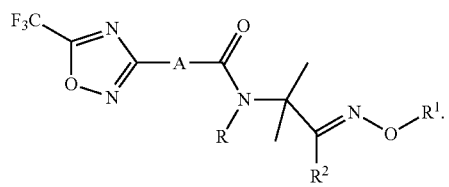

I.A.2.c

In a further embodiment L is #-C(=O)—NR—, wherein # denotes the position to which the cyclic group A is attached to, n is 1 and both Z that are bound to the same carbon atom form together with said carbon atom a cyclopropyl, which compounds are of formula I.A.2.d:

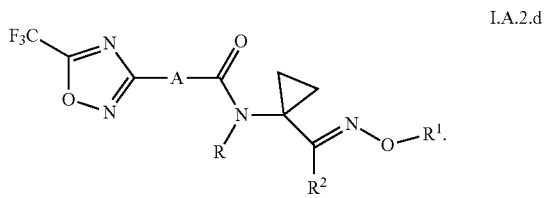

I.A.2.d

In a further embodiment L is #-C(=O)—NR—, wherein # denotes the position to which the cyclic group A is attached to, n is 2 and all four Z radicals are hydrogen, which compounds are of formula I.A.3.a:

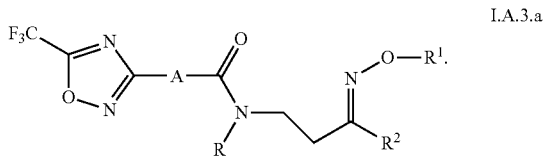

I.A.3.a

In a further embodiment L is #-C(=O)—NR—, wherein # denotes the position to which the cyclic group A is attached to, n is 2 and one Z radical on the carbon attached to the nitrogen of the amide group is methyl and the other three Z radicals are hydrogen, which compounds are of formula I.A.3.b:

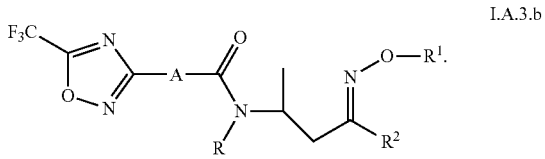

I.A.3.b

In a further embodiment L is #-C(=O)—NR—, wherein # denotes the position to which the cyclic group A is attached to, n is 2 and one Z radical on the carbon attached to the carbon of the oxime group is methyl and the other three Z radicals are hydrogen, which compounds are of formula I.A.3.c

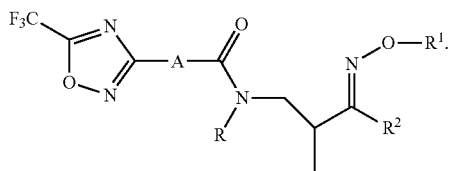

I.A.3.c

In a further embodiment L is #-C(=O)—NR—, wherein # denotes the position to which the cyclic group A is attached to, n is 2 and one of the Z radicals attached to each of the carbon atoms is methyl, the other one is hydrogen, which compounds are of formula I.A.3.d:

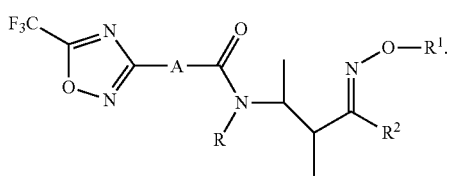

I.A.3.d

In another embodiment L is #-NR—C(=O)—, wherein # denotes the position to which the cyclic group A is attached to, n is 0, and which compounds are of formula I.B.1:

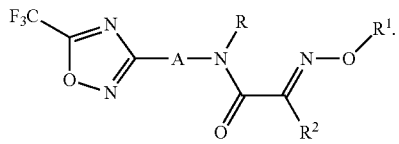

I.B.1

In a further embodiment L is #-NR—C(=O)—, wherein # denotes the position to which the cyclic group A is attached to, n is 1 and both Z are hydrogen, which compounds are of formula I.B.2.a:

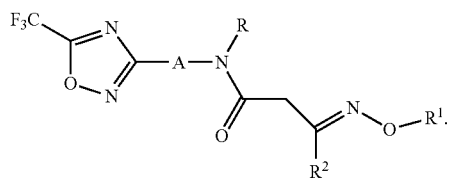

I.B.2.a

In a further embodiment L is #-NR—C(=O)—, wherein # denotes the position to which the cyclic group A is attached to, n is 1 and one Z is hydrogen and one Z is methyl, which compounds are of formula I.B.2.b:

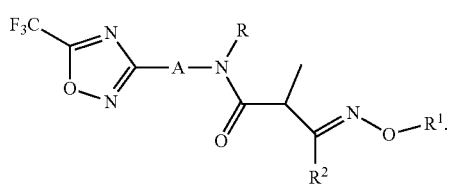

I.B.2.b

In a further embodiment L is #-NR—C(=O)—, wherein # denotes the position to which the cyclic group A is attached to, n is 1 and both Z are methyl, which compounds are of formula I.B.2.c:

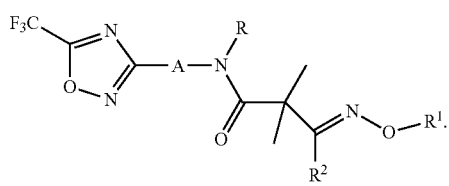

I.B.2.c

In a further embodiment L is #-NR—C(=O)—, wherein # denotes the position to which the cyclic group A is attached to, n is 1 and both Z that are bound to the same carbon atom form together with said carbon atom a cyclopropyl, which compounds are of formula I.B.2.d:

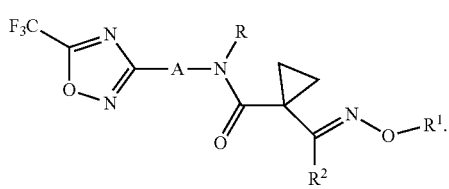

I.B.2.d

In a further embodiment L is #-NR—C(=O)—, wherein # denotes the position to which the cyclic group A is attached to, n is 2 and all four Z radicals are hydrogen, which compounds are of formula I.B.3.a:

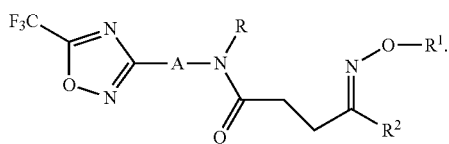

I.B.3.a

In a further embodiment L is #-NR—C(=O)—, wherein # denotes the position to which the cyclic group A is attached to, n is 2 and one Z radical on the carbon attached to the nitrogen of the amide group is methyl and the other three Z radicals are hydrogen, which compounds are of formula I.B.3.b:

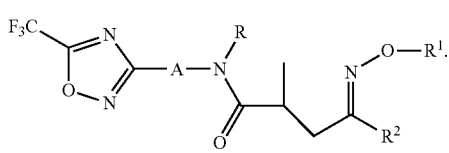

I.B.3.b

In a further embodiment L is #-NR—C(=O)—, wherein # denotes the position to which the cyclic group A is attached to, n is 2 and one Z radical on the carbon attached to the carbon of the oxime group is methyl and the other three Z radicals are hydrogen, which compounds are of formula I.B.3.c:

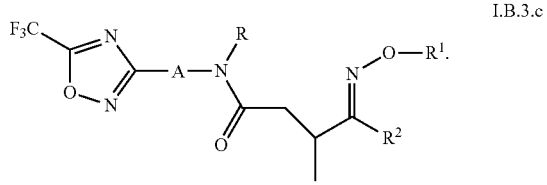

I.B.3.c

In a further embodiment L is #-NR—C(=O)—, wherein # denotes the position to which the cyclic group A is attached to, n is 2 and one of the Z radicals attached to each of the carbon atoms is methyl, the other one is hydrogen, which compounds are of formula I.B.3.d:

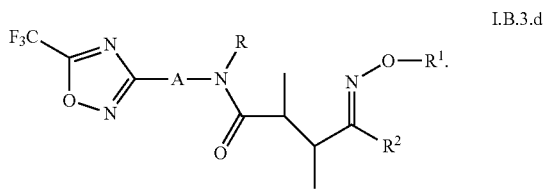

I.B.3.d

In one embodiment of the invention $R^1$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, phenyl-$C_1$-$C_4$-alkyl, or a five- to six-membered aromatic heterocyclyl which, in addition to carbon atoms, contains one to three heteroatoms from the group consisting of O, N and S as ring members; and wherein any of the above-mentioned aliphatic or cyclic groups are unsubstituted or substituted by 1, 2, 3 or up to the maximum possible number of identical or different groups $R^{1a}$ as defined or preferably defined herein.

In another embodiment $R^1$ is hydrogen, $C_1$-$C_6$-alkyl, $C_2$-$C_6$-alkenyl, $C_2$-$C_6$-alkynyl, $C_3$-$C_8$-cycloalkyl wherein any of the above-mentioned aliphatic or cyclic groups are unsubstituted or substituted by 1, 2, 3 or up to the maximum possible number of identical or different groups $R^{1a}$ as defined or preferably defined herein.

In a further embodiment $R^1$ is hydrogen, $C_1$-$C_4$-alkyl, $C_2$-$C_4$-alkenyl, $C_2$-$C_4$-alkynyl wherein any of the above-mentioned groups are unsubstituted or substituted by 1, 2, 3 or up to the maximum possible number of identical or different groups $R^{1a}$ selected from halogen.

In one embodiment of the invention $R^2$ is hydrogen, cyano, $C_1$-$C_6$-alkyl, $C_2$-$C_6$-alkenyl, $C_2$-$C_6$-alkynyl, $C_3$-$C_6$-cycloalkyl, C(=O)—($C_1$-$C_6$-alkyl), C(=O)—($C_1$-$C_6$-alkoxy), $C_1$-$C_4$-alkylamino, di$C_1$-$C_4$-alkylamino, phenyl-$C_1$-$C_4$-alkyl, heteroaryl-$C_1$-$C_4$-alkyl or phenyl; wherein the heteroaryl group in heteroaryl-$C_1$-$C_4$-alkyl is a 5- or 6-membered aromatic heterocycle, wherein the ring member atoms of said 5- or 6-membered aromatic heterocycle include besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$ as defined or preferably defined herein.

In another embodiment $R^2$ is hydrogen, cyano, $C_1$-$C_6$-alkyl, $C_2$-$C_6$-alkenyl, C(=O)—($C_1$-$C_6$-alkyl), C(=O)—($C_1$-$C_6$-alkoxy), $C_1$-$C_4$-alkylamino or di$C_1$-$C_4$-alkylamino, wherein any of the above-mentioned aliphatic groups are unsubstituted or substituted by 1, 2, 3 or up to the maximum possible number of identical or different groups $R^{1a}$ as defined or preferably defined herein.

In a further embodiment $R^2$ is hydrogen, cyano, $C_1$-$C_4$-alkyl, C(=O)—($C_1$-$C_4$-alkyl) or C(=O)—($C_1$-$C_4$-alkoxy) wherein any of the above-mentioned aliphatic groups are unsubstituted or substituted by 1, 2, 3 or up to the maximum possible number of identical or different groups $R^{1a}$ as defined or preferably defined herein.

In a further embodiment $R^2$ is hydrogen, $C_1$-$C_4$-alkyl, C(=O)—($C_1$-$C_2$-alkyl) or C(=O)—($C_1$-$C_2$-alkoxy) wherein any of the above-mentioned aliphatic groups are unsubstituted or substituted by 1, 2, 3 or up to the maximum possible number of identical or different groups $R^{1a}$ selected from halogen.

In a further embodiment $R^2$ is hydrogen or $C_1$-$C_4$-alkyl which is unsubstituted or substituted by 1, 2, 3 or 4 identical or different groups $R^{1a}$ selected from halogen.

In a further embodiment $R^2$ is hydrogen or $C_1$-$C_2$-alkyl which is unsubstituted or substituted by 1, 2, 3 or 4 identical or different groups $R^{1a}$ selected from halogen; more preferably $R^2$ is hydrogen or methyl.

In a further embodiment $R^2$ is cyano.

In a further embodiment the invention relates to compounds of formula I, or the N-oxides, or the agriculturally acceptable salts thereof wherein:
A is a phenyl, thiophene or pyridine ring which is unsubstituted or substituted by 1 or 2 identical or different groups $R^A$; wherein
  $R^A$ is halogen, cyano, $C_1$-$C_6$-alkyl, $C_1$-$C_6$-haloalkyl, $C_1$-$C_6$-alkoxy or $C_1$-$C_6$-haloalkoxy;
L is #-C(=O)—NR— or #-NR—C(=O)—, wherein # denotes the position to which the cyclic group A is attached to; wherein
  R is hydrogen, $C_1$-$C_6$-alkyl, $C_2$-$C_6$-alkenyl, ethynyl, propargyl or $C_3$-$C_8$-cycloalkyl; and wherein any of the aliphatic or cyclic groups are unsubstituted or substituted by 1, 2, 3 or up to the maximum possible number of identical or different radicals $R^{1a}$ selected from halogen;
n is 0, 1 or 2;
Z, which may be the same or different to any other Z, is hydrogen, halogen or $C_1$-$C_2$-alkyl which is unsubstituted or substituted by 1, 2 or 3 identical or different groups $R^{1a}$ selected from halogen; or
two radicals Z that are bound to the same carbon atom may form together with said carbon atom a cyclopropyl;
$R^1$ is hydrogen, $C_1$-$C_4$-alkyl, $C_2$-$C_4$-alkenyl, $C_2$-$C_4$-alkynyl wherein any of the above-mentioned aliphatic groups are unsubstituted or substituted by 1, 2, 3 or up to the maximum possible number of identical or different groups $R^{1a}$ selected from halogen; $R^2$ hydrogen, cyano, $C_1$-$C_6$-alkyl, $C_2$-$C_6$-alkenyl, C(=O)—($C_1$-$C_6$-alkyl), C(=O)—($C_1$-$C_6$-alkoxy),
$C_1$-$C_4$-alkylamino or di$C_1$-$C_4$-alkylamino, wherein any of the above-mentioned aliphatic groups are unsubstituted or substituted by 1, 2, 3 or up to the maximum possible number of identical or different groups $R^{1a}$ selected from halogen.

In a further embodiment the invention relates to compounds of formula I, or the N-oxides, or the agriculturally acceptable salts thereof wherein:
A is (A.2), (A3), (A.4), (A.8) or (A.9) which cyclic moiety A is unsubstituted or substituted by 1 or 2 identical or different groups $R^A$ selected from halogen;

L is #-C(=O)—NR— or #-NR—C(=O)—, wherein # denotes the position to which the cyclic group A is attached to; wherein
R is hydrogen, $C_1$-$C_6$-alkyl, $C_2$-$C_6$-alkenyl, ethynyl, propargyl or $C_3$-$C_8$-cycloalkyl; and wherein any of the aliphatic or cyclic groups are unsubstituted or substituted by 1, 2, 3 or up to the maximum possible number of identical or different radicals $R^{1a}$ selected from halogen;

n is 0, 1 or 2;

Z, which may be the same or different to any other Z, is hydrogen, halogen or $C_1$-$C_2$-alkyl which is unsubstituted or substituted by 1, 2 or 3 identical or different groups $R^{1a}$ selected from halogen; or two radicals Z that are bound to the same carbon atom may form together with said carbon atom a cyclopropyl;

$R^1$ is hydrogen, $C_1$-$C_4$-alkyl, $C_2$-$C_4$-alkenyl, $C_2$-$C_4$-alkynyl wherein any of the above-mentioned aliphatic groups are unsubstituted or substituted by 1, 2, 3 or up to the maximum possible number of identical or different groups $R^{1a}$ selected from halogen;

$R^2$ hydrogen, cyano, $C_1$-$C_6$-alkyl, $C_2$-$C_6$-alkenyl, C(=O)—($C_1$-$C_6$-alkyl), C(=O)—($C_1$-$C_6$-alkoxy), $C_1$-$C_4$-alkylamino or di$C_1$-$C_4$-alkylamino, wherein any of the above-mentioned aliphatic groups are unsubstituted or substituted by 1, 2, 3 or up to the maximum possible number of identical or different groups $R^{1a}$ selected from halogen.

In a further embodiment the invention relates to compounds of formula I, or the N-oxides, or the agriculturally acceptable salts thereof wherein:

A is (A.2), (A3), (A.4), (A.8) or (A.9) which cyclic moiety A is unsubstituted or substituted by 1 or 2 identical or different groups $R^A$ selected from halogen;

L is #-C(=O)—NR—, wherein # denotes the position to which the cyclic group A is attached to; wherein
R is hydrogen, $C_1$-$C_6$-alkyl, $C_2$-$C_6$-alkenyl, ethynyl, propargyl or $C_3$-$C_8$-cycloalkyl; and wherein any of the aliphatic or cyclic groups are unsubstituted or substituted by 1, 2, 3 or up to the maximum possible number of identical or different radicals $R^{1a}$ selected from halogen;

n is 0, 1 or 2;

Z, which may be the same or different to any other Z, is hydrogen, halogen or $C_1$-$C_2$-alkyl which is unsubstituted or substituted by 1, 2 or 3 identical or different groups $R^{1a}$ selected from halogen; or two radicals Z that are bound to the same carbon atom may form together with said carbon atom a cyclopropyl;

$R^1$ is hydrogen, $C_1$-$C_4$-alkyl, $C_2$-$C_4$-alkenyl, $C_2$-$C_4$-alkynyl wherein any of the above-mentioned aliphatic groups are unsubstituted or substituted by 1, 2, 3 or up to the maximum possible number of identical or different groups $R^{1a}$ selected from halogen;

$R^2$ hydrogen, cyano, $C_1$-$C_6$-alkyl, $C_2$-$C_6$-alkenyl, C(=O)—($C_1$-$C_6$-alkyl), C(=O)—($C_1$-$C_6$-alkoxy), $C_1$-$C_4$-alkylamino or di$C_1$-$C_4$-alkylamino, wherein any of the above-mentioned aliphatic groups are unsubstituted or substituted by 1, 2, 3 or up to the maximum possible number of identical or different groups $R^{1a}$ selected from halogen.

In a further embodiment the invention relates to compounds of formula I.1, or the N-oxides, or the agriculturally acceptable salts thereof

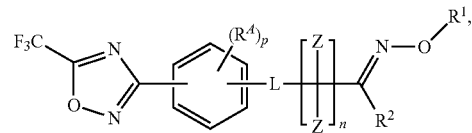

wherein:
$R^A$ is halogen, cyano, $C_1$-$C_6$-alkyl, $C_1$-$C_6$-haloalkyl, $C_1$-$C_6$-alkoxy or $C_1$-$C_6$-haloalkoxy;

p is 0, 1 or 2;

L is #-C(=O)—NR— or #-NR—C(=O)—, wherein # denotes the position to which the cyclic group A is attached to; wherein
R is hydrogen, $C_1$-$C_6$-alkyl, $C_2$-$C_6$-alkenyl, ethynyl, propargyl or $C_3$-$C_8$-cycloalkyl; and wherein any of the aliphatic or cyclic groups are unsubstituted or substituted by 1, 2, 3 or up to the maximum possible number of identical or different radicals $R^{1a}$ selected from halogen;

n is 0, 1 or 2;

Z, which may be the same or different to any other Z, is hydrogen, halogen or $C_1$-$C_2$-alkyl which is unsubstituted or substituted by 1, 2 or 3 identical or different groups $R^{1a}$ selected from halogen; or two radicals Z that are bound to the same carbon atom may form together with said carbon atom a cyclopropyl;

$R^1$ is hydrogen, $C_1$-$C_4$-alkyl, $C_2$-$C_4$-alkenyl, $C_2$-$C_4$-alkynyl wherein any of the above-mentioned aliphatic groups are unsubstituted or substituted by 1, 2, 3 or up to the maximum possible number of identical or different groups $R^{1a}$ selected from halogen;

$R^2$ hydrogen, cyano, $C_1$-$C_6$-alkyl, $C_2$-$C_6$-alkenyl, C(=O)—($C_1$-$C_6$-alkyl), C(=O)—($C_1$-$C_6$-alkoxy), $C_1$-$C_4$-alkylamino or di$C_1$-$C_4$-alkylamino, wherein any of the above-mentioned aliphatic groups are unsubstituted or substituted by 1, 2, 3 or up to the maximum possible number of identical or different groups $R^{1a}$ selected from halogen.

In a further embodiment the invention relates to compounds of formula I.1, or the N-oxides, or the agriculturally acceptable salts thereof, wherein:

$R^A$ is halogen, cyano, $C_1$-$C_6$-alkyl, $C_1$-$C_6$-haloalkyl, $C_1$-$C_6$-alkoxy or $C_1$-$C_6$-haloalkoxy;

p is 0, 1 or 2;

L is #-C(=O)—NR— or #-NR—C(=O)—, wherein # denotes the position to which the cyclic group A is attached to; wherein
R is hydrogen, $C_1$-$C_6$-alkyl, $C_2$-$C_6$-alkenyl, ethynyl, propargyl or $C_3$-$C_8$-cycloalkyl; and wherein any of the aliphatic or cyclic groups are unsubstituted or substituted by 1, 2, 3 or up to the maximum possible number of identical or different radicals $R^{1a}$ selected from halogen;

n is 0, 1 or 2;

Z, which may be the same or different to any other Z, is hydrogen, halogen or $C_1$-$C_2$-alkyl which is unsubstituted or substituted by 1, 2 or 3 identical or different groups $R^{1a}$ selected from halogen; or two radicals Z that are bound to the same carbon atom may form together with said carbon atom a cyclopropyl;

$R^1$ is hydrogen, $C_1$-$C_4$-alkyl, $C_2$-$C_4$-alkenyl, $C_2$-$C_4$-alkynyl wherein any of the above-mentioned aliphatic groups are unsubstituted or substituted by 1, 2, 3 or up to the maximum possible number of identical or different groups $R^{1a}$ selected from halogen;

R² hydrogen, $C_1$-$C_6$-alkyl, $C_2$-$C_6$-alkenyl, C(=O)—($C_1$-$C_6$-alkyl), C(=O)—($C_1$-$C_6$-alkoxy), $C_1$-$C_4$-alkylamino or di$C_1$-$C_4$-alkylamino, wherein any of the above-mentioned aliphatic groups are unsubstituted or substituted by 1, 2, 3 or up to the maximum possible number of identical or different groups $R^{1a}$ selected from halogen.

In a further embodiment the invention relates to compounds of formula I.2, or the N-oxides, or the agriculturally acceptable salts thereof

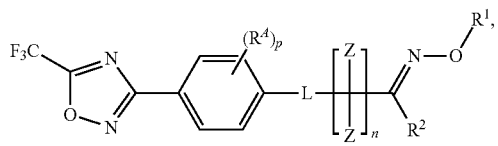

I.2 wherein:
$R^A$ is halogen;
p is 0, 1 or 2;
L is #-C(=O)—NR—, wherein # denotes the position to which the cyclic group A is attached to; wherein
  R is hydrogen or $C_1$-$C_2$-alkyl which is unsubstituted or substituted by 1, 2, 3 or 4 identical or different radicals $R^{1a}$ selected from halogen;
n is 0, 1 or 2;
Z, which may be the same or different to any other Z, is hydrogen, halogen or $C_1$-$C_2$-alkyl which is unsubstituted or substituted by 1, 2 or 3 identical or different groups $R^{1a}$ selected from halogen; or
two radicals Z that are bound to the same carbon atom may form together with said carbon atom a cyclopropyl;
$R^1$ is hydrogen, $C_1$-$C_4$-alkyl, $C_2$-$C_4$-alkenyl, $C_2$-$C_4$-alkynyl wherein any of the above-mentioned aliphatic groups are unsubstituted or substituted by 1, 2, 3 or up to the maximum possible number of identical or different groups $R^{1a}$ selected from halogen;
R² hydrogen, $C_1$-$C_6$-alkyl, $C_2$-$C_6$-alkenyl, C(=O)—($C_1$-$C_6$-alkyl), C(=O)—($C_1$-$C_6$-alkoxy), $C_1$-$C_4$-alkylamino or di$C_1$-$C_4$-alkylamino, wherein any of the above-mentioned aliphatic groups are unsubstituted or substituted by 1, 2, 3 or up to the maximum possible number of identical or different groups $R^{1a}$ selected from halogen.

In one embodiment of the invention L is #-C(=O)—NR—, wherein # denotes the position to which the cyclic group A is attached to; A is 1,4-phenylene and n is 0, which compounds are of formula I.2.1:

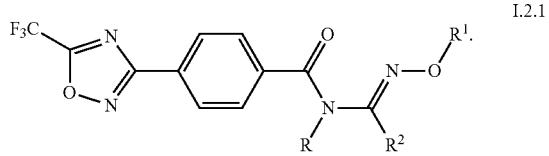

I.2.1

In another embodiment L is #-C(=O)—NR—, wherein # denotes the position to which the cyclic group A is attached to; A is 1,4-phenylene; n is 1 and both Z are hydrogen, which compounds are of formula I.2.2.a:

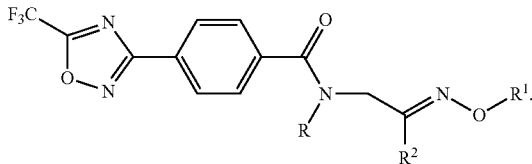

I.2.2.a

In a further embodiment L is #-C(=O)—NR—, wherein # denotes the position to which the cyclic group A is attached to; A is 1,4-phenylene; n is 1 and one Z is hydrogen and one Z is methyl, which compounds are of formula I.2.2.b:

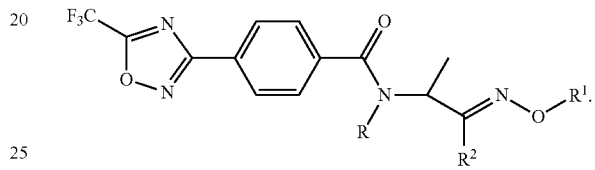

I.2.2.b

In a further embodiment L is #-C(=O)—NR—, wherein # denotes the position to which the cyclic group A is attached to; A is 1,4-phenylene; R is hydrogen, n is 1 and both Z are methyl, which compounds are of formula I.2.2.c:

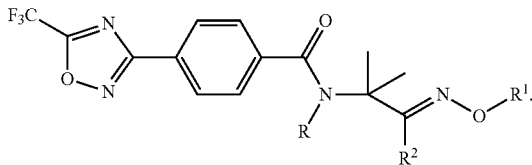

I.2.2.c

In a further embodiment L is #-C(=O)—NR—, wherein # denotes the position to which the cyclic group A is attached to; A is 1,4-phenylene; R is hydrogen, n is 1 and both Z that are bound to the same carbon atom form together with said carbon atom a cyclopropyl, which compounds are of formula I.2.2.d:

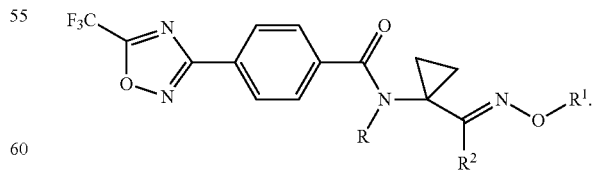

I.2.2.d

In a further embodiment L is #-C(=O)—NR—, wherein # denotes the position to which the cyclic group A is attached to; n is 2 and all four Z radicals are hydrogen, which compounds are of formula I.2.3.a:

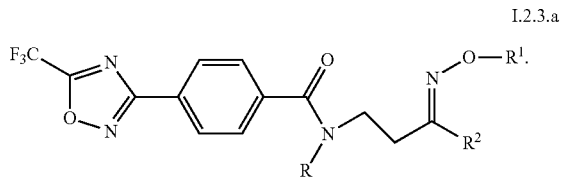

I.2.3.a

In a further embodiment L is #-C(=O)—NR—, wherein # denotes the position to which the cyclic group A is attached to; n is 2 and three Z radicals are hydrogen and one Z radical is methyl, particularly compounds of formula I.2.3.b:

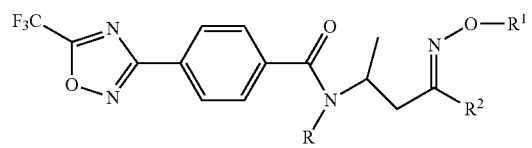

I.2.3.b

In a further embodiment L is #-C(=O)—NR—, wherein # denotes the position to which the cyclic group A is attached to; n is 2 and two Z radicals are hydrogen and two Z radicals are methyl, particularly compounds of formula I.2.3.c:

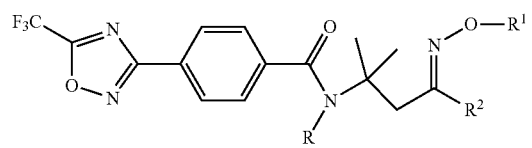

I.2.3.c

In a further embodiment L is #-C(=O)—NR—, wherein # denotes the position to which the cyclic group A is attached to; n is 2 and three Z radicals are hydrogen and one Z radical is methyl, particularly compounds of formula I.2.3.d:

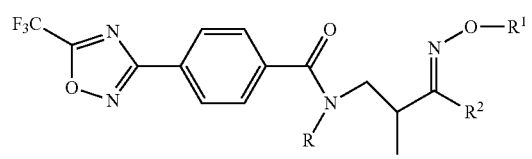

I.2.3.d

In a further embodiment L is #-C(=O)—NR—, wherein # denotes the position to which the cyclic group A is attached to; n is 2 and two Z radicals are hydrogen and two Z radicals are methyl, particularly compounds of formula I.2.3.e:

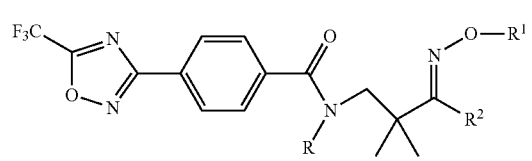

I.2.3.e

In a further embodiment L is #-C(=O)—NR—, wherein # denotes the position to which the cyclic group A is attached to; n is 2 and three Z radicals are hydrogen and one Z radical is ethyl, particularly compounds of formula I.2.3.f:

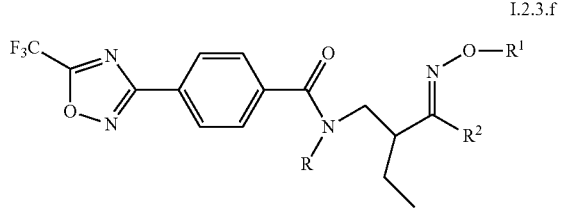

I.2.3.f

In a further embodiment L is #-C(=O)—NR—, wherein # denotes the position to which the cyclic group A is attached to; n is 2 and two Z radicals are hydrogen and two adjacent Z radicals together with the carbon atom to which they are attached from a cyclopropyl ring, particularly compounds of formula I.2.3.g:

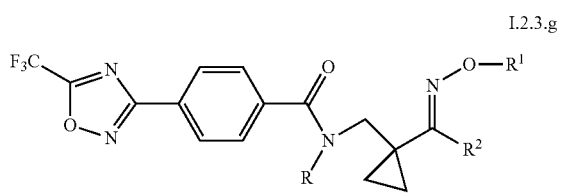

I.2.3.g

Further embodiments relate to compounds I in which $R^1$ and $R^2$ is one of the following meanings R-1 to R-195 as shown in the lines of Table A:

TABLE A

| No. | $R^1$ | $R^2$ |
|---|---|---|
| R-1 | H | H |
| R-2 | $CH_3$ | H |
| R-3 | $CH_2CH_3$ | H |
| R-4 | $CH_2CH_2CH_3$ | H |
| R-5 | $CH_2CH_2CH_2CH_3$ | H |
| R-6 | $CH(CH_3)_2$ | H |
| R-7 | $C(CH_3)_3$ | H |
| R-8 | $CH_2$-phenyl | H |
| R-9 | $CH_2$-cyclopropyl | H |
| R-10 | $CF_3$ | H |
| R-11 | $CHF_2$ | H |
| R-12 | $CH_2$—CH=$CH_2$ | H |
| R-13 | $CH_2$—C≡CH | H |
| R-14 | H | CN |
| R-15 | $CH_3$ | CN |
| R-16 | $CH_2CH_3$ | CN |
| R-17 | $CH_2CH_2CH_3$ | CN |
| R-18 | $CH_2CH_2CH_2CH_3$ | CN |
| R-19 | $CH(CH_3)_2$ | CN |
| R-20 | $C(CH_3)_3$ | CN |
| R-21 | $CH_2$-phenyl | CN |
| R-22 | $CH_2$-cyclopropyl | CN |
| R-23 | $CF_3$ | CN |
| R-24 | $CHF_2$ | CN |
| R-25 | $CH_2$—CH=$CH_2$ | CN |
| R-26 | $CH_2$—C≡CH | CN |
| R-27 | H | $CH_3$ |
| R-28 | $CH_3$ | $CH_3$ |
| R-29 | $CH_2CH_3$ | $CH_3$ |
| R-30 | $CH_2CH_2CH_3$ | $CH_3$ |
| R-31 | $CH_2CH_2CH_2CH_3$ | $CH_3$ |
| R-32 | $CH(CH_3)_2$ | $CH_3$ |
| R-33 | $C(CH_3)_3$ | $CH_3$ |

TABLE A-continued

| No. | R$^1$ | R$^2$ |
|---|---|---|
| R-34 | CH$_2$-phenyl | CH$_3$ |
| R-35 | CH$_2$-cyclopropyl | CH$_3$ |
| R-36 | CF$_3$ | CH$_3$ |
| R-37 | CHF$_2$ | CH$_3$ |
| R-38 | CH$_2$—CH=CH$_2$ | CH$_3$ |
| R-39 | CH$_2$—C≡CH | CH$_3$ |
| R-40 | H | CH$_2$CH$_3$ |
| R-41 | CH$_3$ | CH$_2$CH$_3$ |
| R-42 | CH$_2$CH$_3$ | CH$_2$CH$_3$ |
| R-43 | CH$_2$CH$_2$CH$_3$ | CH$_2$CH$_3$ |
| R-44 | CH$_2$CH$_2$CH$_2$CH$_3$ | CH$_2$CH$_3$ |
| R-45 | CH(CH$_3$)$_2$ | CH$_2$CH$_3$ |
| R-46 | C(CH$_3$)$_3$ | CH$_2$CH$_3$ |
| R-47 | CH$_2$-phenyl | CH$_2$CH$_3$ |
| R-48 | CH$_2$-cyclopropyl | CH$_2$CH$_3$ |
| R-49 | CF$_3$ | CH$_2$CH$_3$ |
| R-50 | CHF$_2$ | CH$_2$CH$_3$ |
| R-51 | CH$_2$—CH=CH$_2$ | CH$_2$CH$_3$ |
| R-52 | CH$_2$—C≡CH | CH$_2$CH$_3$ |
| R-53 | H | CH$_2$CH$_2$CH$_3$ |
| R-54 | CH$_3$ | CH$_2$CH$_2$CH$_3$ |
| R-55 | CH$_2$CH$_3$ | CH$_2$CH$_2$CH$_3$ |
| R-56 | CH$_2$CH$_2$CH$_3$ | CH$_2$CH$_2$CH$_3$ |
| R-57 | CH$_2$CH$_2$CH$_2$CH$_3$ | CH$_2$CH$_2$CH$_3$ |
| R-58 | CH(CH$_3$)$_2$ | CH$_2$CH$_2$CH$_3$ |
| R-59 | C(CH$_3$)$_3$ | CH$_2$CH$_2$CH$_3$ |
| R-60 | CH$_2$-phenyl | CH$_2$CH$_2$CH$_3$ |
| R-61 | CH$_2$-cyclopropyl | CH$_2$CH$_2$CH$_3$ |
| R-62 | CF$_3$ | CH$_2$CH$_2$CH$_3$ |
| R-63 | CHF$_2$ | CH$_2$CH$_2$CH$_3$ |
| R-64 | CH$_2$—CH=CH$_2$ | CH$_2$CH$_2$CH$_3$ |
| R-65 | CH$_2$—C≡CH | CH$_2$CH$_2$CH$_3$ |
| R-66 | H | CH$_2$CH$_2$CH$_2$CH$_3$ |
| R-67 | CH$_3$ | CH$_2$CH$_2$CH$_2$CH$_3$ |
| R-68 | CH$_2$CH$_3$ | CH$_2$CH$_2$CH$_2$CH$_3$ |
| R-69 | CH$_2$CH$_2$CH$_3$ | CH$_2$CH$_2$CH$_2$CH$_3$ |
| R-70 | CH$_2$CH$_2$CH$_2$CH$_3$ | CH$_2$CH$_2$CH$_2$CH$_3$ |
| R-71 | CH(CH$_3$)$_2$ | CH$_2$CH$_2$CH$_2$CH$_3$ |
| R-72 | C(CH$_3$)$_3$ | CH$_2$CH$_2$CH$_2$CH$_3$ |
| R-73 | CH$_2$-phenyl | CH$_2$CH$_2$CH$_2$CH$_3$ |
| R-74 | CH$_2$-cyclopropyl | CH$_2$CH$_2$CH$_2$CH$_3$ |
| R-75 | CF$_3$ | CH$_2$CH$_2$CH$_2$CH$_3$ |
| R-76 | CHF$_2$ | CH$_2$CH$_2$CH$_2$CH$_3$ |
| R-77 | CH$_2$—CH=CH$_2$ | CH$_2$CH$_2$CH$_2$CH$_3$ |
| R-78 | CH$_2$—C≡CH | CH$_2$CH$_2$CH$_2$CH$_3$ |
| R-79 | H | CH(CH$_3$)$_2$ |
| R-80 | CH$_3$ | CH(CH$_3$)$_2$ |
| R-81 | CH$_2$CH$_3$ | CH(CH$_3$)$_2$ |
| R-82 | CH$_2$CH$_2$CH$_3$ | CH(CH$_3$)$_2$ |
| R-83 | CH$_2$CH$_2$CH$_2$CH$_3$ | CH(CH$_3$)$_2$ |
| R-84 | CH(CH$_3$)$_2$ | CH(CH$_3$)$_2$ |
| R-85 | C(CH$_3$)$_3$ | CH(CH$_3$)$_2$ |
| R-86 | CH$_2$-phenyl | CH(CH$_3$)$_2$ |
| R-87 | CH$_2$-cyclopropyl | CH(CH$_3$)$_2$ |
| R-88 | CF$_3$ | CH(CH$_3$)$_2$ |
| R-89 | CHF$_2$ | CH(CH$_3$)$_2$ |
| R-90 | CH$_2$—CH=CH$_2$ | CH(CH$_3$)$_2$ |
| R-91 | CH$_2$—C≡CH | CH(CH$_3$)$_2$ |
| R-92 | H | CH$_2$CH(CH$_3$)$_2$ |
| R-93 | CH$_3$ | CH$_2$CH(CH$_3$)$_2$ |
| R-94 | CH$_2$CH$_3$ | CH$_2$CH(CH$_3$)$_2$ |
| R-95 | CH$_2$CH$_2$CH$_3$ | CH$_2$CH(CH$_3$)$_2$ |
| R-96 | CH$_2$CH$_2$CH$_2$CH$_3$ | CH$_2$CH(CH$_3$)$_2$ |
| R-97 | CH(CH$_3$)$_2$ | CH$_2$CH(CH$_3$)$_2$ |
| R-98 | C(CH$_3$)$_3$ | CH$_2$CH(CH$_3$)$_2$ |
| R-99 | CH$_2$-phenyl | CH$_2$CH(CH$_3$)$_2$ |
| R-100 | CH$_2$-cyclopropyl | CH$_2$CH(CH$_3$)$_2$ |
| R-101 | CF$_3$ | CH$_2$CH(CH$_3$)$_2$ |
| R-102 | CHF$_2$ | CH$_2$CH(CH$_3$)$_2$ |
| R-103 | CH$_2$—CH=CH$_2$ | CH$_2$CH(CH$_3$)$_2$ |
| R-104 | CH$_2$—C≡CH | CH$_2$CH(CH$_3$)$_2$ |
| R-105 | H | C(CH$_3$)$_3$ |
| R-106 | CH$_3$ | C(CH$_3$)$_3$ |
| R-107 | CH$_2$CH$_3$ | C(CH$_3$)$_3$ |
| R-108 | CH$_2$CH$_2$CH$_3$ | C(CH$_3$)$_3$ |
| R-109 | CH$_2$CH$_2$CH$_2$CH$_3$ | C(CH$_3$)$_3$ |
| R-110 | CH(CH$_3$)$_2$ | C(CH$_3$)$_3$ |
| R-111 | C(CH$_3$)$_3$ | C(CH$_3$)$_3$ |
| R-112 | CH$_2$-phenyl | C(CH$_3$)$_3$ |
| R-113 | CH$_2$-cyclopropyl | C(CH$_3$)$_3$ |
| R-114 | CF$_3$ | C(CH$_3$)$_3$ |
| R-115 | CHF$_2$ | C(CH$_3$)$_3$ |
| R-116 | CH$_2$—CH=CH$_2$ | C(CH$_3$)$_3$ |
| R-117 | CH$_2$—C≡CH | C(CH$_3$)$_3$ |
| R-118 | H | CH$_2$-phenyl |
| R-119 | CH$_3$ | CH$_2$-phenyl |
| R-120 | CH$_2$CH$_3$ | CH$_2$-phenyl |
| R-121 | CH$_2$CH$_2$CH$_3$ | CH$_2$-phenyl |
| R-122 | CH$_2$CH$_2$CH$_2$CH$_3$ | CH$_2$-phenyl |
| R-123 | CH(CH$_3$)$_2$ | CH$_2$-phenyl |
| R-124 | C(CH$_3$)$_3$ | CH$_2$-phenyl |
| R-125 | CH$_2$-phenyl | CH$_2$-phenyl |
| R-126 | CH$_2$-cyclopropyl | CH$_2$-phenyl |
| R-127 | CF$_3$ | CH$_2$-phenyl |
| R-128 | CHF$_2$ | CH$_2$-phenyl |
| R-129 | CH$_2$—CH=CH$_2$ | CH$_2$-phenyl |
| R-130 | CH$_2$—C≡CH | CH$_2$-phenyl |
| R-131 | H | CH$_2$-cyclopropyl |
| R-132 | CH$_3$ | CH$_2$-cyclopropyl |
| R-133 | CH$_2$CH$_3$ | CH$_2$-cyclopropyl |
| R-134 | CH$_2$CH$_2$CH$_3$ | CH$_2$-cyclopropyl |
| R-135 | CH$_2$CH$_2$CH$_2$CH$_3$ | CH$_2$-cyclopropyl |
| R-136 | CH(CH$_3$)$_2$ | CH$_2$-cyclopropyl |
| R-137 | C(CH$_3$)$_3$ | CH$_2$-cyclopropyl |
| R-138 | CH$_2$-phenyl | CH$_2$-cyclopropyl |
| R-139 | CH$_2$-cyclopropyl | CH$_2$-cyclopropyl |
| R-140 | CF$_3$ | CH$_2$-cyclopropyl |
| R-141 | CHF$_2$ | CH$_2$-cyclopropyl |
| R-142 | CH$_2$—CH=CH$_2$ | CH$_2$-cyclopropyl |
| R-143 | CH$_2$—C≡CH | CH$_2$-cyclopropyl |
| R-144 | H | CF$_3$ |
| R-145 | CH$_3$ | CF$_3$ |
| R-146 | CH$_2$CH$_3$ | CF$_3$ |
| R-147 | CH$_2$CH$_2$CH$_3$ | CF$_3$ |
| R-148 | CH$_2$CH$_2$CH$_2$CH$_3$ | CF$_3$ |
| R-149 | CH(CH$_3$)$_2$ | CF$_3$ |
| R-150 | C(CH$_3$)$_3$ | CF$_3$ |
| R-151 | CH$_2$-phenyl | CF$_3$ |
| R-152 | CH$_2$-cyclopropyl | CF$_3$ |
| R-153 | CF$_3$ | CF$_3$ |
| R-154 | CHF$_2$ | CF$_3$ |
| R-155 | CH$_2$—CH=CH$_2$ | CF$_3$ |
| R-156 | CH$_2$—C≡CH | CF$_3$ |
| R-157 | H | CH$_2$—CH=CH$_2$ |
| R-158 | CH$_3$ | CH$_2$—CH=CH$_2$ |
| R-159 | CH$_2$CH$_3$ | CH$_2$—CH=CH$_2$ |
| R-160 | CH$_2$CH$_2$CH$_3$ | CH$_2$—CH=CH$_2$ |
| R-161 | CH$_2$CH$_2$CH$_2$CH$_3$ | CH$_2$—CH=CH$_2$ |
| R-162 | CH(CH$_3$)$_2$ | CH$_2$—CH=CH$_2$ |
| R-163 | C(CH$_3$)$_3$ | CH$_2$—CH=CH$_2$ |
| R-164 | CH$_2$-phenyl | CH$_2$—CH=CH$_2$ |
| R-165 | CH$_2$-cyclopropyl | CH$_2$—CH=CH$_2$ |
| R-166 | CF$_3$ | CH$_2$—CH=CH$_2$ |
| R-167 | CHF$_2$ | CH$_2$—CH=CH$_2$ |
| R-168 | CH$_2$—CH=CH$_2$ | CH$_2$—CH=CH$_2$ |
| R-169 | CH$_2$—C≡CH | CH$_2$—CH=CH$_2$ |
| R-170 | H | N(CH$_3$)$_2$ |
| R-171 | CH$_3$ | N(CH$_3$)$_2$ |
| R-172 | CH$_2$CH$_3$ | N(CH$_3$)$_2$ |
| R-173 | CH$_2$CH$_2$CH$_3$ | N(CH$_3$)$_2$ |
| R-174 | CH$_2$CH$_2$CH$_2$CH$_3$ | N(CH$_3$)$_2$ |
| R-175 | CH(CH$_3$)$_2$ | N(CH$_3$)$_2$ |
| R-176 | C(CH$_3$)$_3$ | N(CH$_3$)$_2$ |
| R-177 | CH$_2$-phenyl | N(CH$_3$)$_2$ |
| R-178 | CH$_2$-cyclopropyl | N(CH$_3$)$_2$ |
| R-179 | CF$_3$ | N(CH$_3$)$_2$ |
| R-180 | CHF$_2$ | N(CH$_3$)$_2$ |
| R-181 | CH$_2$—CH=CH$_2$ | N(CH$_3$)$_2$ |
| R-182 | CH$_2$—C≡CH | N(CH$_3$)$_2$ |
| R-183 | H | phenyl |
| R-184 | CH$_3$ | phenyl |
| R-185 | CH$_2$CH$_3$ | phenyl |
| R-186 | CH$_2$CH$_2$CH$_3$ | phenyl |
| R-187 | CH$_2$CH$_2$CH$_2$CH$_3$ | phenyl |
| R-188 | CH(CH$_3$)$_2$ | phenyl |
| R-189 | C(CH$_3$)$_3$ | phenyl |

TABLE A-continued

| No. | R$^1$ | R$^2$ |
|---|---|---|
| R-190 | CH$_2$-phenyl | phenyl |
| R-191 | CH$_2$-cyclopropyl | phenyl |
| R-192 | CF$_3$ | phenyl |
| R-193 | CHF$_2$ | phenyl |
| R-194 | CH$_2$—CH=CH$_2$ | phenyl |
| R-195 | CH$_2$—C≡CH | phenyl |

A skilled person will readily understand that the preferences given in connection with compounds I apply also for formulae I.A.1 to 1.B.3.d as defined above.

Especially preferred compounds I are described in Tables 1 to 108 below.

Table 1: Compounds of formula I.A.1, wherein A is (A.1), R is hydrogen, and the meanings of R$^1$ and R$^2$ for each compound correspond to one line of table A.

Table 2: Compounds of formula I.A.1, wherein A is (A.1), R is methyl, and the meanings of R$^1$ and R$^2$ for each compound correspond to one line of table A.

Table 3: Compounds of formula I.A.2.a, wherein A is (A.1), R is hydrogen, and the meanings of R$^1$ and R$^2$ for each compound correspond to one line of table A.

Table 4: Compounds of formula I.A.2.a, wherein A is (A.1), R is methyl, and the meanings of R$^1$ and R$^2$ for each compound correspond to one line of table A.

Table 5: Compounds of formula I.A.2.b, wherein A is (A.1), R is hydrogen, and the meanings of R$^1$ and R$^2$ for each compound correspond to one line of table A.

Table 6: Compounds of formula I.A.2.b, wherein A is (A.1), R is methyl, and the meanings of R$^1$ and R$^2$ for each compound correspond to one line of table A.

Table 7: Compounds of formula I.A.2.c, wherein A is (A.1), R is hydrogen, and the meanings of R$^1$ and R$^2$ for each compound correspond to one line of table A.

Table 8: Compounds of formula I.A.2.c, wherein A is (A.1), R is methyl, and the meanings of R$^1$ and R$^2$ for each compound correspond to one line of table A.

Table 9: Compounds of formula I.A.2.d, wherein A is (A.1), R is hydrogen, and the meanings of R$^1$ and R$^2$ for each compound correspond to one line of table A.

Table 10: Compounds of formula I.A.2.d, wherein A is (A.1), R is methyl, and the meanings of R$^1$ and R$^2$ for each compound correspond to one line of table A.

Table 11: Compounds of formula I.A.3.a, wherein A is (A.1), R is hydrogen, and the meanings of R$^1$ and R$^2$ for each compound correspond to one line of table A.

Table 12: Compounds of formula I.A.3.a, wherein A is (A.1), R is methyl, and the meanings of R$^1$ and R$^2$ for each compound correspond to one line of table A.

Table 13: Compounds of formula I.A.3.b, wherein A is (A.1), R is hydrogen, and the meanings of R$^1$ and R$^2$ for each compound correspond to one line of table A.

Table 14: Compounds of formula I.A.3.b, wherein A is (A.1), R is methyl, and the meanings of R$^1$ and R$^2$ for each compound correspond to one line of table A.

Table 15: Compounds of formula I.A.3.c, wherein A is (A.1), R is hydrogen, and the meanings of R$^1$ and R$^2$ for each compound correspond to one line of table A.

Table 16: Compounds of formula I.A.3.c, wherein A is (A.1), R is methyl, and the meanings of R$^1$ and R$^2$ for each compound correspond to one line of table A.

Table 17: Compounds of formula I.A.3.d, wherein A is (A.1), R is hydrogen, and the meanings of R$^1$ and R$^2$ for each compound correspond to one line of table A.

Table 18: Compounds of formula I.A.3.d, wherein A is (A.1), R is methyl, and the meanings of R$^1$ and R$^2$ for each compound correspond to one line of table A.

Table 19: Compounds of formula I.A.1, wherein A is (A.2), R is hydrogen, and the meanings of R$^1$ and R$^2$ for each compound correspond to one line of table A.

Table 20: Compounds of formula I.A.1, wherein A is (A.2), R is methyl, and the meanings of R$^1$ and R$^2$ for each compound correspond to one line of table A.

Table 21: Compounds of formula I.A.2.a, wherein A is (A.2), R is hydrogen, and the meanings of R$^1$ and R$^2$ for each compound correspond to one line of table A.

Table 22: Compounds of formula I.A.2.a, wherein A is (A.2), R is methyl, and the meanings of R$^1$ and R$^2$ for each compound correspond to one line of table A.

Table 23: Compounds of formula I.A.2.b, wherein A is (A.2), R is hydrogen, and the meanings of R$^1$ and R$^2$ for each compound correspond to one line of table A.

Table 24: Compounds of formula I.A.2.b, wherein A is (A.2), R is methyl, and the meanings of R$^1$ and R$^2$ for each compound correspond to one line of table A.

Table 25: Compounds of formula I.A.2.c, wherein A is (A.2), R is hydrogen, and the meanings of R$^1$ and R$^2$ for each compound correspond to one line of table A.

Table 26: Compounds of formula I.A.2.c, wherein A is (A.2), R is methyl, and the meanings of R$^1$ and R$^2$ for each compound correspond to one line of table A.

Table 27: Compounds of formula I.A.2.d, wherein A is (A.2), R is hydrogen, and the meanings of R$^1$ and R$^2$ for each compound correspond to one line of table A.

Table 28: Compounds of formula I.A.2.d, wherein A is (A.2), R is methyl, and the meanings of R$^1$ and R$^2$ for each compound correspond to one line of table A.

Table 29: Compounds of formula I.A.3.a, wherein A is (A.2), R is hydrogen, and the meanings of R$^1$ and R$^2$ for each compound correspond to one line of table A.

Table 30: Compounds of formula I.A.3.a, wherein A is (A.2), R is methyl, and the meanings of R$^1$ and R$^2$ for each compound correspond to one line of table A.

Table 31: Compounds of formula I.A.3.b, wherein A is (A.2), R is hydrogen, and the meanings of R$^1$ and R$^2$ for each compound correspond to one line of table A.

Table 32: Compounds of formula I.A.3.b, wherein A is (A.2), R is methyl, and the meanings of R$^1$ and R$^2$ for each compound correspond to one line of table A.

Table 33: Compounds of formula I.A.3.c, wherein A is (A.2), R is hydrogen, and the meanings of R$^1$ and R$^2$ for each compound correspond to one line of table A.

Table 34: Compounds of formula I.A.3.c, wherein A is (A.2), R is methyl, and the meanings of R$^1$ and R$^2$ for each compound correspond to one line of table A.

Table 35: Compounds of formula I.A.3.d, wherein A is (A.2), R is hydrogen, and the meanings of R$^1$ and R$^2$ for each compound correspond to one line of table A.

Table 36: Compounds of formula I.A.3.d, wherein A is (A.2), R is methyl, and the meanings of R$^1$ and R$^2$ for each compound correspond to one line of table A.

Table 37: Compounds of formula I.A.1, wherein A is (A.3), R is hydrogen, and the meanings of R$^1$ and R$^2$ for each compound correspond to one line of table A.

Table 38: Compounds of formula I.A.1, wherein A is (A.3), R is methyl, and the meanings of R$^1$ and R$^2$ for each compound correspond to one line of table A.

Table 39: Compounds of formula I.A.2.a, wherein A is (A.3), R is hydrogen, and the meanings of R$^1$ and R$^2$ for each compound correspond to one line of table A.

Table 40: Compounds of formula I.A.2.a, wherein A is (A.3), R is methyl, and the meanings of $R^1$ and $R^2$ for each compound correspond to one line of table A.

Table 41: Compounds of formula I.A.2.b, wherein A is (A.3), R is hydrogen, and the meanings of $R^1$ and $R^2$ for each compound correspond to one line of table A.

Table 42: Compounds of formula I.A.2.b, wherein A is (A.3), R is methyl, and the meanings of $R^1$ and $R^2$ for each compound correspond to one line of table A.

Table 43: Compounds of formula I.A.2.c, wherein A is (A.3), R is hydrogen, and the meanings of $R^1$ and $R^2$ for each compound correspond to one line of table A.

Table 44: Compounds of formula I.A.2.c, wherein A is (A.3), R is methyl, and the meanings of $R^1$ and $R^2$ for each compound correspond to one line of table A.

Table 45: Compounds of formula I.A.2.d, wherein A is (A.3), R is hydrogen, and the meanings of $R^1$ and $R^2$ for each compound correspond to one line of table A.

Table 46: Compounds of formula I.A.2.d, wherein A is (A.3), R is methyl, and the meanings of $R^1$ and $R^2$ for each compound correspond to one line of table A.

Table 47: Compounds of formula I.A.3.a, wherein A is (A.3), R is hydrogen, and the meanings of $R^1$ and $R^2$ for each compound correspond to one line of table A.

Table 48: Compounds of formula I.A.3.a, wherein A is (A.3), R is methyl, and the meanings of $R^1$ and $R^2$ for each compound correspond to one line of table A.

Table 49: Compounds of formula I.A.3.b, wherein A is (A.3), R is hydrogen, and the meanings of $R^1$ and $R^2$ for each compound correspond to one line of table A.

Table 50: Compounds of formula I.A.3.b, wherein A is (A.3), R is methyl, and the meanings of $R^1$ and $R^2$ for each compound correspond to one line of table A.

Table 51: Compounds of formula I.A.3.c, wherein A is (A.3), R is hydrogen, and the meanings of $R^1$ and $R^2$ for each compound correspond to one line of table A.

Table 52: Compounds of formula I.A.3.c, wherein A is (A.3), R is methyl, and the meanings of $R^1$ and $R^2$ for each compound correspond to one line of table A.

Table 53: Compounds of formula I.A.3.d, wherein A is (A.3), R is hydrogen, and the meanings of $R^1$ and $R^2$ for each compound correspond to one line of table A.

Table 54: Compounds of formula I.A.3.d, wherein A is (A.3), R is methyl, and the meanings of $R^1$ and $R^2$ for each compound correspond to one line of table A.

Table 55: Compounds of formula I.B.1, wherein A is (A.1), R is hydrogen, and the meanings of $R^1$ and $R^2$ for each compound correspond to one line of table A.

Table 56: Compounds of formula I.B.1, wherein A is (A.1), R is methyl, and the meanings of $R^1$ and $R^2$ for each compound correspond to one line of table A.

Table 57: Compounds of formula I.B.2.a, wherein A is (A.1), R is hydrogen, and the meanings of $R^1$ and $R^2$ for each compound correspond to one line of table A.

Table 58: Compounds of formula I.B.2.a, wherein A is (A.1), R is methyl, and the meanings of $R^1$ and $R^2$ for each compound correspond to one line of table A.

Table 59: Compounds of formula I.B.2.b, wherein A is (A.1), R is hydrogen, and the meanings of $R^1$ and $R^2$ for each compound correspond to one line of table A.

Table 60: Compounds of formula I.B.2.b, wherein A is (A.1), R is methyl, and the meanings of $R^1$ and $R^2$ for each compound correspond to one line of table A.

Table 61: Compounds of formula I.B.2.c, wherein A is (A.1), R is hydrogen, and the meanings of $R^1$ and $R^2$ for each compound correspond to one line of table A.

Table 62: Compounds of formula I.B.2.c, wherein A is (A.1), R is methyl, and the meanings of $R^1$ and $R^2$ for each compound correspond to one line of table A.

Table 63: Compounds of formula I.B.2.d, wherein A is (A.1), R is hydrogen, and the meanings of $R^1$ and $R^2$ for each compound correspond to one line of table A.

Table 64: Compounds of formula I.B.2.d, wherein A is (A.1), R is methyl, and the meanings of $R^1$ and $R^2$ for each compound correspond to one line of table A.

Table 65: Compounds of formula I.B.3.a, wherein A is (A.1), R is hydrogen, and the meanings of $R^1$ and $R^2$ for each compound correspond to one line of table A.

Table 66: Compounds of formula I.B.3.a, wherein A is (A.1), R is methyl, and the meanings of $R^1$ and $R^2$ for each compound correspond to one line of table A.

Table 67: Compounds of formula I.B.3.b, wherein A is (A.1), R is hydrogen, and the meanings of $R^1$ and $R^2$ for each compound correspond to one line of table A.

Table 68: Compounds of formula I.B.3.b, wherein A is (A.1), R is methyl, and the meanings of $R^1$ and $R^2$ for each compound correspond to one line of table A.

Table 69: Compounds of formula I.B.3.c, wherein A is (A.1), R is hydrogen, and the meanings of $R^1$ and $R^2$ for each compound correspond to one line of table A.

Table 70: Compounds of formula I.B.3.c, wherein A is (A.1), R is methyl, and the meanings of $R^1$ and $R^2$ for each compound correspond to one line of table A.

Table 71: Compounds of formula I.B.3.d, wherein A is (A.1), R is hydrogen, and the meanings of $R^1$ and $R^2$ for each compound correspond to one line of table A.

Table 72: Compounds of formula I.B.3.d, wherein A is (A.1), R is methyl, and the meanings of $R^1$ and $R^2$ for each compound correspond to one line of table A.

Table 73: Compounds of formula I.B.1, wherein A is (A.2), R is hydrogen, and the meanings of $R^1$ and $R^2$ for each compound correspond to one line of table A.

Table 74: Compounds of formula I.B.1, wherein A is (A.2), R is methyl, and the meanings of $R^1$ and $R^2$ for each compound correspond to one line of table A.

Table 75: Compounds of formula I.B.2.a, wherein A is (A.2), R is hydrogen, and the meanings of $R^1$ and $R^2$ for each compound correspond to one line of table A.

Table 76: Compounds of formula I.B.2.a, wherein A is (A.2), R is methyl, and the meanings of $R^1$ and $R^2$ for each compound correspond to one line of table A.

Table 77: Compounds of formula I.B.2.b, wherein A is (A.2), R is hydrogen, and the meanings of $R^1$ and $R^2$ for each compound correspond to one line of table A.

Table 78: Compounds of formula I.B.2.b, wherein A is (A.2), R is methyl, and the meanings of $R^1$ and $R^2$ for each compound correspond to one line of table A.

Table 79: Compounds of formula I.B.2.c, wherein A is (A.2), R is hydrogen, and the meanings of $R^1$ and $R^2$ for each compound correspond to one line of table A.

Table 80: Compounds of formula I.B.2.c, wherein A is (A.2), R is methyl, and the meanings of $R^1$ and $R^2$ for each compound correspond to one line of table A.

Table 81: Compounds of formula I.B.2.d, wherein A is (A.2), R is hydrogen, and the meanings of $R^1$ and $R^2$ for each compound correspond to one line of table A.

Table 82: Compounds of formula I.B.2.d, wherein A is (A.2), R is methyl, and the meanings of $R^1$ and $R^2$ for each compound correspond to one line of table A.

Table 83: Compounds of formula I.B.3.a, wherein A is (A.2), R is hydrogen, and the meanings of $R^1$ and $R^2$ for each compound correspond to one line of table A.

Table 84: Compounds of formula I.B.3.a, wherein A is (A.2), R is methyl, and the meanings of $R^1$ and $R^2$ for each compound correspond to one line of table A.

Table 85: Compounds of formula I.B.3.b, wherein A is (A.2), R is hydrogen, and the meanings of $R^1$ and $R^2$ for each compound correspond to one line of table A.

Table 86: Compounds of formula I.B.3.b, wherein A is (A.2), R is methyl, and the meanings of $R^1$ and $R^2$ for each compound correspond to one line of table A.

Table 87: Compounds of formula I.B.3.c, wherein A is (A.2), R is hydrogen, and the meanings of $R^1$ and $R^2$ for each compound correspond to one line of table A.

Table 88: Compounds of formula I.B.3.c, wherein A is (A.2), R is methyl, and the meanings of $R^1$ and $R^2$ for each compound correspond to one line of table A.

Table 89: Compounds of formula I.B.3.d, wherein A is (A.2), R is hydrogen, and the meanings of $R^1$ and $R^2$ for each compound correspond to one line of table A.

Table 90: Compounds of formula I.B.3.d, wherein A is (A.2), R is methyl, and the meanings of $R^1$ and $R^2$ for each compound correspond to one line of table A.

Table 91: Compounds of formula I.B.1, wherein A is (A.3), R is hydrogen, and the meanings of $R^1$ and $R^2$ for each compound correspond to one line of table A.

Table 92: Compounds of formula I.B.1, wherein A is (A.3), R is methyl, and the meanings of $R^1$ and $R^2$ for each compound correspond to one line of table A.

Table 93: Compounds of formula I.B.2.a, wherein A is (A.3), R is hydrogen, and the meanings of $R^1$ and $R^2$ for each compound correspond to one line of table A.

Table 94: Compounds of formula I.B.2.a, wherein A is (A.3), R is methyl, and the meanings of $R^1$ and $R^2$ for each compound correspond to one line of table A.

Table 95: Compounds of formula I.B.2.b, wherein A is (A.3), R is hydrogen, and the meanings of $R^1$ and $R^2$ for each compound correspond to one line of table A.

Table 96: Compounds of formula I.B.2.b, wherein A is (A.3), R is methyl, and the meanings of $R^1$ and $R^2$ for each compound correspond to one line of table A.

Table 97: Compounds of formula I.B.2.c, wherein A is (A.3), R is hydrogen, and the meanings of $R^1$ and $R^2$ for each compound correspond to one line of table A.

Table 98: Compounds of formula I.B.2.c, wherein A is (A.3), R is methyl, and the meanings of $R^1$ and $R^2$ for each compound correspond to one line of table A.

Table 99: Compounds of formula I.B.2.d, wherein A is (A.3), R is hydrogen, and the meanings of $R^1$ and $R^2$ for each compound correspond to one line of table A.

Table 100: Compounds of formula I.B.2.d, wherein A is (A.3), R is methyl, and the meanings of $R^1$ and $R^2$ for each compound correspond to one line of table A.

Table 101: Compounds of formula I.B.3.a, wherein A is (A.3), R is hydrogen, and the meanings of $R^1$ and $R^2$ for each compound correspond to one line of table A.

Table 102: Compounds of formula I.B.3.a, wherein A is (A.3), R is methyl, and the meanings of $R^1$ and $R^2$ for each compound correspond to one line of table A.

Table 103: Compounds of formula I.B.3.b, wherein A is (A.3), R is hydrogen, and the meanings of $R^1$ and $R^2$ for each compound correspond to one line of table A.

Table 104: Compounds of formula I.B.3.b, wherein A is (A.3), R is methyl, and the meanings of $R^1$ and $R^2$ for each compound correspond to one line of table A.

Table 105: Compounds of formula I.B.3.c, wherein A is (A.3), R is hydrogen, and the meanings of $R^1$ and $R^2$ for each compound correspond to one line of table A.

Table 106: Compounds of formula I.B.3.c, wherein A is (A.3), R is methyl, and the meanings of $R^1$ and $R^2$ for each compound correspond to one line of table A.

Table 107: Compounds of formula I.B.3.d, wherein A is (A.3), R is hydrogen, and the meanings of $R^1$ and $R^2$ for each compound correspond to one line of table A.

Table 108: Compounds of formula I.B.3.d, wherein A is (A.3), R is methyl, and the meanings of $R^1$ and $R^2$ for each compound correspond to one line of table A.

A person skilled in the art will realize that compounds I can be prepared by reacting compounds of formula II with the appropriate O-alkylhydroxylamine (or a salt hereof) in an organic solvent, preferably an alcoholic solvent. If a salt is used, it may be preferred to add a base, preferably an organic amine. The reaction is preferably performed at temperatures between 0 and 80° C., even more preferably at about 25° C.

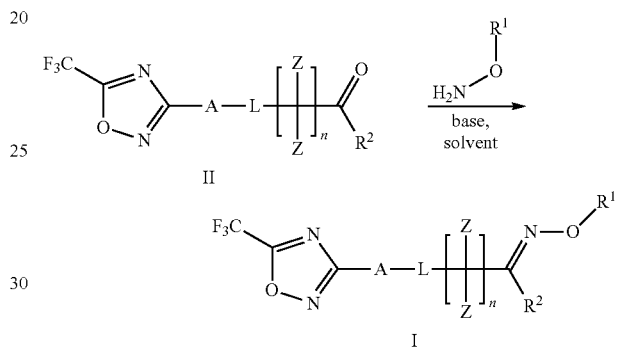

A preferred procedure to access compounds II may involve treatment of a solution of compounds III in an organic solvent (preferably a halocarbon) with a suitable oxidizing agent, if required at elevated temperatures. Preference can be given to pyridinium chlorochromate (PCC, as precessed e.g. in Bioorganic & Medicinal Chemistry, 16(2), 981-994; 2008), Dess-Martin periodinane (DMP, see for example WO 2008/149834), or Swern's conditions as described e.g. in WO 2006/018104.

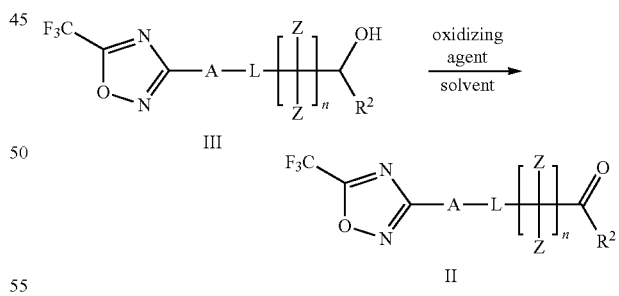

Alcohols of formula III wherein X is O can be prepared following methods that have been previously described and that are outlined below:

In case L is #-C(=O)—NR—, amino alcohols of formula V can be reacted with acid chlorides of formula IV resulting in the exclusive formation of compounds IIIa (see e.g. Journal of Organic Chemistry, 76(16), 6749-6767; 2011; Journal of the American Chemical Society, 75, 5896-7; 1953). It may be preferred to perform the reaction at temperatures between −20 and 40° C., more preferably at about 25° C. in an organic solvent such as a halocarbon in the presence of a base, preferably an amine, more preferably a sterically encumbered tertiary amine. The required amino alcohols V are commercially available or can be prepared by a skilled person following established procedures.

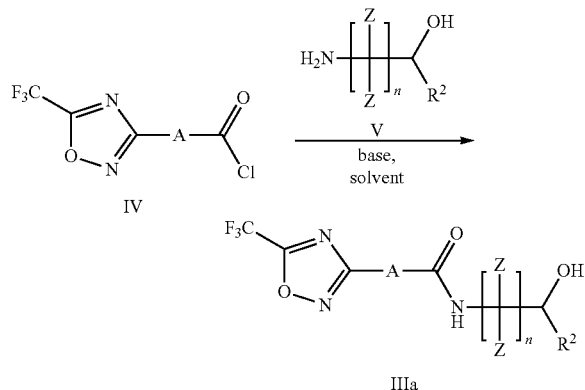

Compounds IV may be accessed by reacting carboxylic acids of formula VI with an appropriate chlorinating agent, preferably thionyl chloride, either neat or in an organic solvent, preferably a non-polar hydrocarbon or a halocarbon. The reaction is best performed at elevated temperatures, preferably in the range of 40-100° C.

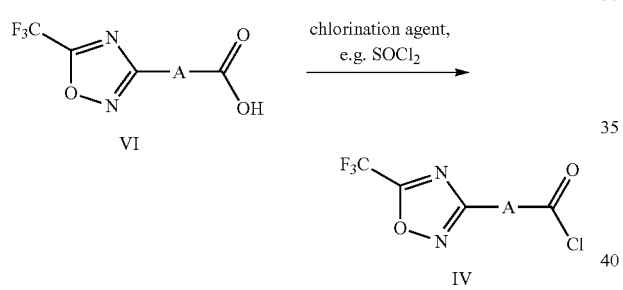

Compounds VI can be prepared by reacting amidines of formula VII with trifluoroacetic anhydride in an organic solvent, e.g. dichloromethane, or THF at temperatures between 0° C. and 100° C., preferably at about 25° C., as previously described in WO 2013/008162.

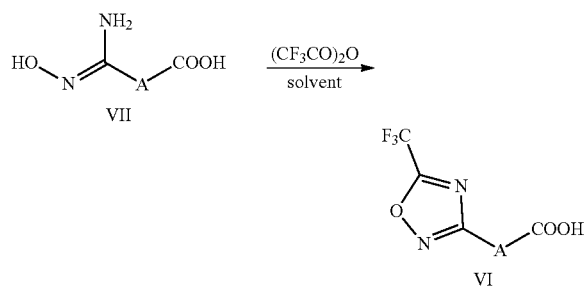

Compounds VII can be accessed by reacting nitrile compounds VIII with hydroxylamine (or its HCl salt) in an organic solvent and in the presence of a base (for precedents see for example WO 2009/074950, WO 2006/013104, EP1932843). Preferably, an alcoholic solvent and an inorganic base are used, most preferably ethanol and potassium carbonate. If appropriate, water may be added to enhance solubility of the reactants. The reaction is best performed at elevated temperatures, most preferably in the range between 60 and 80° C.

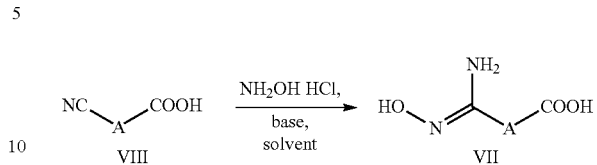

Compounds VIII are either commercially available, or can be accessed from suitable starting materials by methods that are known to a person skilled in the art.

In case L is #-NR—C(=O)—, compounds IIIb can be accessed by reacting compounds IX with compounds X in the presence of a suitable coupling agent. Examples for coupling agents include DCC (as referenced e.g. in Natural Product Communications, 8(7), 889-896; 2013), EDCl/HOBt (e.g. US 2009/0118284) and BOP-Cl (e.g. Tetrahedron Letters, 42(2), 285-287; 2001). The reaction is best performed in an organic solvent, preferably a halocarbon (more preferably haloalkane), and if required in the presence of a base. Carboxylic acids of formula X are typically commercially available or can be prepared by a skilled person following established procedures.

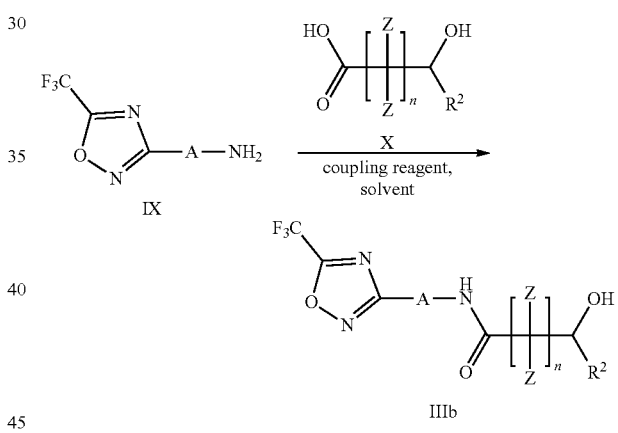

Compounds IX can be prepared by selective reduction of nitro compounds XI. Suitable reduction conditions were described for example in Organic Letters 2013, 15(13), 3362-3365; European Journal of Organic Chemistry 2013, 2013(6), 1158-1169 or in Angewandte Chemie, International Edition 2014, 53(52), 14559-14563.

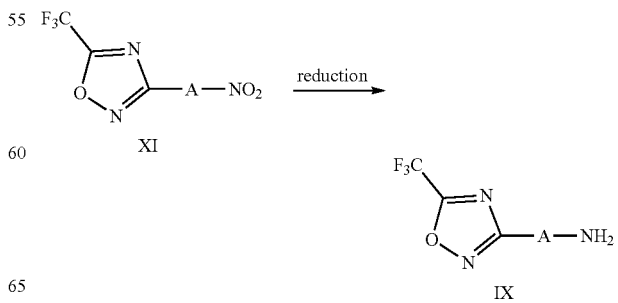

To access compounds XI, it may be preferred to react amidines XII with trifluoroacetic anhydride in an organic solvent, for example but not limited to dichloromethane or THF at temperatures between 0° C. and 100° C., preferably at room temperature, as previously described in WO 2013/008162.

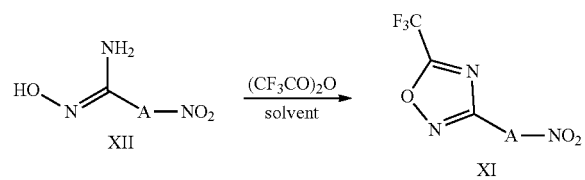

Compounds XII can be accessed by reacting nitrile compounds XIII with hydroxylamine (or its hydrochloride salt) in an organic solvent and in the presence of a base (for precedents see for example WO 2009/074950, WO 2006/013104, EP1932843). Preferably, an alcoholic solvent and an inorganic base are used, most preferably ethanol and potassium carbonate. If appropriate, water may be added to enhance the solubility of the reactants. The reaction is best performed at elevated temperatures, preferably in the range between 60 and 80° C.

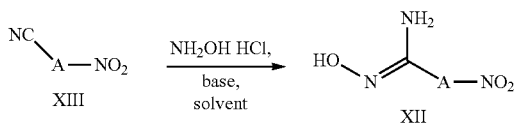

Compounds XIII are either commercially available, or can be accessed from suitable starting materials by methods that are obvious to a person skilled in the art.

If appropriate, compounds I wherein X is O can be transformed to compounds I wherein X is S by reacting compounds I wherein X is O with a suitable sulfur source, such as for example Lawesson's reagent (previously described e.g. in WO 2014/028589 or Journal of Organic Chemistry, 76(8), 2828-2839; 2011) or $P_2S_5$ as referenced e.g. in Bioorganic & Medicinal Chemistry Letters, 18(9), 2939-2943; 2008.

The compounds of the formula I or compositions comprising said compounds according to the invention and the mixtures comprising said compounds and compositions, respectively, are suitable as fungicides. They are distinguished by an outstanding effectiveness against a broad spectrum of phytopathogenic fungi, including soil-borne fungi, which derive especially from the following classes or are closely related to any of them: Ascomycota (Ascomycetes), for example, but not limited to the genus *Cochliobolus, Colletotrichum, Fusarium, Microdochium, Penicillium, Phoma, Magnaporte, Zymoseptoria,* and *Pseudocercosporella; Basdiomycota* (Basidiomycetes), for example, but not limited to the genus *Phakospora, Puccinia, Rhizoctonia, Sphacelotheca, Tilletia, Typhula,* and *Ustilago; Chytridiomycota* (Chytridiomycetes), for example, but not limited to the genus *Chytridiales,* and *Synchytrium; Deuteromycetes* (syn. Fungi imperfecti), for example, but not limited to the genus *Ascochyta, Diplodia, Erysiphe, Fusarium, Phomopsis,* and *Pyrenophora*; Peronosporomycetes (syn. Oomycetes), for example but not limited to the genus *Peronospora, Pythium, Phytophthora*; Plasmodiophoromycetes, for example but not limited to the genus *Plasmodiophora; Zygomycetes,* for example, but not limited to the genus *Rhizopus.*

Some of the compounds of the formula I and the compositions according to the invention are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called *Stevia*); natural rubber plants or ornamental and forestry plants, such as flowers, shrubs, broad-leaved trees or evergreens, e. g. conifers; and on the plant propagation material, such as seeds, and the crop material of these plants. Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties. Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme phosphinothricin-N-acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme). Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the Mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The compounds I and compositions thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e. g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvurr.* leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola.*: Anthracnose stalk rot), soft fruits, potatoes (e. g. *C. coccodes*: black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*. Black Foot Disease) and ornamentals; *Dematophora* (teleomorph: *Rosellinia*) necatrix (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitiporia* (syn. *Phellinus*) *punctata, F. mediterranea, Phaeomoniella chlamydospora* (earlier *Phaeoacremonium chlamydosporum*), *Phaeoacremonium aleophilum* and/or *Botryosphaeria obtusa; Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and *F. brasiliense* each causing sudden death syndrome on soybeans, and *F. verticilioides* on corn; *Gaeumannomyces graminis* (take-all) on cereals (e. g. wheat or barley) and corn; *Gibberella* spp. on cereals (e. g. *G. zeae*) and rice (e. g. *G. fujikuror*. Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritic, Septoria* blotch) on wheat or *M. fijensis* (black Sigatoka disease) on bananas; *Peronospora* spp. (downy mildew) on cabbage (e. g. *P. brassicae*), rape (e. g. *P. parastica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseol*, teleomorph: *Diaporthe phaseolorum*); *Physoderma maydis* (brown spots) on corn; *Phytophthora* spp. (wilt, root, leaf, fruit and stem rot) on various plants, such as paprika and cucurbits (e. g. *P. capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstediion* sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. gram/n/s*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humilion* hop; *Pseudopezicula tracheiphila* (red fire disease or, rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii*(orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni*(*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani*(root and stem rot) on soybeans, *R. solani*(sheath blight) on rice or *R. cerealis* (*Rhizoctonia* spring blight) on wheat or barley; *Rhizopus stolonifer*(black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici*(*Septoria* blotch) on wheat and S. (syn. *Stagonospora*) *nodorum* (*Stagonospora* blotch) on cereals; *Uncinula* (syn. *Erysiphe*) necator (powdery mildew, anamorph: *Oidium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina*spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici*(syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseol*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillum* spp. (wilt) on various plants, such as fruits and ornamentals, vines, soft fruits, vegetables and field crops, e. g. *V. dahliae* on strawberries, rape, potatoes and tomatoes.

In a preferred embodiment the compounds I and compositions thereof, respectively, are particularly suitable for controlling the following plant diseases: *Puccinia* spp. (rusts) on various plants, for example, but not limited to *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye and *Phakopsoraceae* spp. on various plants, in particular *Phakopsora pachyrhizi* and *P. meibomiae* (soybean rust) on soybeans.

The compounds I and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pulluans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., *Deuteromycetes* such as *Aspergillus* spp., *Cladosporium* spp., *Penicillium* spp., *Trichoderma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof. Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof. Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e. g. in red, blue, or green) are pigments of low water solubility and water-soluble dyes. Examples are inorganic colorants (e. g. iron oxide, titan oxide, iron hexacyanoferrate) and organic colorants (e. g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:
i) Water-soluble concentrates (SL, LS)
10-60 wt % of a compound I and 5-15 wt % wetting agent (e. g. alcohol alkoxylates) are dissolved in water and/or in a water-soluble solvent (e. g. alcohols) ad 100 wt %. The active substance dissolves upon dilution with water.

ii) Dispersible concentrates (DC)

5-25 wt % of a compound I and 1-10 wt % dispersant (e. g. polyvinyl pyrrolidone) are dissolved in organic solvent (e. g. cyclohexanone) ad 100 wt %. Dilution with water gives a dispersion.

iii) Emulsifiable concentrates (EC)

15-70 wt % of a compound I and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.

iv) Emulsions (EW, EO, ES)

5-40 wt % of a compound I and 1-10 wt % emulsifiers (e. g. calcium dodecylbenzenesulfonate and castor oil ethoxylate) are dissolved in 20-40 wt % water-insoluble organic solvent (e. g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I are comminuted with addition of 2-10 wt % dispersants and wetting agents (e. g. sodium lignosulfonate and alcohol ethoxylate), 0.1-2 wt % thickener (e. g. xanthan gum) and water ad 100 wt % to give a fine active substance suspension. Dilution with water gives a stable suspension of the active substance. For FS type composition up to 40 wt % binder (e. g. polyvinyl alcohol) is added.

vi) Water-dispersible granules and water-soluble granules (WG, SG)

50-80 wt % of a compound I are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-dispersible powders and water-soluble powders (WP, SP, WS) 50-80 wt % of a compound I are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.

viii) Gel (GW, GF)

In an agitated ball mill, 5-25 wt % of a compound I are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

ix) Microemulsion (ME)

5-20 wt % of a compound I are added to 5-30 wt % organic solvent blend (e. g. fatty acid dimethyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound I, 0-40 wt % water insoluble organic solvent (e. g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization results in the formation of poly(meth)acrylate microcapsules. Alternatively, an oil phase comprising 5-50 wt % of a compound I according to the invention, 0-40 wt % water insoluble organic solvent (e. g. aromatic hydrocarbon), and an isocyanate monomer (e. g. diphenylmethene-4,4'-diisocyanatae) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

xi) Dustable powders (DP, DS)

1-10 wt % of a compound I are ground finely and mixed intimately with solid carrier (e. g. finely divided kaolin) ad 100 wt %.

xii) Granules (GR, FG)

0.5-30 wt % of a compound I is ground finely and associated with solid carrier (e. g. silicate) ad 100 wt %. Granulation is achieved by extrusion, spray-drying or fluidized bed.

xiii) Ultra-low volume liquids (UL)

1-50 wt % of a compound I are dissolved in organic solvent (e. g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, more preferably between 1 and 70%, and in particular between 10 and 60%, by weight of active substance. The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, onto plant propagation material, especially seeds, include dressing, coating, pelleting, dusting, and soaking as well as in-furrow application methods. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

A pesticide is generally a chemical or biological agent (such as pestidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of pesticides II (e. g. pesticidally-active substances and biopesticides), in conjunction with which the compounds I can be used, is intended to illustrate the possible combinations but does not limit them:

A) Respiration inhibitors: Inhibitors of complex III at $Q_o$ site: azoxystrobin (A.1.1), coumeth-oxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxy-strobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate (A.1.22), 1-[3-chloro-2-[[1-(4-chlorophenyl)-1H-pyrazol-3-yl]oxymethyl]phenyl]-4-methyl-tetrazol-5-one (A.1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl tetra-zol-5-one (A.1.25), 1-[2-[[1-(4-chlorophenyl)pyrazol-3-yl]oxymethyl]-3-fluoro-phenyl]-4-methyl-tetrazol-5-one (A.1.26), 1-[2-[[1-(2,4-dichlorophenyl)pyrazol-3-yl]oxymethyl]-3-fluoro-phenyl]-4-methyl-tetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolyl)thiazol-2-yl]oxymethyl]phenyl]-4-methyl-tetrazol-5-one (A. 1.29), 1-[3-cyclopropyl-2-[[2-methyl-4-(1-methylpyrazol-3-yl)phenoxy]-methyl]phenyl]-4-methyl-tetrazol-5-one (A. 1.30), 1-[3-(difluoromethoxy)-2-[[2-methyl-4-(1-methyl pyrazol-3-yl) phenoxy]methyl]phenyl]-4-methyl-tetrazol-5-one (A.1.31), 1-methyl-4-[3-methyl-2-[[2-methyl-4-(1-methylpyrazol-3-yl)phenoxy]methyl]phenyl]tetrazol-5-one (A.1.32), 1-methyl-4-[3-methyl-2-[[1-[3-(trifluoromethyl)phenyl]-ethylideneamino]oxymethyl]phenyl]tetrazol-5-one (A.1.33), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), pyriminostrobin (A.1.36), bifujunzhi (A.1.37), 2-(ortho-((2, 5-dimethylphenyl-oxymethylen)phenyl)-3-methoxy-acrylic acid methylester (A.1.38).

Inhibitors of complex III at Qi site: cyazofamid (A.2.1), amisulbrom (A.2.2), [(6S,7R,8R)-8-benzyl-3-[(3-hydroxy-4-methoxy-pyridine-2-carbonyl)amino]-6-methyl-4,9-dioxo-1,5-dioxonan-7-yl] 2-methylpropanoate (A.2.3), [2-[[(7R,8R,9S)-7-benzyl-9-methyl-8-(2-methylpropanoyloxy)-2,6-dioxo-1,5-dioxonan-3-yl] carbamoyl]-4-methoxy-3-pyridyl]oxymethyl 2-methylpropanoate (A.2.4), [(6S,7R,8R)-8-benzyl-3-[[4-methoxy-3-(propanoyloxy-methoxy)pyridine-2-carbonyl] amino]-6-methyl-4,9-dioxo-1,5-dioxonan-7-yl] 2-methylpropanoate (A.2.5).

Inhibitors of complex II: benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.15), penthiopyrad (A.3.16), 3-(difluoromethyl)-N-methoxy-1-methyl-N-[1-methyl-2-(2,4,6-trichlorophenyl)ethyl]pyrazole-4-carboxamide (A.3.17), N-[2-(3,4-difluorophenyl)phenyl]-3-(trifluoromethyl)pyrazine-2-carboxamide (A.3.18), sedaxane (A.3.19), tecloftalam (A.3.20), thifluzamide (A.3.21), 3-(difluoromethyl)-1-methyl-N-(1,1,3-trimethylindan-4-yl)pyrazole-4-carboxamide (A.3.22), 3-(trifluoromethyl)-1-methyl-N-(1,1,3-trimethylindan-4-yl)pyrazole-4-carboxamide (A.3.23), 1,3-dimethyl-N-(1,1,3-trimethylindan-4-yl)pyrazole-4-carboxamide (A.3.24), 3-(trifluoromethyl)-1,5-dimethyl-N-(1,1,3-trimethylindan-4-yl)pyrazole-4-carboxamide (A.3.25), 1,3,5-trimethyl-N-(1,1,3-trimethylindan-4-yl)

pyrazole-4-carboxamide (A.3.26), 3-(difluoromethyl)-1,5-dimethyl-N-(1,1,3-trimethylindan-4-yl)pyrazole-4-carboxamide (A.3.27), 3-(difluoromethyl)-N-(7-fluoro-1,1,3-trimethyl-indan-4-yl)-1-methyl-pyrazole-4-carboxamide (A.3.28), methyl (E)-2-[2-[(5-cyano-2-methyl-phenoxy)methyl]phenyl]-3-methoxy-prop-2-enoate (A.3.30), N-[(5-chloro-2-isopropyl-phenyl)methyl]-N-cyclopropyl-3-(difluoromethyl)-5 fluoro-1-methyl-pyrazole-4-carboxamide (A.3.31), 2-(difluoromethyl)-N-(1,1,3-trimethyl-indan-4-yl)pyridine-3-carboxamide (A.3.32), 2-(difluoromethyl)-N-[(3R)-1,1,3-trimethylindan-4-yl]pyridine-3-carboxamide (A.3.33), 2-(difluoromethyl)-N-(3-ethyl-1,1-dimethyl-indan-4-yl)-pyridine-3-carboxamide (A.3.34), 2-(difluoromethyl)-N-[(3R)-3-ethyl-1,1-dimethyl-indan-4-yl]-pyridine-3-carboxamide (A.3.35), 2-(difluoromethyl)-N-(1,1-dimethyl-3-propyl-indan-4-yl)-py-ridine-3-carboxamide (A.3.36), 2-(difluoromethyl)-N-[(3R)-1,1-dimethyl-3-propyl-indan-4-yl]-pyridine-3-carboxamide (A.3.37), 2-(difluoromethyl)-N-(3-isobutyl-1,1-dimethyl-indan-4-yl)-pyridine-3-carboxamide (A.3.38), 2-(difluoromethyl)-N-[(3R)-3-isobutyl-1,1-dimethyl-indan-4 yl]pyridine-3-carboxamide (A.3.39).

Other respiration inhibitors: diflumetorim (A.4.1); nitrophenyl derivates: binapacryl (A.4.2), dinobuton (A.4.3), dinocap (A.4.4), fluazinam (A.4.5), meptyldinocap (A.4.6), ferimzone (A.4.7); organometal compounds: fentin salts, e. g. fentin-acetate (A.4.8), fentin chloride (A.4.9) or fentin hydroxide (A.4.10); ametoctradin (A.4.11); silthiofam (A.4.12).

B) Sterol biosynthesis inhibitors (SBI fungicides)

C14 demethylase inhibitors: triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[re/(2S,3R)-3-(2-chlorophenyl)-2-(2,4-difluorophenyl)-oxiranylmethyl]-5-thiocyanato-1H-[1,2,4]triazole (B.1.31), 2-[re-(2 S,3R)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B. 1.36), 2-[4-(4-chloro-phenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.42), 2-(chloromethyl)-2-methyl-5-(p-tolylmethyl)-1-(1,2,4-triazol-1-ylmethyl)cyclopentanol (B.1.43); imidazoles: imazalil (B.1.44), pefurazoate (B.1.45), prochloraz (B.1.46), triflumizol (B.1.47); pyrimidines, pyridines and piperazines: fenarimol (B.1.49), pyrifenox (B.1.50), triforine (B.1.51), [3-(4-chloro-2-fluorophenyl)-5-(2,4-difluorophenyl)isoxazol-4-yl]-(3-pyridyl) methanol (B.1.52).

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8).

Inhibitors of 3-keto reductase: fenhexamid (B.3.1).

Other Sterol biosynthesis inhibitors: chlorphenomizole (B.4.1).

C) Nucleic acid synthesis inhibitors Phenylamides or acyl amino acid fungicides: benalaxyl (C.1.1), benalaxyl-M (C.1.2), kiralaxyl (C.1.3), metalaxyl (C.1.4), metalaxyl-M (C.1.5), ofurace (C.1.6), oxadixyl (C.1.7).

Other nucleic acid synthesis inhibitors: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7), 5-fluoro-2-(4-chlorophenylmethoxy)pyrimidin-4 amine (C.2.8).

D) Inhibitors of cell division and cytoskeleton

Tubulin inhibitors: benomyl (D.1.1), carbendazim (D.1.2), fuberidazole (D1.3), thiabendazole (D.1.4), thiophanate-methyl (D.1.5), 3-chloro-4-(2,6-difluorophenyl)-6-methyl-5-phenyl-pyridazine (D.1.6), 3-chloro-6-methyl-5-phenyl-4-(2,4,6-trifluorophenyl)pyridazine (D.1.7), N-ethyl-2-[(3-ethynyl-8-methyl-6-quinolyl)oxy]butanamide (D.1.8), N-ethyl-2-[(3-ethynyl-8-methyl-6-quinolyl)oxy]-2-methylsulfanyl-acetamide (D.1.9), 2-[(3-ethynyl-8-methyl-6-quinolyl)oxy]-N-(2-fluoroethyl)butanamide (D.1.10), 2-[(3-ethynyl-8-methyl-6-quinolyl)oxy]-N-(2-fluoroethyl)-2-methoxy-acetamide (D.1.11), 2-[(3-ethynyl-8-methyl-6-quinolyl)oxy]-N-propyl-butanamide (D.1.12), 2-[(3-ethynyl-8-methyl-6-quinolyl)oxy]-2-methoxy-N-propyl-acetamide (D.1.13), 2-[(3-ethynyl-8-methyl-6-quinolyl)oxy]-2-methylsulfanyl-N-propyl-acetamide (D.1.14), 2-[(3-ethynyl-8-methyl-6-quinolyl)oxy]-N-(2-fluoroethyl)-2-methylsulfanyl-acetamide (D.1.15), 4-(2-bromo-4-fluorophenyl)-N-(2-chloro-6-fluoro-phenyl)-2,5-dimethyl-pyrazol-3-amine (D.1.16).

Other cell division inhibitors: diethofencarb (D.2.1), ethaboxam (D.2.2), pencycuron (D.2.3), fluopicolide (D.2.4), zoxamide (D.2.5), metrafenone (D.2.6), pyriofenone (D.2.7).

E) Inhibitors of amino acid and protein synthesis

Methionine synthesis inhibitors: cyprodinil (E.1.1), mepanipyrim (E.1.2), pyrimethanil (E.1.3). Protein synthesis inhibitors: blasticidin-S(E.2.1), kasugamycin (E.2.2), kasugamycin hydrochloride-hydrate (E.2.3), mildiomycin (E.2.4), streptomycin (E.2.5), oxytetracyclin (E.2.6).

F) Signal transduction inhibitors

MAP/histidine kinase inhibitors: fluoroimid (F.1.1), iprodione (F.1.2), procymidone (F.1.3), vinclozolin (F.1.4), fludioxonil (F.1.5).

G protein inhibitors: quinoxyfen (F.2.1).

G) Lipid and membrane synthesis inhibitors

Phospholipid biosynthesis inhibitors: edifenphos (G.1.1), iprobenfos (G.1.2), pyrazophos (G.1.3), isoprothiolane (G.1.4).

Lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7).

Phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7).

Compounds affecting cell membrane permeability and fatty acides: propamocarb (G.4.1). Inhibitors of oxysterol binding protein: oxathiapiprolin (G.5.1), 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3), 4-[1-[2-[3-(difluoromethyl)-5-methyl-pyrazol-1-yl]acetyl]-4-piperidyl]-N-tetralin-1-yl-pyridine-2-carboxamide (G.5.4), 4-[1-[2-[3,5-bis(difluoromethyl) pyrazol-1-yl]acetyl]-4-piperidyl]-N-tetralin-1-yl-pyridine-2-carboxamide (G.5.5), 4-[1-[2-[3-(difluoromethyl)-5-(trifluoromethyl)pyrazol-1-yl]acetyl]-4-piperidyl]-N-tetralin-1-yl-pyridine-2-carboxamide (G.5.6), 4-[1-[2-[5-cyclopropyl-3-(difluoromethyl)pyrazol-1-yl]acetyl]-4-piperidyl]-N-tetralin-1-yl-pyridine-2-carboxamide (G.5.7), 4-[1-[2-[5-methyl-3-(trifluoromethyl)pyrazol-1-yl]acetyl]-4-piperidyl]-N-tetralin-1-yl-pyridine-2-carboxamide (G.5.8), 4-[1-[2-[5-(difluoromethyl)-3-(trifluoromethyl) pyrazol-1-yl]acetyl]-4-piperidyl]-N-tetralin-1-yl-pyridine-2-carboxamide (G.5.9), 4-[1-[2-[3,5-bis(trifluoromethyl) pyrazol-1-yl]acetyl]-4-piperidyl]-N-tetralin-1-yl-pyridine-2-carboxamide (G.5.10), (4-[1-[2-[5-cyclopropyl-3-(trifluoromethyl)pyrazol-1-yl]acetyl]-4-piperidyl]-N-tetralin-1-yl-pyridine-2-carboxamide (G.5.11).

H) Inhibitors with Multi Site Action

Inorganic active substances: Bordeaux mixture (H.1.1), copper (H.1.2), copper acetate (H.1.3), copper hydroxide (H.1.4), copper oxychloride (H.1.5), basic copper sulfate (H.1.6), sulfur (H.1.7).

Thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9).

Organochlorine compounds: anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11).

Guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c'] dipyrrole-1,3,5,7(2H,6H)-tetraone (H.4.10).

I) Cell wall synthesis inhibitors

Inhibitors of glucan synthesis: validamycin (1.1.1), polyoxin B (1.1.2).

Melanin synthesis inhibitors: pyroquilon (1.2.1), tricyclazole (1.2.2), carpropamid (1.2.3), dicyclomet (1.2.4), fenoxanil (1.2.5).

J) Plant defence inducers

Acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9), 4-cyclopropyl-N-(2,4-dimethoxyphenyl)thiadiazole-5-carboxamide (J.1.10).

K) Unknown mode of action

Bronopol (K.1.1), chinomethionat (K.1.2), cyflufenamid (K.1.3), cymoxanil (K.1.4), dazomet (K.1.5), debacarb (K.1.6), diclocymet (K.1.7), diclomezine (K.1.8), difenzoquat (K.1.9), di-fenzoquat-methylsulfate (K.1.10), diphenylamin (K.1.11), fenitropan (K.1.12), fenpyrazamine (K.1.13), flumetover (K.1.14), flusulfamide (K.1.15), flutianil (K.1.16), harpin (K.1.17), metha-sulfocarb (K.1.18), nitrapyrin (K.1.19), nitrothal-isopropyl (K.1.20), tolprocarb (K.1.21), oxin-copper (K.1.22), proquinazid (K.1.23), tebufloquin (K.1.24), tecloftalam (K.1.25), triazoxide (K.1.26), N'-(4-(4-chloro-3-trifluoromethyl-phenoxy)-2,5-dimethyl-phenyl)-N-ethyl-N-methyl formamidine (K.1.27), N'-(4-(4-fluoro-3-trifluoromethyl-phenoxy)-2,5-dimethyl-phenyl)-N-ethyl-N-methyl formamidine (K.1.28), N'-[4-[[3-[(4-chlorophenyl)methyl]-1,2,4-thiadiazol-5-yl]oxy]-2,5-dimethyl-phenyl]-N-ethyl-N-methyl-formamidine (K.1.29), N'-(5-bromo-6-indan-2-yloxy-2-methyl-3-pyridyl)-N-ethyl-N-methyl-formamidine (K.1.30), N'-[5-bromo-6-[1-(3,5-difluorophenyl)ethoxy]-2-methyl-3-pyridyl]-N-ethyl-N-methyl-formamidine (K.1.31), N'-[5-bromo-6-(4-isopropylcyclohexoxy)-2-methyl-3-pyridyl]-N-ethyl-N-methyl-formamidine (K.1.32), N'-[5-bromo-2-methyl-6-(1-phenylethoxy)-3-pyridyl]-N-ethyl-N-methyl-formamidine (K.1.33), N'-(2-methyl-5-trifluoromethyl-4-(3-trimethylsilanyl-propoxy)-phenyl)-N-ethyl-N-methyl formamidine (K.1.34), N'-(5-difluoromethyl-2-methyl-4-(3-trimethylsilanyl-propoxy)-phenyl)-N-ethyl-N-methyl formamidine (K.1.35), 2-(4-chloro-phenyl)-N-[4-(3,4-dimethoxy-phenyl)-isoxazol-5-yl]-2-prop-2-ynyloxy-acetamide (K.1.36), 3-[5-(4-chloro-phenyl)-2,3-dimethyl-isoxazolidin-3-yl]-pyridine (pyrisoxazole) (K.1.37), 3-[5-(4-methylphenyl)-2, 3-dimethyl-isoxazolidin-3 yl]-pyridine (K.1.38), 5-chloro-1-(4,6-dimethoxy-pyrimidin-2-yl)-2-methyl-1H-benzoimidazole (K.1.39), ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), but-3-ynyl N-[6-[[(Z)-[(1-methyltetrazol-5-yl)-phenyl-methylene]amino]oxymethyl]-2-pyridyl]carbamate (K.1.43), 2-[2-[(7,8-difluoro-2-methyl-3-quinolyl)oxy]-6-fluoro-phenyl] propan-2-ol (K.1.44), 2-[2-fluoro-6-[(8-fluoro-2-methyl-3-quinolyl)oxy]phen-yl]propan-2-ol (K.1.45), 3-(5-fluoro-3,3,4,4-tetramethyl-3,4-dihydroisoquinolin-1-yl)quinoline (K.1.46), quinofumelin (K.1.47), 3-(4,4,5-trifluoro-3,3-dimethyl-3,4-dihydroisoquinolin-1-yl)quinoline (K.1.48), 9-fluoro-2,2-dimethyl-5-(3-quinolyl)-3H-1,4-benzoxazepine (K.1.49), 2-(6-benzyl-2-pyridyl)quinazoline (K.1.50), 2-[6-(3-fluoro-4-methoxy-phenyl)-5-methyl-2-pyridyl]quinazoline (K.1.51), 3-[(3,4-dichloroisothiazol-5-yl)methoxy]-1,2-benzothiazole 1,1-dioxide (K.1.52), N'-(2, 5-dimethyl-4-phenoxy-phenyl)-N-ethyl-N-methyl-formamidine (K.1.53).

M) Growth regulators abscisic acid (M.1.1), amidochlor, ancymidol, 6-benzylaminopurine, brassinolide, butralin, chlormequat, chlormequat chloride, choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat, mepiquat chloride, naphthaleneacetic acid, N-6-benzyladenine, paclobutrazol, prohexadione, prohexadione-calcium, prohydrojasmon, thidiazuron, triapenthenol, tributyl phosphorotrithioate, 2,3,5-tri-iodobenzoic acid, trinexapac-ethyl and uniconazole;

N) Herbicides from classes N.1 to N.15

N.1 Lipid biosynthesis inhibitors: alloxydim (N.1.1), alloxydim-sodium (N.1.2), butroxydim (N.1.3), clethodim (N.1.4), clodinafop (N.1.5), clodinafop-propargyl (N.1.6), cycloxydim (N.1.7), cyhalofop (N.1.8), cyhalofop-butyl (N.1.9), diclofop(N.1.10), diclofop-methyl (N.1.11), fenoxaprop (N.1.12), fenoxaprop-ethyl (N.1.13), fenoxaprop-P (N.1.14), fenoxaprop-P-ethyl (N.1.15), fluazifop (N.1.16), fluazifop-butyl (N.1.17), fluazifop-P (N.1.18), fluazifop-P-butyl (N.1.19), haloxyfop (N.1.20), haloxyfop-methyl (N.1.21), haloxyfop-P (N.1.22), haloxyfop-P-methyl (N.1.23), metamifop (N.1.24), pinoxaden (N.1.25), profoxydim (N.1.26), propaquizafop (N.1.27), quizalofop (N.1.28), quizalofop-ethyl (N.1.29), quizalofop-tefuryl (N.1.30), quizalofop-P (N.1.31), quizalofop-P-ethyl (N.1.32), quizalofop-P-tefuryl (N.1.33), sethoxydim (N.1.34), tepraloxydim (N.1.35), tralkoxydim (N.1.36), 4-(4'-chloro-4-cyclo-propyl-2'-fluoro[1,1'-biphenyl]-3-yl)-5-hydroxy-2,2,6,6-tetramethyl-2H-pyran-3(6H)-one ((N.1.37) CAS 1312337-72-6); 4-(2',4'-dichloro-4-cyclopropyl[, 1'-biphenyl]-3-yl)-5-hydroxy-2,2,6,6-tetramethyl-2H-pyran-3(6H)-one ((N.1.38) CAS 1312337-45-3); 4-(4'-chloro-4-ethyl-2'-fluoro[1,1'-biphenyl]-3-yl)-5-hydroxy-2,2,6,6-tetramethyl-2H-pyran-3(6H)-one ((N.1.39) CAS 1033757-93-5); 4-(2',4'-Dichloro-4-ethyl[1,1'-biphenyl]-3-yl)-2,2,6,6-tetramethyl-2H-pyran-3,5(4H,6H)-dione ((N.1.40) CAS 1312340-84-3); 5-(acetyloxy)-4-(4'-chloro-4-cyclopropyl-2'-fluoro[1,1'-biphenyl]-3-yl)-3,6-dihydro-2,2,6,6-tetramethyl-2H-pyran-3-one ((N. 1.41) CAS 1312337-48-6); 5-(acetyloxy)-4-(2',4'-dichloro-4-cyclopropyl-[1,1'-biphenyl]-3-yl)-3,6-dihydro-2,2,6,6-tetramethyl-2H-pyran-3-one (N.1.42); 5-(acetyloxy)-4-(4'-chloro-4-ethyl-2'-fluoro[1,1'-biphenyl]-3-yl)-3,6-dihydro-2,2,6,6-tetramethyl-2H-pyran-3-one ((N.1.43) CAS 1312340-82-1); 5-(acetyloxy)-4-(2',4'-dichloro-4-ethyl[1,1'-biphenyl]-3-yl)-3,6-dihydro-2,2,6,6-tetramethyl-2H-pyran-3-one ((N.1.44) CAS 1033760-55-2); 4-(4'-chloro-4-cyclopropyl-2'-fluoro[, 1'-biphenyl]-3-yl)-5,6-dihydro-2,2,6,6-tetramethyl-5-oxo-2H-pyran-3-yl carbonic acid methyl ester ((N.1.45) CAS 1312337-51-1); 4-(2',4'-dichloro-4-cyclopropyl-[1,1'-biphenyl]-3-yl)-5,6-dihydro-2,2,6,6-tetramethyl-5-oxo-2H-pyran-3-yl carbonic acid methyl ester (N.1.46); 4-(4'-chloro-4-ethyl-2'-fluoro[1,1'-biphenyl]-3-yl)-5,6-dihydro-2,2,6,6-tetramethyl-5-oxo-2H-pyran-3-yl carbonic acid methyl ester ((N.1.47) CAS 1312340-83-2); 4-(2',4'-dichloro-4-ethyl¬[1,1'-biphenyl]-3-yl)-5,6-dihydro-2,2,6,6-tetramethyl-5-oxo-2H-pyran-3-yl carbonic acid methyl ester ((N.1.48) CAS 1033760-58-5); benfuresate (N.1.49), butylate (N.1.50), cycloate (N.1.51), dalapon (N.1.52), dimepiperate (N.1.53), EPTC (N.1.54), esprocarb (N.1.55), ethofumesate (N.1.56), flupropanate (N.1.57), molinate (N.1.58), orbencarb (N.1.59), pebulate (N.1.60), prosulfocarb (N.1.61), TCA (N.1.62), thiobencarb (N.1.63), tiocarbazil (N.1.64), triallate (N.1.65) and vernolate (N.1.66); N.2 ALS inhibitors: amidosulfuron (N.2.1), azimsulfuron (N.2.2), bensulfuron (N.2.3), bensul-furon-methyl (N.2.4), chlorimuron (N.2.5), chlorimuron-ethyl (N.2.6), chlorsulfuron (N.2.7), cinosulfuron (N.2.8), cyclosulfamuron (N.2.9), ethametsulfuron (N.2.10), ethametsulfuron-methyl (N.2.11), ethoxysulfuron (N.2.12), flazasulfuron (N.2.13), flucetosulfuron (N.2.14), flupyrsulfuron (N.2.15), flupyrsulfuron-methyl-sodium (N.2.16), foramsulfuron (N.2.17), halosulfuron (N.2.18), halosulfuron-methyl (N.2.19), imazosulfuron (N.2.20), iodosulfuron (N.2.21), iodosulfuron-methyl-sodium (N.2.22), iofensulfuron (N.2.23), iofensulfuron-sodium (N.2.24), mesosulfuron (N.2.25), metazosulfuron (N.2.26), metsulfuron (N.2.27), metsulfuron-methyl (N.2.28), nicosulfuron (N.2.29), orthosulfamuron (N.2.30), oxasulfuron (N.2.31), primisulfuron (N.2.32), primisulfuron-methyl (N.2.33), propyrisulfuron (N.2.34), prosulfuron (N.2.35), pyrazosulfuron (N.2.36), pyrazosulfuron-ethyl (N.2.37), rimsulfuron (N.2.38), sulfometuron (N.2.39), sulfometuron-methyl (N.2.40), sulfosulfuron (N.2.41), thifensulfuron (N.2.42), thifensulfuron-methyl (N.2.43), triasulfuron (N.2.44), tribenuron (N.2.45), tribenuron-methyl (N.2.46), trifloxysulfuron (N.2.47), triflusulfuron (N.2.48), triflusulfuron-methyl (N.2.49), tritosulfuron (N.2.50), imazamethabenz (N.2.51), imazamethabenz-methyl (N.2.52), imazamox (N.2.53), imazapic (N.2.54), imazapyr (N.2.55), imazaquin (N.2.56), imazethapyr (N.2.57); cloransulam (N.2.58), cloransulam-methyl (N.2.59), diclosulam (N.2.60), flumetsulam (N.2.61), florasulam (N.2.62), metosulam (N.2.63), penoxsulam (N.2.64), pyrimisulfan (N.2.65) and pyroxsulam (N.2.66); bispyribac (N.2.67), bispyribac-sodium (N.2.68), pyribenzoxim (N.2.69), pyriftalid (N.2.70), pyriminobac (N.2.71), pyriminobac-methyl (N.2.72), pyrithiobac (N.2.73), pyrithiobac-sodium (N.2.74), 4-[[[2-[(4,6-dimethoxy-2-pyrimidinyl)oxy]phenyl]methyl]amino]-benzoic acid-1-methylhethyl ester ((N.2.75) CAS 420138-41-6), 4-[[[2-[(4,6-dimethoxy-2-pyrimidinyl)oxy]phenyl]methyl]amino]-benzoic acid propyl ester ((N.2.76) CAS 420138-40-5), N-(4-bromophenyl)-2-[(4,6-dimethoxy-2-pyrimidinyl)oxy]benzenemethanamine ((N.2.77) CAS 420138-01-8); flucarbazone (N.2.78), flucarbazone-sodium (N.2.79), propoxycarbazone (N.2.80), propoxycarbazone-sodium (N.2.81), thiencarbazone (N.2.82), thiencarbazone-methyl (N.2.83), triafamone (N.2.84);

N.3 Photosynthesis inhibitors: amicarbazone (N.3.1); chlorotriazine (N.3.2); ametryn (N.3.3), atrazine (N.3.4), chloridazone (N.3.5), cyanazine (N.3.6), desmetryn (N.3.7), dimethametryn (N.3.8), hexazinone (N.3.9), metribuzin (N.3.10), prometon (N.3.11), prometryn (N.3.12), propazine (N.3.13), simazine (N.3.14), simetryn (N.3.15), terbumeton (N.3.16), terbuthylazin (N.3.17), terbutryn (N.3.18), trietazin (N.3.19); chlorobromuron (N.3.20), chlorotoluron (N.3.21), chloroxuron (N.3.22), dimefuron (N.3.23), diuron (N.3.24), fluometuron (N.3.25), isoproturon (N.3.26), isouron (N.3.27), linuron (N.3.28), metamitron (N.3.29), methabenzthiazuron (N.3.30), metobenzuron (N.3.31), metoxuron (N.3.32), monolinuron (N.3.33), neburon (N.3.34), siduron (N.3.35), tebuthiuron (N.3.36), thiadiazuron (N.3.37), desmedipham (N.3.38), karbutilat (N.3.39), phenmedipham (N.3.40), phenmedipham-ethyl (N.3.41), bromofenoxim (N.3.42), bromoxynil (N.3.43) and its salts and esters, ioxynil (N.3.44) and its salts and esters, bromacil (N.3.45), lenacil (N.3.46), terbacil (N.3.47), bentazon (N.3.48), bentazon-sodium (N.3.49), pyridate (N.3.50), pyridafol (N.3.51), pentanochlor (N.3.52), propanil (N.3.53); diquat (N.3.54), diquat-dibromide (N.3.55), paraquat (N.3.56), paraquat-dichloride (N.3.57), paraquat-dimetilsulfate (N.3.58);

N.4 protoporphyrinogen-IX oxidase inhibitors: acifluorfen (N.4.1), acifluorfen-sodium (N.4.2), azafenidin (N.4.3), bencarbazone (N.4.4), benzfendizone (N.4.5), bifenox (N.4.6), butafenacil (N.4.7), carfentrazone (N.4.8), carfentrazone-ethyl (N.4.9), chlormethoxyfen (N.4.10), cinidon-ethyl (N.4.1 1), fluazolate (N.4.12), flufenpyr (N.4.13), flufenpyr-ethyl (N.4.14), flumiclorac (N.4.15), flumiclorac-pentyl (N.4.16), flumioxazin (N.4.17), fluoroglycofen (N.4.18), fluoroglycofen-ethyl (N.4.19), fluthiacet (N.4.20), fluthiacet-methyl (N.4.21), fomesafen (N.4.22), halosafen (N.4.23), lactofen (N.4.24), oxadiargyl (N.4.25), oxadiazon (N.4.26), oxyfluorfen (N.4.27), pentoxazone (N.4.28), profluazol (N.4.29), pyraclonil (N.4.30), pyraflufen (N.4.31), pyraflufen-ethyl (N.4.32), saflufenacil (N.4.33), sulfentrazone (N.4.34), thidiazimin (N.4.35), tiafenacil (N.4.36), trifludimoxazin (N.4.37), ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate ((N.4.38) CAS 353292-31-6), N-ethyl-3-(2,6-dichloro-4-trifluoro-methylphenoxy)-5-methyl-1H-pyrazole-1-carboxamide ((N.4.39) CAS 452098-92-9), N tetrahydrofurfuryl-3-(2,6-dichloro-4-trifluoromethylphenoxy)-5-methyl-1H-pyrazole-1-carboxamide ((N.4.40) CAS 915396-43-9), N-ethyl-3-(2- chloro-6-fluoro-4-trifluoromethylphenoxy)-5-methyl-1H-pyrazole-1-carboxamide ((N.4.41) CAS 452099-05-7), N tetrahydro'furfuryl-3-(2-chloro-6-fluoro-4-trifluoro-methylphenoxy)-5-methyl-1H-pyrazole-1-carboxamide ((N.4.42) CAS 452100-03-7), 3-[7-fluoro-3-oxo-4-(prop-2-ynyl)-3,4-dihydro-2H-benzo[1,4]oxazin-6-yl]-1,5-di methyl-6-thioxo-[1,3,5]triazinan-2,4-dione ((N.4.43) CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione ((N.4.44) CAS 1300118-96-0), 1-methyl-6-trifluoro-methyl-3-(2,2,7-tri-fluoro-3-oxo-4-prop-2-ynyl-3,4-dihydro-2H-benzo[1,4]oxazin-6-yl)-1H-pyrimidine-2,4-dione ((N.4.45) CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate ((N.4.46) CAS 948893-00-3), 3-[7-chloro-5-fluoro-2-(trifluoromethyl)-1H-benzimidazol-4-yl]-1-methyl-6-(trifluoromethyl)-1H-pyrimidine-2,4-dione ((N.4.47) CAS 212754-02-4);

N.5 Bleacher herbicides: beflubutamid (N.5.1), diflufenican (N.5.2), fluridone (N.5.3), flurochloridone (N.5.4), flurtamone (N.5.5), norflurazon (N.5.6), picolinafen (N.5.7), 4-(3-trifluoromethyl phenoxy)-2-(4-trifluoromethylphenyl)-pyrimidine ((N.5.8) CAS 180608-33-7); benzobicyclon (N.5.9), benzofenap (N.5.10), bicyclopyrone (N.5.11), clomazone (N.5.12), fenquintrione (N.5.13), isoxaflutole (N.5.14), mesotrione (N.5.15), pyrasulfotole (N.5.16), pyrazolynate (N.5.17), pyrazoxyfen (N.5.18), sulcotrione (N.5.19), tefuryltrione (N.5.20), tembotrione (N.5.21), tolpyralate (N.5.22), topramezone (N.5.23); aclonifen (N.5.24), amitrole (N.5.25), flumeturon (N.5.26);

N.6 EPSP synthase inhibitors: glyphosate (N.6.1), glyphosate-isopropylammonium (N.6.2), glyposate-potassium (N.6.3), glyphosate-trimesium (sulfosate) (N.6.4); N.7 Glutamine synthase inhibitors: bilanaphos (bialaphos) (N.7.1), bilanaphos-sodium (N.7.2), glufosinate (N.7.3), glufosinate-P (N.7.4), glufosinate-ammonium (N.7.5); N.8 DHP synthase inhibitors: asulam (N.8.1);

N.9 Mitosis inhibitors: benfluralin (N.9.1), butralin (N.9.2), dinitramine (N.9.3), ethalfluralin (N.9.4), fluchloralin (N.9.5), oryzalin (N.9.6), pendimethalin (N.9.7), prodiamine (N.9.8), trifluralin (N.9.9); amiprophos (N.9.10), amiprophos-methyl (N.9.11), butamiphos (N.9.12); chlorthal (N.9.13), chlorthal-dimethyl (N.9.14), dithiopyr (N.9.15), thiazopyr (N.9.16), propyzamide (N.9.17), tebutam (N.9.18); carbetamide (N.9.19), chlorpropham (N.9.20), flamprop (N.9.21), flamprop-isopropyl (N.9.22), flamprop-methyl (N.9.23), flamprop-M-isopropyl (N.9.24), flamprop-M-methyl (N.9.25), propham (N.9.26);

N.10 VLCFA inhibitors: acetochlor (N.10.1), alachlor (N.10.2), butachlor (N.10.3), dimethachlor (N.10.4), dimethenamid (N.10.5), dimethenamid-P (N.10.6), metazachlor (N.10.7), metolachlor (N.10.8), metolachlor-S(N.10.9), pethoxamid (N.10.10), pretilachlor (N.10.11), propachlor (N.10.12), propisochlor (N.10.13), thenylchlor (N.10.14), flufenacet (N.10.15), mefenacet (N.10.16), diphenamid (N.10.17), naproanilide (N.10.18), napropamide (N.10.19), napropamide-M (N.10.20), fentrazamide (N.10.21), anilofos (N.10.22), cafenstrole (N.10.23), fenoxasulfone (N.10.24), ipfencarbazone (N.10.25), piperophos (N.10.26), pyroxasulfone (N.10.27), isoxazoline compounds of the formulae II.1, II.2, II.3, II.4, II.5, II.6, II.7, II.8 and II.9

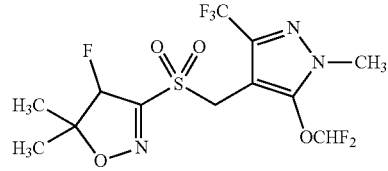

II.1

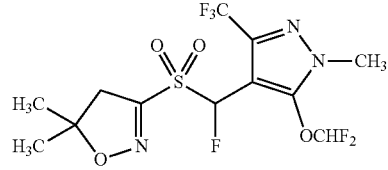

II.2

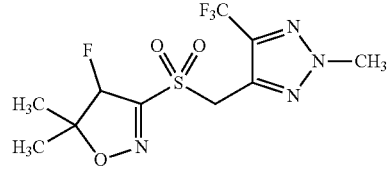

II.3

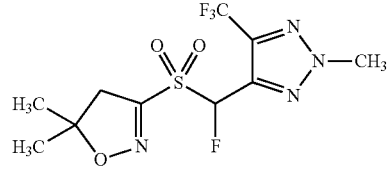

II.4

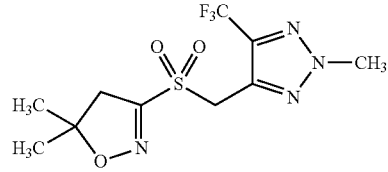

II.5

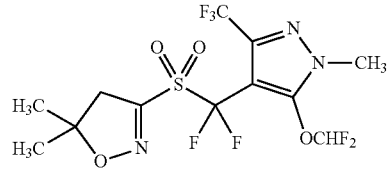

II.6

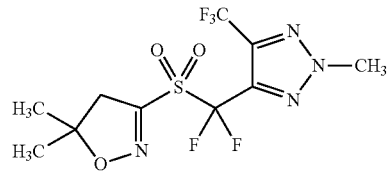

II.7

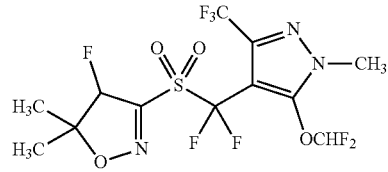

II.8

II.9

[Chemical structure]

N.11 Cellulose biosynthesis inhibitors: chlorthiamid (N.11.1), dichlobenil (N.11.2), flupoxam (N.11.3), indaziflam (N.11.4), isoxaben (N.11.5), triaziflam (N.11.6), 1-cyclohexyl-5-pentafluorphenyloxy-1 4-[1,2,4,6]thiatriazin-3-ylamine ((N. 11.7) CAS 175899-01-1); N.12 Decoupler herbicides: dinoseb (N.12.1), dinoterb (N.12.2), DNOC (N.12.3) and its salts; N.13 Auxinic herbicides: 2,4-D (N.13.1) and its salts and esters, clacyfos (N.13.2), 2,4-DB (N.13.3) and its salts and esters, aminocyclopyrachlor (N.13.4) and its salts and esters, aminopyralid (N.13.5) and its salts such as aminopyralid-dimethylammonium (N.13.6), aminopyralid-tris(2-hydroxypropyl)ammonium (N.13.7) and its esters, benazolin (N.13.8), benazolin-ethyl (N.13.9), chloramben (N.13.10) and its salts and esters, clomeprop (N.13.11), clopyralid (N.13.12) and its salts and esters, dicamba (N.13.13) and its salts and esters, dichlorprop (N.13.14) and its salts and esters, dichlorprop-P (N.13.15) and its salts and esters, fluroxypyr (N.13.16), fluroxypyr-butometyl (N.13.17), fluroxypyr-meptyl (N.13.18), halauxifen (N.13.) and its salts and esters (CAS 943832-60-8); MCPA (N.13.) and its salts and esters, MCPA-thioethyl (N.13.19), MCPB (N.13.20) and its salts and esters, mecoprop (N.13.21) and its salts and esters, mecoprop-P (N.13.22) and its salts and esters, picloram (N.13.23) and its salts and esters, quinclorac (N.13.24), quinmerac (N.13.25), TBA (2,3,6) (N.13.26) and its salts and esters, triclopyr (N.13.27) and its salts and esters, 4-amino-3-chloro-6-(4-chloro-2-fluoro-3-meth-oxyphenyl)-5-fluoropyridine-2-carboxylic acid (N.13.28), benzyl 4-amino-3-chloro-6-(4-chloro-2-fluoro-3-methoxyphenyl)-5-fluoropyridine-2-carboxylate ((N.13.29) CAS 1390661-72-9); N.14 Auxin transport inhibitors: diflufenzopyr (N.14.1), diflufenzopyr-sodium (N.14.2), naptalam (N.14.3) and naptalam-sodium (N.14.4);

N.15 Other herbicides: bromobutide (N.15.1), chlorflurenol (N.15.2), chlorflurenol-methyl (N.15.3), cinmethylin (N.15.4), cumyluron (N.15.5), cyclopyrimorate ((N.15.6) CAS 499223-49-3) and its salts and esters, dalapon (N.15.7), dazomet (N.15.8), difenzoquat (N.15.9), difenzoquat-metilsulfate (N.15.10), dimethipin (N.15.11), DSMA (N.15.12), dymron (N.15.13), endothal (N.15.14) and its salts, etobenzanid (N.15.15), flurenol (N.15.16), flurenol-butyl (N.15.17), flurprimidol (N.15.18), fosamine (N.15.19), fosamine-ammonium (N.15.20), indanofan (N.15.21), maleic hydrazide (N.15.22), mefluidide (N.15.23), metam (N.15.24), methiozolin ((N.15.25) CAS 403640-27-7), methyl azide (N.15.26), methyl bromide (N.15.27), methyldymron (N.15.28), methyl iodide (N.15.29), MSMA (N.15.30), oleic acid (N.15.31), oxaziclomefone (N.15.32), pelargonic acid (N.15.33), pyributicarb (N.15.34), quinoclamine (N.15.35), tridiphane (N.15.36); O) Insecticides from classes O.1 to O.29

O.1 Acetylcholine esterase (AChE) inhibitors: aldicarb (O.1.1), alanycarb (O.1.2), bendiocarb (O.1.3), benfuracarb (O.1.4), butocarboxim (O.1.5), butoxycarboxim (O.1.6), carbaryl (O.1.7), carbofuran (O.1.8), carbosulfan (O.1.9), ethiofencarb (O.1.10), fenobucarb (O.1.11), formetanate (O.1.12), furathiocarb (O.1.13), isoprocarb (O.1.14), methiocarb (O.1.15), methomyl (O.1.16), metolcarb (O.1.17), oxamyl (O.1.18), pirimicarb (O.1.19), propoxur (O.1.20), thiodicarb (O.1.21), thiofanox (O.1.22), trimethacarb (O.1.23), XMC (O.1.24), xylylcarb (O.1.25) and triazamate (O.1.26); acephate (O.1.27), azamethiphos (O.1.28), azinphos-ethyl (O.1.29), azinphosmethyl (O.1.30), cadusafos (O.1.31), chlorethoxyfos (O.1.32), chlorfenvinphos (O.1.33), chlormephos (O.1.34), chlorpyrifos (O.1.35), chlorpyrifos-methyl (O.1.36), coumaphos (O.1.37), cyanophos (O.1.38), demeton-S-methyl (O.1.39), diazinon (O.1.40), dichlorvos/DDVP (O.1.41), dicrotophos (O.1.42), dimethoate (O.1.43), dimethylvinphos (O.1.44), disulfoton (O.1.45), EPN (O.1.46), ethion (O.1.47), ethoprophos (O.1.48), famphur (O.1.49), fenamiphos (O.1.50), fenitrothion (O.1.51), fenthion (O.1.52), fosthiazate (O.1.53), heptenophos (O.1.54), imicyafos (O.1.55), isofenphos (O.1.56), isopropyl O-(methoxyaminothio-phosphoryl) salicylate (O.1.57), isoxathion (O.1.58), malathion (O.1.59), mecarbam (O.1.60), methamidophos (O.1.61), methidathion (O.1.62), mevinphos (O.1.63), monocrotophos (O.1.64), naled (O.1.65), omethoate (O.1.66), oxydemeton-methyl (O.1.67), parathion (O.1.68), parathion-methyl (O.1.69), phenthoate (O.1.70), phorate (O.1.71), phosalone (O.1.72), phosmet (O.1.73), phosphamidon (O.1.74), phoxim (O.1.75), pirimiphos-methyl (O.1.76), profenofos (O.1.77), propetamphos (O.1.78), prothiofos (O.1.79), pyraclofos (O.1.80), pyridaphenthion (O.1.81), quinalphos (O.1.82), sulfotep (O.1.83), tebupirimfos (O.1.84), temephos (O.1.85), terbufos (O.1.86), tetrachlorvinphos (O.1.87), thiometon (O.1.88), triazophos (O.1.89), trichlorfon (O.1.90), vamidothion (O.1.91);

O.2 GABA-gated chloride channel antagonists: endosulfan (O.2.1), chlordane (O.2.2); ethiprole (O.2.3), fipronil (O.2.4), flufiprole (O.2.5), pyrafluprole (O.2.6), pyriprole (O.2.7);

O.3 Sodium channel modulators: acrinathrin (O.3.1), allethrin (O.3.2), d-cis-trans allethrin (O.3.3), d-trans allethrin (O.3.4), bifenthrin (O.3.5), bioallethrin (O.3.6), bioallethrin S-cylclopentenyl (O.3.7), bioresmethrin (O.3.8), cyprothrin (O.3.9), cyfluthrin (O.3.10), beta-cyfluthrin (O.3.11), cyhalothrin (O.3.12), lambda-cyhalothrin (O.3.13), gamma-cyhalothrin (O.3.14), cypermethrin (O.3.15), alpha-cypermethrin (O.3.16), beta-cypermethrin (O.3.17), theta-cypermethrin (O.3.18), zeta-cypermethrin (O.3.19), cyphenothrin (O.3.20), deltamethrin (O.3.21), empenthrin (O.3.22), esfenvalerate (O.3.23), etofenprox (O.3.24), fenpropathrin (O.3.25), fenvalerate (O.3.26), flucythrinate (O.3.27), flumethrin (O.3.28), tau-fluvalinate (O.3.29), halfenprox (O.3.30), heptafluthrin (O.3.31), imiprothrin (O.3.32), meperfluthrin (O.3.33), metofluthrin (O.3.34), momfluorothrin (O.3.35), permethrin (O.3.36), phenothrin (O.3.37), prallethrin (O.3.38), profluthrin (O.3.39), pyrethrin (pyrethrum) (O.3.40), resmethrin (O.3.41), silafluofen (O.3.42), tefluthrin (O.3.43), tetramethylfluthrin (O.3.44), tetramethrin (O.3.45), tralomethrin (O.3.46) and transfluthrin (O.3.47); DDT (O.3.48), methoxychlor (O.3.49);

O.4 Nicotinic acetylcholine receptor agonists (nAChR): acetamiprid (O.4.1), clothianidin (O.4.2), cycloxaprid (O.4.3), dinotefuran (O.4.4), imidacloprid (O.4.5), nitenpyram (O.4.6), thiacloprid (O.4.7), thiamethoxam (O.4.8); (2E)-1-[(6-chloropyridin-3-yl)methyl]-N'-nitro-2-pentylidene-hydrazinecarboximidamide (O.4.9); 1-[(6-chloropyridin-3-yl)methyl]-7-methyl-8-nitro-5-propoxy-1,2,3,5,6,7-hexahydroimidazo[1,2-a]pyridine (O.4.10); nicotine (O.4.11); O.5 Nicotinic acetylcholine receptor allosteric activators: spinosad (O.5.1), spinetoram (O.5.2); O.6 Chloride channel activators: abamectin (O.6.1), emamectin benzoate (O.6.2), ivermectin (O.6.3), lepimectin (O.6.4), milbemectin (O.6.5);

O.7 Juvenile hormone mimics: hydroprene (O.7.1), kinoprene (O.7.2), methoprene (O.7.3); fenoxycarb (O.7.4), pyriproxyfen (O.7.5);

O.8 miscellaneous non-specific (multi-site) inhibitors: methyl bromide (O.8.1) and other alkyl halides; chloropicrin (O.8.2), sulfuryl fluoride (O.8.3), borax (O.8.4), tartar emetic (O.8.5);

O.9 Selective homopteran feeding blockers: pymetrozine (O.9.1), flonicamid (O.9.2);

O.10 Mite growth inhibitors: clofentezine (O.10.1), hexythiazox (O.10.2), diflovidazin (O.10.3); etoxazole (O.10.4);

O.11 Microbial disruptors of insect midgut membranes: the Bt crop proteins: CryIAb, Cry1Ac, CryIFa, Cry2Ab, mCry3A, Cry3Ab, Cry3Bb, Cry34/35Ab1;

O.12 Inhibitors of mitochondrial ATP synthase: diafenthiuron (O.12.1); azocyclotin (O.12.2), cyhexatin (O.12.3), fenbutatin oxide (O.12.4), propargite (O.12.5), tetradifon (O.12.6);

O.13 Uncouplers of oxidative phosphorylation via disruption of the proton gradient: chlorfenapyr (O.13.1), DNOC (O.13.2), sulfluramid (O.13.3);

O.14 Nicotinic acetylcholine receptor (nAChR) channel blockers: bensultap (O.14.1), cartap hydrochloride (O.14.2), thiocyclam (O.14.3), thiosultap sodium (O.14.4);

O.15 Inhibitors of the chitin biosynthesis type 0: bistrifluron (O.15.1), chlorfluazuron (O.15.2), diflubenzuron (O.15.3), flucycloxuron (O.15.4), flufenoxuron (O.15.5), hexaflumuron (O.15.6), lufenuron (O.15.7), novaluron (O.15.8), noviflumuron (O.15.9), teflubenzuron (O.15.10), triflumuron (O.15.11);

O.16 Inhibitors of the chitin biosynthesis type 1: buprofezin (O.16.1);

O.17 Moulting disruptors: cyromazine (O.17.1);

O.18 Ecdyson receptor agonists: methoxyfenozide (O.18.1), tebufenozide (O.18.2), halofenozide (O.18.3), fufenozide (O.18.4), chromafenozide (O.18.5);

O.19 Octopamin receptor agonists: amitraz (O.19.1);

O.20 Mitochondrial complex III electron transport inhibitors: hydramethylnon (O.20.1), acequinocyl (O.20.2), fluacrypyrim (O.20.3);

O.21 Mitochondrial complex I electron transport inhibitors: fenazaquin (O.21.1), fenpyroximate (O.21.2), pyrimidifen (O.21.3), pyridaben (O.21.4), tebufenpyrad (O.21.5), tolfenpyrad (O.21.6); rotenone (O.21.7);

O.22 Voltage-dependent sodium channel blockers: indoxacarb (O.22.1), metaflumizone (O.22.2), 2-[2-(4-cyanophenyl)-1-[3-(trifluoromethyl)phenyl]ethylidene]-N-[4-(difluoromethoxy)phenyl]-hydrazinecarboxamide (O.22.3), N-(3-chloro-2-methylphenyl)-2-[(4-chlorophenyl)-[4-[methyl (methylsulfonyl)amino]phenyl]methylene]-hydrazinecarboxamide (O.22.4);

O.23 Inhibitors of the of acetyl CoA carboxylase: spirodiclofen (O.23.1), spiromesifen (O.23.2), spirotetramat (O.23.3);

O.24 Mitochondrial complex IV electron transport inhibitors: aluminium phosphide (O.24.1), calcium phosphide (O.24.2), phosphine (O.24.3), zinc phosphide (O.24.4), cyanide (O.24.5);

O.25 Mitochondrial complex II electron transport inhibitors: cyenopyrafen (O.25.1), cyflumetofen (O.25.2);

O.26 Ryanodine receptor-modulators: flubendiamide (O.26.1), chlorantraniliprole (O.26.2), cyantraniliprole (O.26.3), cyclaniliprole (O.26.4), tetraniliprole (O.26.5);

(R)-3-chloro-N1-{2-methyl-4-[1,2,2,2-tetrafluoro-1-(trifluoromethyl)ethyl]phenyl}-N2-(1-methyl-2-methylsulfonylethyl)phthalamide (O.26.6), (S)-3-chloro-N1-{2-methyl-4-[1,2,2,2-tetrafluoro-1-(trifluoromethyl)ethyl]phenyl}-N2-(1-methyl-2-methylsulfonylethyl)phthalamide (O.26.7), methyl-2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (O.26.8); N-[4,6-dichloro-2-[(diethyl-lambda-4-sulfanylidene)-carbamoyl]-phenyl]-2-(3-chloro-2-pyridyl)-5-(trifluoromethyl)pyrazole-3-carboxamide (O.26.9); N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide (O.26.10); N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide (O.26.11); N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide (O.26.12); N-[4,6-dibromo-2-[(diethyl-lambda-4-sulfanylidene)carbamoyl]-phenyl]-2-(3-chloro-2-pyridyl)-5-(tri-fluoromethyl)pyrazole-3-carboxamide (O.26.13); N-[2-(5-amino-1,3,4-thiadiazol-2-yl)-4-chloro-6-methylphenyl]-3-bromo-1-(3-chloro-2-pyridinyl)-1H-pyrazole-5-carboxamide (O.26.14); 3-chloro-1-(3-chloro-2-pyridinyl)-N-[2,4-dichloro-6-[[(1-cyano-1-methylethyl)amino]carbonyl]phenyl]-1H-pyrazole-5-carboxamide (O.26.15); 3-bromo-N-[2,4-dichloro-6-(methylcarbamoyl)phenyl]-1-(3,5-dichloro-2-pyridyl)-1H-pyrazole-5-carboxamide (O.26.16); N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide (O.26.17); cyhalodiamide (O.26.18);

O.27. insecticidal active compounds of unknown or uncertain mode of action: afidopyropen (O.27.1), afoxolaner (O.27.2), azadirachtin (O.27.3), amidoflumet (O.27.4), benzoximate (O.27.5), bifenazate (O.27.6), broflanilide (O.27.7), bromopropylate (O.27.8), chinomethionat (O.27.9), cryolite (O.27.10), dicloromezotiaz (O.27.11), dicofol (O.27.12), flufenerim (O.27.13), flometoquin (O.27.14), fluensulfone (O.27.15), fluhexafon (O.27.16), fluopyram (O.27.17), flupyradifurone (O.27.18), fluralaner (O.27.19), metoxadiazone (O.27.20), piperonyl butoxide (O.27.21), pyflubumide (O.27.22), pyridalyl (O.27.23), pyrifluquinazon (O.27.24), sulfoxaflor (O.27.25), tioxazafen (O.27.26), triflumezopyrim (O.27.27), 11-(4-chloro-2,6-dimethylphenyl)-12-hydroxy-1,4-dioxa-9-azadispiro[4.2.4.2]-tetradec-11-en-10-one (O.27.28), 3-(4'-fluoro-2,4-dimethylbiphenyl-3-yl)-4-hydroxy-8-oxa-1-azaspiro[4.5]dec-3-en-2-one (O.27.28), 1-[2-fluoro-4-methyl-5-[(2,2,2-trifluoroethyl)sulfinyl]phenyl]-3-(trifluoromethyl)-1H-1,2,4-triazole-5-amine (O.27.29), (E/Z)-N-[1-[(6-chloro-3-pyridyl)methyl]-2-pyridylidene]-2,2,2-trifluoro-acetamide (O.27.31); (E/Z)-N-[1-[(6-chloro-5-fluoro-3-pyridyl)methyl]-2-pyridylidene]-2,2,2-trifluoro-acetamide (O.27.32); (E/Z)-2,2,2-trifluoro-N-[1-[(6-fluoro-3-pyridyl)methyl]-2-pyridylidene]acetamide (O.27.33); (E/Z)-N-[1-[(6-bromo-3-pyridyl)methyl]-2-pyridylidene]-2,2,2-trifluoro-acetamide (O.27.34); (E/Z)-N-[1-[1-(6-chloro-3-pyridyl)ethyl]-2-pyridylidene]-2,2,2-trifluoro-acetamide (O.27.35); (E/Z)-N-[1-[(6-chloro-3-pyridyl)methyl]-2-pyridylidene]-2,2-difluoro-acetamide (O.27.36); (E/Z)-2-chloro-N-[1-[(6-chloro-3-pyridyl)methyl]-2-pyridylidene]-2,2-difluoro-acetamide (O.27.37); (E/Z)-N-[1-[(2-chloropyrimidin-5-yl)methyl]-2-pyridylidene]-2,2,2-trifluoro-acetamide (O.27.38); (E/Z)-N-[1-[(6-chloro-3-pyridyl)methyl]-2-pyridylidene]-2,2,3,3,3-pentafluoro-propanamide (O.27.39); N-[1-[(6-chloro-3-pyridyl)methyl]-

2-pyridylidene]-2,2,2-trifluoro-thioacetamide (O.27.40); N-[1-[(6-chloro-3-pyridyl)methyl]-2-pyridylidene]-2,2,2-trifluoro-N'-isopropyl-acetamidine (O.27.41); fluazaindolizine (O.27.42); 4-[5-(3,5-dichlorophenyl)-5-(trifluoromethyl)-4H-isoxazol-3-yl]-2-methyl-N-(1-oxothietan-3-yl) benzamide (O.27.43); fluxamet-amide (O.27.44); 5-[3-[2,6-dichloro-4-(3,3-dichloroallyloxy)phenoxy]propoxy]-1H-pyrazole (O.27.45); 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide (O.27.46); 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide (O.27.47); N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide (O.27.48); N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methyl-benzamide (O.27.49); 4-fluoro-N-[2-fluoro-3-[[[2-iodo-4-[1,2,2,2-tetrafluoro-1-(trifluoromethyl)ethyl]-6-(trifluoro-methyl)phenyl]amino]carbonyl]phenyl]-N-methyl-benzamide (O.27.50); 3-fluoro-N-[2-fluoro-3-[[[2-iodo-4-[1,2,2,2-tetrafluoro-1-(trifluoromethyl)ethyl]-6(trifluoromethyl)phenyl]amino]carbonyl]phenyl]-N-methyl-benzamide (O.27.51); 2-chloro-N-[3-[[[2-iodo-4-[1,2,2,2-tetrafluoro-1-(trifluoromethyl)ethyl]-6-(trifluoromethyl)phenyl]amino] carbonyl]phenyl]-3-pyridinecarboxamide (O.27.52); 4-cyano-N-[2-cyano-5-[[2,6-dibromo-4-[1,2,2,3,3,3-hexafluoro-1-(trifluorometh-yl)propyl]phenyl]carbamoyl] phenyl]-2-methyl-benzamide (O.27.53); 4-cyano-3-[(4-cyano-2-methyl-benzoyl)amino]-N-[2,6-dichloro-4-[1,2,2,3,3,3-hexafluoro-1-(trifluoromethyl)-propyl]phenyl]-2-fluoro-benzamide (O.27.54); N-[5-[[2-chloro-6-cyano-4-[1,2,2,3,3,3-hexafluoro-1-(trifluoromethyl)propyl]phenyl] carbamoyl]-2-cyano-phenyl]-4-cyano-2-methyl-benzamide (O.27.55); N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide (O.27.56); N-[5-[[2-bromo-6-chloro-4-[1,2,2,3,3,3-hexafluoro-1-(trifluoromethyl)-propyl]phenyl]carbamoyl]-2-cyano-phenyl]-4-cyano-2-methyl-benzamide (O.27.57); 4-cyano-N-[2-cyano-5-[[2,6-dichloro-4-[1,2,2,3,3,3-hexafluoro-1-(trifluoromethyl) propyl]phenyl]-carbamoyl]phenyl]-2-methyl-benzamide (O.27.58); 4-cyano-N-[2-cyano-5-[[2,6-dichloro-4-[1,2,2,2-tetrafluoro-1-(trifluoromethyl)ethyl] phenyl]carbamoyl]phenyl]-2-methyl-benzamide (O.27.59); N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide (O.27.60); 2-(1,3-dioxan-2-yl)-6-[2-(3-pyridinyl)-5-thiazolyl]-pyridine; 2-[6-[2-(5-fluoro-3-pyridinyl)-5-thiazolyl]-2-pyridinyl]-pyrimidine (O.27.61); 2-[6-[2-(3-pyridinyl)-5-thiazolyl]-2-pyridinyl]-pyrimidine (O.27.62); N-methylsulfonyl-6-[2-(3-pyridyl) thiazol-5-yl]pyridine-2-carboxamide (O.27.63); N-methylsulfonyl-6-[2-(3-pyridyl)thiazol-5-yl]pyridine-2-carboxamide (O.27.64); N-ethyl-N-[4-methyl-2-(3-pyridyl) thiazol-5-yl]-3-methylthio-propanamide (O.27.65); N-methyl-N-[4-methyl-2-(3-pyridyl)thiazol-5-yl]-3-methyl-thio-propanamide (O.27.66); N,2-dimethyl-N-[4-methyl-2-(3-pyridyl)thiazol-5-yl]-3-methylthio-propanamide (O.27.67); N-ethyl-2-methyl-N-[4-methyl-2-(3-pyridyl)thiazol-5-yl]-3-methylthio-propanamide (O.27.68); N-[4-chloro-2-(3-pyridyl)thiazol-5-yl]-N-ethyl-2-methyl-3-methylthio-propanamide (O.2769.); N-[4-chloro-2-(3-pyridyl) thiazol-5-yl]-N,2-dimethyl-3-methylthio-propanamide (O.27.70); N-[4-chloro-2-(3-pyridyl)thiazol-5-yl]-N-methyl-3-methylthio-propanamide (O.27.71); N-[4-chloro-2-(3-pyridyl)thiazol-5-yl]-N-ethyl-3-methylthio-propanamide (O.27.72); 1-[(6-chloro-3-pyridinyl)methyl]-1,2,3,5,6,7-hexahydro-5-methoxy-7-methyl-8-nitro-imidazo[1,2-a] pyridine (O.27.73); 1-[(6-chloropyridin-3-yl)methyl]-7-methyl-8-nitro-1,2,3,5,6,7-hexahydroimidazo[1,2-a] pyridin-5-ol (O.27.74); 1-isopropyl-N,5-dimethyl-N-pyridazin-4-yl-pyrazole-4-carboxamide (O.27.75); 1-(1,2-dimethylpropyl)-N-ethyl-5-methyl-N-pyridazin-4-yl-pyrazole-4-carboxamide (O.27.76); N,5-dimethyl-N-pyridazin-4-yl-1-(2,2,2-trifluoro-1-methyl-ethyl)pyrazole-4-carboxamide (O.27.77); 1-[1-(1-cyanocyclopropyl)ethyl]-N-ethyl-5-methyl-N-pyridazin-4-yl-pyrazole-4-carboxamide (O.27.78); N-ethyl-1-(2-fluoro-1-methyl-propyl)-5-methyl-N-pyridazin-4-yl-pyrazole-4-carboxamide (O.27.79); 1-(1,2-dimethylpropyl)-N,5-dimethyl-N-pyridazin-4-yl-pyrazole-4-carboxamide (O.27.80); 1-[1-(1-cyanocyclopropyl)ethyl]-N,5-dimethyl-N-pyridazin-4-yl-pyrazole-4-carboxamide (O.27.81); N-methyl-1-(2-fluoro-1-methyl-propyl)-5-methyl-N-pyridazin-4-yl-pyrazole-4-carboxamide (O.27.82); 1-(4,4-difluorocyclohexyl)-N-ethyl-5-methyl-N-pyridazin-4-yl-pyrazole-4-carboxamide (O.27.83); 1-(4,4-difluorocyclohexyl)-N,5-dimethyl-N-pyridazin-4-yl-pyrazole-4-carboxamide (O.27.84), N-(1-methylethyl)-2-(3-pyridinyl)-2H-indazole-4-carboxamide (O.27.85); N-cyclopropyl-2-(3-pyridinyl)-2H-indazole-4-carboxamide (O.27.86); N-cyclohexyl-2-(3-pyridinyl)-2H-indazole-4-carboxamide (O.27.87); 2-(3-pyridinyl)-N-(2,2,2-trifluoroethyl)-2H-indazole-4-carboxamide (O.27.88); 2-(3-pyridinyl)-N-[(tetrahydro-2-furanyl)methyl]-2H-indazole-5-carboxamide (O.27.89); methyl 2-[[2-(3-pyridinyl)-2H-indazol-5-yl]carbonyl]hydrazinecarboxylate (O.27.90); N-[(2,2-difluorocyclopropyl)methyl]-2-(3-pyridinyl)-2H-indazole-5-carboxamide (O.27.91); N-(2,2-difluoropropyl)-2-(3-pyridinyl)-2H-indazole-5-carboxamide (O.27.92); 2-(3-pyridinyl)-N-(2-pyrimidinylmethyl)-2H-indazole-5-carboxamide (O.27.93); N-[(5-methyl-2-pyrazinyl)methyl]-2-(3-pyridinyl)-2H-indazole-5-carboxamide (O.27.94), N-[3-chloro-1-(3-pyridyl)pyrazol-4-yl]-N-ethyl-3-(3,3,3-trifluoropropylsulfanyl)-propanamide (O.27.95); N-[3-chloro-1-(3-pyridyl)pyrazol-4-yl]-N-ethyl-3-(3,3,3-trifluoropropylsulfinyl)propanamide (O.27.96); N-[3-chloro-1-(3-pyridyl)pyrazol-4-yl]-3-[(2,2-di-fluorocyclopropyl)methylsulfanyl]-N-ethyl-propanamide (O.27.97); N-[3-chloro-1-(3-pyridyl)pyrazol-4-yl]-3-[(2,2-difluorocyclopropyl)methylsulfinyl]-N-ethyl-propanamide (O.27.98); sarolaner (O.27.99), lotilaner (O.27.100).

The active substances referred to as component 2, their preparation and their activity e. g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296, 272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 10/139271, WO 11/028657, WO 12/168188, WO 07/006670, WO 11/77514; WO 13/047749, WO 10/069882, WO 13/047441, WO 03/16303, WO 09/90181, WO 13/007767, WO 13/010862, WO 13/127704, WO 13/024009, WO 13/24010, WO 13/047441, WO 13/162072, WO 13/092224, WO 11/135833, CN 1907024, CN 1456054, CN 103387541, CN 1309897, WO 12/84812, CN 1907024, WO 09094442, WO 14/60177, WO 13/116251, WO 08/013622, WO 15/65922, WO 94/01546, EP 2865265, WO 07/129454, WO 12/165511, WO 11/081174, WO 13/47441).

The present invention furthermore relates to agrochemical compositions comprising a mixture of at least one compound I (component 1) and at least one further active substance useful for plant protection, e. g. selected from the groups A) to O) (component 2), in particular one further fungicide, e. g. one or more fungicide from the groups A) to K), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to K), as described above, is more efficient than combating those fungi with individual compounds I or individual fungicides from groups A) to K).

By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e. g. as tank-mix) or seperately, or in succession, wherein the time interval between the individual applications is selected to ensure that the active substance applied first still occurs at the site of action in a sufficient amount at the time of application of the further active substance(s). The order of application is not essential for working of the present invention.

When applying compound I and a pesticide II sequentially the time between both applications may vary e. g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day.

In the binary mixtures and compositions according to the invention the weight ratio of the component 1) and the component 2) generally depends from the properties of the active components used, usually it is in the range of from 1:10,000 to 10,000:1, often it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to further embodiments of the binary mixtures and compositions, the weight ratio of the component 1) and the component 2) usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiments of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

Preference is also given to mixtures comprising as component 2) at least one active substance selected from inhibitors of complex III at $Q_o$ site in group A), more preferably selected from compounds (A.1.1), (A.1.4), (A.1.8), (A.1.9), (A.1.10), (A.1.12), (A.1.13), (A.1.14), (A.1.17), (A.1.21), (A.1.24), (A.1.25), (A.1.26), (A.1.27), (A.1.30), (A.1.31), (A.1.32), (A.1.34) and (A.1.35); particularly selected from (A.1.1), (A.1.4), (A.1.8), (A.1.9), (A.1.13), (A.1.14), (A.1.17), (A.1.24), (A.1.25), (A.1.26), (A.1.27), (A.1.30), (A.1.31), (A.1.32), (A.1.34) and (A.1.35). Preference is also given to mixtures comprising as component 2) at least one active substance selected from inhibitors of complex III at Qi site in group A), more preferably selected from compounds (A.2.1), (A.2.3) and (A.2.4); particularly selected from (A.2.3) and (A.2.4).

Preference is also given to mixtures comprising as component 2) at least one active substance selected from inhibitors of complex II in group A), more preferably selected from compounds (A.3.2), (A.3.3), (A.3.4), (A.3.7), (A.3.9), (A.3.11), (A.3.12), (A.3.15), (A.3.16), (A.3.17), (A.3.18), (A.3.19), (A.3.20), (A.3.21), (A.3.22), (A.3.23), (A.3.24), (A.3.25), (A.3.27), (A.3.28), (A.3.29), (A.3.31), (A.3.32), (A.3.33), (A.3.34), (A.3.35), (A.3.36), (A.3.37), (A.3.38) and (A.3.39); particularly selected from (A.3.2), (A.3.3), (A.3.4), (A.3.7), (A.3.9), (A.3.12), (A.3.15), (A.3.17), (A.3.19), (A.3.22), (A.3.23), (A.3.24), (A.3.25), (A.3.27), (A.3.29), (A.3.31), (A.3.32), (A.3.33), (A.3.34), (A.3.35), (A.3.36), (A.3.37), (A.3.38) and (A.3.39).

Preference is also given to mixtures comprising as component 2) at least one active substance selected from other respiration inhibitors in group A), more preferably selected from compounds (A.4.5) and (A.4.11); in particular (A.4.11).

Preference is also given to mixtures comprising as component 2) at least one active substance selected from $C_{14}$ demethylase inhibitors in group B), more preferably selected from compounds (B.1.4), (B.1.5), (B.1.8), (B.1.10), (B.1.11), (B.1.12), (B.1.13), (B.1.17), (B.1.18), (B.1.21), (B.1.22), (B.1.23), (B.1.25), (B.1.26), (B.1.29), (B.1.34), (B.1.37), (B.1.38), (B.1.43) and (B.1.46); particularly selected from (B.1.5), (B.1.8), (B.1.10), (B.1.17), (B.1.22), (B.1.23), (B.1.25), (B.1.33), (B.1.34), (B.1.37), (B.138), (B.1.43) and (B.1.46).

Preference is also given to mixtures comprising as component 2) at least one active substance selected from Delta14-reductase inhibitors in group B), more preferably selected from compounds (B.2.4), (B.2.5), (B.2.6) and (B.2.8); in particular (B.2.4).

Preference is also given to mixtures comprising as component 2) at least one active substance selected from phenylamides and acyl amino acid fungicides in group C), more preferably selected from compounds (C.1.1), (C.1.2), (C.1.4) and (C.1.5); particularly selected from (C.1.1) and (C.1.4).

Preference is also given to mixtures comprising as component 2) at least one active substance selected from other nucleic acid synthesis inhibitors in group C), more preferably selected from compounds (C.2.6), (C.2.7) and (C.2.8).

Preference is also given to mixtures comprising as component 2) at least one active substance selected from group D), more preferably selected from compounds (D.1.1), (D.1.2), (D.1.5), (D.2.4) and (D.2.6); particularly selected from (D.1.2), (D.1.5) and (D.2.6).

Preference is also given to mixtures comprising as component 2) at least one active substance selected from group E), more preferably selected from compounds (E.1.1), (E.1.3), (E.2.2) and (E.2.3); in particular (E.1.3).

Preference is also given to mixtures comprising as component 2) at least one active substance selected from group F), more preferably selected from compounds (F.1.2), (F.1.4) and (F.1.5).

Preference is also given to mixtures comprising as component 2) at least one active substance selected from group G), more preferably selected from compounds (G.3.1), (G.3.3), (G.3.6), (G.5.1), (G.5.2), (G.5.3), (G.5.4), (G.5.5), G.5.6), G.5.7), (G.5.8), (G.5.9), (G.5.10) and (G.5.11); particularly selected from (G.3.1), (G.5.1), (G.5.2) and (G.5.3).

Preference is also given to mixtures comprising as component 2) at least one active substance selected from group H), more preferably selected from compounds (H.2.2), (H.2.3), (H.2.5), (H.2.7), (H.2.8), (H.3.2), (H.3.4), (H.3.5), (H.4.9) and (H.4.10); particularly selected from (H.2.2), (H.2.5), (H.3.2), (H.4.9) and (H.4.10).

Preference is also given to mixtures comprising as component 2) at least one active substance selected from group I), more preferably selected from compounds (1.2.2) and (1.2.5).

Preference is also given to mixtures comprising as component 2) at least one active substance selected from group J), more preferably selected from compounds (J.1.2), (J.1.5) and (J.1.8); in particular (J.1.5).

Preference is also given to mixtures comprising as component 2) at least one active substance selected from group K), more preferably selected from compounds (K.1.41), (K.1.42), (K.1.44), (K.1.45), (K.1.47) and (K.1.49); particularly selected from (K.1.41), (K.1.44), (K.1.45), (K.1.47) and (K.1.49).

Accordingly, the present invention furthermore relates to mixtures comprising one compound of the formula I (component 1) and one pesticide B (component 2), wherein pesticide B is selected from the column "Co. 2" of the lines B-1 to B-727 of Table B.

A further embodiment relates to the mixtures B-1 to B-727 listed in Table B, where a row of Table B corresponds in each case to a fungicidal mixture comprising as active components one of the in the present specification individualized compounds of formula I, i.e. compounds I as defined Tables 1 to 108 and even more preferably compounds 1 to 60 as defined in table C (component 1 in column "Co.1") and the respective pesticide B from groups A) to O) (component 2) stated in the row in question.

Preferably, the compositions described in Table B comprise the active components in synergistically effective amounts.

TABLE B

Mixtures comprising as active components one individual compound of the formula I (in column Co. 1), in particular compounds 1 to 38 as defined in table C and compounds II-1 to II-455 as defined in table B, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-1 | (I) | (A.1.1) |
| B-2 | (I) | (A.1.2) |
| B-3 | (I) | (A.1.3) |
| B-4 | (I) | (A.1.4) |
| B-5 | (I) | (A.1.5) |
| B-6 | (I) | (A.1.6) |
| B-7 | (I) | (A.1.7) |
| B-8 | (I) | (A.1.8) |
| B-9 | (I) | (A.1.9) |
| B-10 | (I) | (A.1.10) |
| B-11 | (I) | (A.1.11) |
| B-12 | (I) | (A.1.12) |
| B-13 | (I) | (A.1.13) |
| B-14 | (I) | (A.1.14) |
| B-15 | (I) | (A.1.15) |
| B-16 | (I) | (A.1.16) |
| B-17 | (I) | (A.1.17) |
| B-18 | (I) | (A.1.18) |
| B-19 | (I) | (A.1.19) |
| B-20 | (I) | (A.1.20) |
| B-21 | (I) | (A.1.21) |
| B-22 | (I) | (A.1.22) |
| B-23 | (I) | (A.1.23) |
| B-24 | (I) | (A.1.24) |
| B-25 | (I) | (A.1.25) |
| B-26 | (I) | (A.1.26) |
| B-27 | (I) | (A.1.27) |
| B-28 | (I) | (A.1.30) |
| B-29 | (I) | (A.1.31) |
| B-30 | (I) | (A.1.32) |
| B-31 | (I) | (A.2.1) |
| B-32 | (I) | (A.2.2) |
| B-33 | (I) | (A.2.3) |
| B-34 | (I) | (A.2.4) |
| B-35 | (I) | (A.2.6) |
| B-36 | (I) | (A.2.7) |
| B-37 | (I) | (A.2.8) |
| B-38 | (I) | (A.3.1) |
| B-39 | (I) | (A.3.2) |
| B-40 | (I) | (A.3.3) |
| B-41 | (I) | (A.3.4) |
| B-42 | (I) | (A.3.5) |
| B-43 | (I) | (A.3.6) |
| B-44 | (I) | (A.3.7) |
| B-45 | (I) | (A.3.8) |
| B-46 | (I) | (A.3.9) |
| B-47 | (I) | (A.3.10) |
| B-48 | (I) | (A.3.11) |
| B-49 | (I) | (A.3.12) |
| B-50 | (I) | (A.3.13) |
| B-51 | (I) | (A.3.14) |
| B-52 | (I) | (A.3.15) |
| B-53 | (I) | (A.3.16) |
| B-54 | (I) | (A.3.17) |
| B-55 | (I) | (A.3.18) |
| B-56 | (I) | (A.3.19) |
| B-57 | (I) | (A.3.20) |
| B-58 | (I) | (A.3.21) |
| B-59 | (I) | (A.3.22) |
| B-60 | (I) | (A.3.23) |
| B-61 | (I) | (A.3.24) |
| B-62 | (I) | (A.3.25) |
| B-63 | (I) | (A.3.26) |
| B-64 | (I) | (A.3.27) |
| B-65 | (I) | (A.3.28) |

TABLE B-continued

Mixtures comprising as active components one individual compound of the formula I (in column Co. 1), in particular compounds 1 to 38 as defined in table C and compounds II-1 to II-455 as defined in table B, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-66 | (I) | (A.3.29) |
| B-67 | (I) | (A.3.30) |
| B-68 | (I) | (A.3.31) |
| B-69 | (I) | (A.3.32) |
| B-70 | (I) | (A.3.33) |
| B-71 | (I) | (A.3.34) |
| B-72 | (I) | (A.3.35) |
| B-73 | (I) | (A.3.36) |
| B-74 | (I) | (A.3.37) |
| B-75 | (I) | (A.3.38) |
| B-76 | (I) | (A.3.39) |
| B-77 | (I) | (A.4.1) |
| B-78 | (I) | (A.4.2) |
| B-79 | (I) | (A.4.3) |
| B-80 | (I) | (A.4.4) |
| B-81 | (I) | (A.4.5) |
| B-82 | (I) | (A.4.6) |
| B-83 | (I) | (A.4.7) |
| B-84 | (I) | (A.4.8) |
| B-85 | (I) | (A.4.9) |
| B-86 | (I) | (A.4.10) |
| B-87 | (I) | (A.4.11) |
| B-88 | (I) | (A.4.12) |
| B-89 | (I) | (B.1.1) |
| B-90 | (I) | (B.1.2) |
| B-91 | (I) | (B.1.3) |
| B-92 | (I) | (B.1.4) |
| B-93 | (I) | (B.1.5) |
| B-94 | (I) | (B.1.6) |
| B-95 | (I) | (B.1.7) |
| B-96 | (I) | (B.1.8) |
| B-97 | (I) | (B.1.9) |
| B-98 | (I) | (B.1.10) |
| B-99 | (I) | (B.1.11) |
| B-100 | (I) | (B.1.12) |
| B-101 | (I) | (B.1.13) |
| B-102 | (I) | (B.1.14) |
| B-103 | (I) | (B.1.15) |
| B-104 | (I) | (B.1.16) |
| B-105 | (I) | (B.1.17) |
| B-106 | (I) | (B.1.18) |
| B-107 | (I) | (B.1.19) |
| B-108 | (I) | (B.1.20) |
| B-109 | (I) | (B.1.21) |
| B-110 | (I) | (B.1.22) |
| B-111 | (I) | (B.1.23) |
| B-112 | (I) | (B.1.24) |
| B-113 | (I) | (B.1.25) |
| B-114 | (I) | (B.1.26) |
| B-115 | (I) | (B.1.27) |
| B-116 | (I) | (B.1.28) |
| B-117 | (I) | (B.1.29) |
| B-118 | (I) | (B.1.30) |
| B-119 | (I) | (B.1.34) |
| B-120 | (I) | (B.1.37) |
| B-121 | (I) | (B.1.38) |
| B-122 | (I) | (B.1.43) |
| B-123 | (I) | (B.1.44) |
| B-124 | (I) | (B.1.45) |
| B-125 | (I) | (B.1.46) |
| B-126 | (I) | (B.1.47) |
| B-127 | (I) | (B.1.48) |
| B-128 | (I) | (B.1.49) |
| B-129 | (I) | (B.1.50) |
| B-130 | (I) | (B.1.51) |
| B-131 | (I) | (B.2.1) |
| B-132 | (I) | (B.2.2) |
| B-133 | (I) | (B.2.3) |
| B-134 | (I) | (B.2.4) |
| B-135 | (I) | (B.2.5) |
| B-136 | (I) | (B.2.6) |
| B-137 | (I) | (B.2.7) |
| B-138 | (I) | (B.2.8) |
| B-139 | (I) | (B.3.1) |
| B-140 | (I) | (C.1.1) |
| B-141 | (I) | (C.1.2) |
| B-142 | (I) | (C.1.3) |
| B-143 | (I) | (C.1.4) |
| B-144 | (I) | (C.1.5) |
| B-145 | (I) | (C.1.6) |
| B-146 | (I) | (C.1.7) |
| B-147 | (I) | (C.2.1) |
| B-148 | (I) | (C.2.2) |
| B-149 | (I) | (C.2.3) |
| B-150 | (I) | (C.2.4) |
| B-151 | (I) | (C.2.5) |
| B-152 | (I) | (C.2.6) |
| B-153 | (I) | (C.2.7) |
| B-154 | (I) | (D.1.1) |
| B-155 | (I) | (D.1.2) |
| B-156 | (I) | (D.1.3) |
| B-157 | (I) | (D.1.4) |
| B-158 | (I) | (D.1.5) |
| B-159 | (I) | (D.1.6) |
| B-160 | (I) | (D.2.1) |
| B-161 | (I) | (D.2.2) |
| B-162 | (I) | (D.2.3) |
| B-163 | (I) | (D.2.4) |
| B-164 | (I) | (D.2.5) |
| B-165 | (I) | (D.2.6) |
| B-166 | (I) | (D.2.7) |
| B-167 | (I) | (E.1.1) |
| B-168 | (I) | (E.1.2) |
| B-169 | (I) | (E.1.3) |
| B-170 | (I) | (E.2.1) |
| B-171 | (I) | (E.2.2) |
| B-172 | (I) | (E.2.3) |
| B-173 | (I) | (E.2.4) |
| B-174 | (I) | (E.2.5) |
| B-175 | (I) | (E.2.6) |
| B-176 | (I) | (E.2.7) |
| B-177 | (I) | (E.2.8) |
| B-178 | (I) | (F.1.1) |
| B-179 | (I) | (F.1.2) |
| B-180 | (I) | (F.1.3) |
| B-181 | (I) | (F.1.4) |
| B-182 | (I) | (F.1.5) |
| B-183 | (I) | (F.1.6) |
| B-184 | (I) | (F.2.1) |
| B-185 | (I) | (G.1.1) |
| B-186 | (I) | (G.1.2) |
| B-187 | (I) | (G.1.3) |
| B-188 | (I) | (G.1.4) |
| B-189 | (I) | (G.2.1) |
| B-190 | (I) | (G.2.2) |
| B-191 | (I) | (G.2.3) |
| B-192 | (I) | (G.2.4) |
| B-193 | (I) | (G.2.5) |
| B-194 | (I) | (G.2.6) |
| B-195 | (I) | (G.2.7) |
| B-196 | (I) | (G.3.1) |
| B-197 | (I) | (G.3.2) |
| B-198 | (I) | (G.3.3) |
| B-199 | (I) | (G.3.4) |
| B-200 | (I) | (G.3.5) |
| B-201 | (I) | (G.3.6) |
| B-202 | (I) | (G.3.7) |
| B-203 | (I) | (G.3.8) |
| B-204 | (I) | (G.4.1) |
| B-205 | (I) | (G.5.1) |

TABLE B-continued

Mixtures comprising as active components one individual compound of the formula I (in column Co. 1), in particular compounds 1 to 38 as defined in table C and compounds II-1 to II-455 as defined in table B, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-206 | (I) | (G.5.2) |
| B-207 | (I) | (G.5.3) |
| B-208 | (I) | (H.1.1) |
| B-209 | (I) | (H.1.2) |
| B-210 | (I) | (H.1.3) |
| B-211 | (I) | (H.1.4) |
| B-212 | (I) | (H.1.5) |
| B-213 | (I) | (H.1.6) |
| B-214 | (I) | (H.2.1) |
| B-215 | (I) | (H.2.2) |
| B-216 | (I) | (H.2.3) |
| B-217 | (I) | (H.2.4) |
| B-218 | (I) | (H.2.5) |
| B-219 | (I) | (H.2.6) |
| B-220 | (I) | (H.2.7) |
| B-221 | (I) | (H.2.8) |
| B-222 | (I) | (H.2.9) |
| B-223 | (I) | (H.3.1) |
| B-224 | (I) | (H.3.2) |
| B-225 | (I) | (H.3.3) |
| B-226 | (I) | (H.3.4) |
| B-227 | (I) | (H.3.5) |
| B-228 | (I) | (H.3.6) |
| B-229 | (I) | (H.3.7) |
| B-230 | (I) | (H.3.8) |
| B-231 | (I) | (H.3.9) |
| B-232 | (I) | (H.3.10) |
| B-233 | (I) | (H.3.11) |
| B-234 | (I) | (H.4.1) |
| B-235 | (I) | (H.4.2) |
| B-236 | (I) | (H.4.3) |
| B-237 | (I) | (H.4.4) |
| B-238 | (I) | (H.4.5) |
| B-239 | (I) | (H.4.6) |
| B-240 | (I) | (H.4.7) |
| B-241 | (I) | (H.4.8) |
| B-242 | (I) | (H.4.9) |
| B-243 | (I) | (H.4.10) |
| B-244 | (I) | (I.1.1) |
| B-245 | (I) | (I.1.2) |
| B-246 | (I) | (I.2.1) |
| B-247 | (I) | (I.2.2) |
| B-248 | (I) | (I.2.3) |
| B-249 | (I) | (I.2.4) |
| B-250 | (I) | (I.2.5) |
| B-251 | (I) | (J.1.1) |
| B-252 | (I) | (J.1.2) |
| B-253 | (I) | (J.1.3) |
| B-254 | (I) | (J.1.4) |
| B-255 | (I) | (J.1.5) |
| B-256 | (I) | (J.1.6) |
| B-257 | (I) | (J.1.7) |
| B-258 | (I) | (J.1.8) |
| B-259 | (I) | (J.1.9) |
| B-260 | (I) | (J.1.10) |
| B-261 | (I) | (K.1.1) |
| B-262 | (I) | (K.1.2) |
| B-263 | (I) | (K.1.3) |
| B-264 | (I) | (K.1.4) |
| B-265 | (I) | (K.1.5) |
| B-266 | (I) | (K.1.6) |
| B-267 | (I) | (K.1.7) |
| B-268 | (I) | (K.1.8) |
| B-269 | (I) | (K.1.9) |
| B-270 | (I) | (K.1.10) |
| B-271 | (I) | (K.1.11) |
| B-272 | (I) | (K.1.12) |
| B-273 | (I) | (K.1.13) |
| B-274 | (I) | (K.1.14) |
| B-275 | (I) | (K.1.15) |
| B-276 | (I) | (K.1.16) |
| B-277 | (I) | (K.1.17) |
| B-278 | (I) | (K.1.18) |
| B-279 | (I) | (K.1.19) |
| B-280 | (I) | (K.1.20) |
| B-281 | (I) | (K.1.21) |
| B-282 | (I) | (K.1.22) |
| B-283 | (I) | (K.1.23) |
| B-284 | (I) | (K.1.24) |
| B-285 | (I) | (K.1.25) |
| B-286 | (I) | (K.1.26) |
| B-287 | (I) | (K.1.27) |
| B-288 | (I) | (K.1.28) |
| B-289 | (I) | (K.1.29) |
| B-290 | (I) | (K.1.30) |
| B-291 | (I) | (K.1.31) |
| B-292 | (I) | (K.1.32) |
| B-293 | (I) | (K.1.33) |
| B-294 | (I) | (K.1.34) |
| B-295 | (I) | (K.1.35) |
| B-296 | (I) | (K.1.36) |
| B-297 | (I) | (K.1.37) |
| B-298 | (I) | (K.1.38) |
| B-299 | (I) | (K.1.39) |
| B-300 | (I) | (K.1.40) |
| B-301 | (I) | (K.1.41) |
| B-302 | (I) | (K.1.42) |
| B-303 | (I) | (K.1.43) |
| B-304 | (I) | (K.1.44) |
| B-305 | (I) | (K.1.45) |
| B-306 | (I) | (K.1.47) |
| B-307 | (I) | (M.1.1) |
| B-308 | (I) | (M.1.2) |
| B-309 | (I) | (M.1.3) |
| B-310 | (I) | (M.1.4) |
| B-311 | (I) | (M.1.5) |
| B-312 | (I) | (M.1.6) |
| B-313 | (I) | (M.1.7) |
| B-314 | (I) | (M.1.8) |
| B-315 | (I) | (M.1.9) |
| B-316 | (I) | (M.1.10) |
| B-317 | (I) | (M.1.11) |
| B-318 | (I) | (M.1.12) |
| B-319 | (I) | (M.1.13) |
| B-320 | (I) | (M.1.14) |
| B-321 | (I) | (M.1.15) |
| B-322 | (I) | (M.1.16) |
| B-323 | (I) | (M.1.17) |
| B-324 | (I) | (M.1.18) |
| B-325 | (I) | (M.1.19) |
| B-326 | (I) | (M.1.20) |
| B-327 | (I) | (M.1.21) |
| B-328 | (I) | (M.1.22) |
| B-329 | (I) | (M.1.23) |
| B-330 | (I) | (M.1.24) |
| B-331 | (I) | (M.1.25) |
| B-332 | (I) | (M.1.26) |
| B-333 | (I) | (M.1.27) |
| B-334 | (I) | (M.1.28) |
| B-335 | (I) | (M.1.29) |
| B-336 | (I) | (M.1.30) |
| B-337 | (I) | (M.1.31) |
| B-338 | (I) | (M.1.32) |
| B-339 | (I) | (M.1.33) |
| B-340 | (I) | (M.1.34) |
| B-341 | (I) | (M.1.35) |
| B-342 | (I) | (M.1.36) |
| B-343 | (I) | (M.1.37) |
| B-344 | (I) | (M.1.38) |
| B-345 | (I) | (M.1.39) |

TABLE B-continued

Mixtures comprising as active components one individual compound of the formula I (in column Co. 1), in particular compounds 1 to 38 as defined in table C and compounds II-1 to II-455 as defined in table B, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-346 | (I) | (M.1.40) |
| B-347 | (I) | (M.1.41) |
| B-348 | (I) | (M.1.42) |
| B-349 | (I) | (M.1.43) |
| B-350 | (I) | (M.1.44) |
| B-351 | (I) | (M.1.45) |
| B-352 | (I) | (M.1.46) |
| B-353 | (I) | (M.1.47) |
| B-354 | (I) | (M.1.48) |
| B-355 | (I) | (M.1.49) |
| B-356 | (I) | (M.1.50) |
| B-357 | (I) | (N.1.1) |
| B-358 | (I) | (N.1.2) |
| B-359 | (I) | (N.1.3) |
| B-360 | (I) | (N.1.4) |
| B-361 | (I) | (N.1.5) |
| B-362 | (I) | (N.2.1) |
| B-363 | (I) | (N.2.2) |
| B-364 | (I) | (N.2.3) |
| B-365 | (I) | (N.3.1) |
| B-366 | (I) | (N.3.2) |
| B-367 | (I) | (N.3.3) |
| B-368 | (I) | (N.3.4) |
| B-369 | (I) | (N.4.1) |
| B-370 | (I) | (N.5.1) |
| B-371 | (I) | (N.6.1) |
| B-372 | (I) | (N.6.2) |
| B-373 | (I) | (N.6.3) |
| B-374 | (I) | (N.6.4) |
| B-375 | (I) | (N.6.5) |
| B-376 | (I) | (N.7.1) |
| B-377 | (I) | (N.7.2) |
| B-378 | (I) | (N.7.3) |
| B-379 | (I) | (N.8.1) |
| B-380 | (I) | (N.9.1) |
| B-381 | (I) | (N.10.1) |
| B-382 | (I) | (N.10.2) |
| B-383 | (I) | (N.10.3) |
| B-384 | (I) | (N.10.4) |
| B-385 | (I) | (N.10.5) |
| B-386 | (I) | (N.11.1) |
| B-387 | (I) | (N.12.1) |
| B-388 | (I) | (N.12.2) |
| B-389 | (I) | (N.12.3) |
| B-390 | (I) | (N.12.4) |
| B-391 | (I) | (N.13.1) |
| B-392 | (I) | (N.13.2) |
| B-393 | (I) | (N.13.3) |
| B-394 | (I) | (N.13.4) |
| B-395 | (I) | (N.13.5) |
| B-396 | (I) | (N.13.6) |
| B-397 | (I) | (N.13.7) |
| B-398 | (I) | (N.13.8) |
| B-399 | (I) | (N.13.9) |
| B-400 | (I) | (N.14.1) |
| B-401 | (I) | (N.14.2) |
| B-402 | (I) | (N.14.3) |
| B-403 | (I) | (N.15.1) |
| B-404 | (I) | (N.16.1) |
| B-405 | (I) | (N.16.2) |
| B-406 | (I) | (N.17.1) |
| B-407 | (I) | (N.17.2) |
| B-408 | (I) | (N.17.3) |
| B-409 | (I) | (N.17.4) |
| B-410 | (I) | (N.17.5) |
| B-411 | (I) | (N.17.6) |
| B-412 | (I) | (N.17.7) |
| B-413 | (I) | (N.17.8) |
| B-414 | (I) | (N.17.9) |
| B-415 | (I) | (N.17.10) |
| B-416 | (I) | (N.17.11) |
| B-417 | (I) | (N.17.12) |
| B-418 | (I) | (O.1.1) |
| B-419 | (I) | (O.1.2) |
| B-420 | (I) | (O.1.3) |
| B-421 | (I) | (O.1.4) |
| B-422 | (I) | (O.1.5) |
| B-423 | (I) | (O.1.6) |
| B-424 | (I) | (O.1.7) |
| B-425 | (I) | (O.1.8) |
| B-426 | (I) | (O.1.9) |
| B-427 | (I) | (O.1.10) |
| B-428 | (I) | (O.1.11) |
| B-429 | (I) | (O.1.12) |
| B-430 | (I) | (O.1.13) |
| B-431 | (I) | (O.1.14) |
| B-432 | (I) | (O.1.15) |
| B-433 | (I) | (O.1.16) |
| B-434 | (I) | (O.1.17) |
| B-435 | (I) | (O.1.18) |
| B-436 | (I) | (O.1.19) |
| B-437 | (I) | (O.1.20) |
| B-438 | (I) | (O.1.21) |
| B-439 | (I) | (O.1.22) |
| B-440 | (I) | (O.1.23) |
| B-441 | (I) | (O.1.24) |
| B-442 | (I) | (O.1.25) |
| B-443 | (I) | (O.1.26) |
| B-444 | (I) | (O.1.27) |
| B-445 | (I) | (O.1.28) |
| B-446 | (I) | (O.1.29) |
| B-447 | (I) | (O.1.30) |
| B-448 | (I) | (O.1.31) |
| B-449 | (I) | (O.1.32) |
| B-450 | (I) | (O.1.33) |
| B-451 | (I) | (O.1.34) |
| B-452 | (I) | (O.1.35) |
| B-453 | (I) | (O.1.36) |
| B-454 | (I) | (O.1.37) |
| B-455 | (I) | (O.1.38) |
| B-456 | (I) | (O.2.1) |
| B-457 | (I) | (O.2.2) |
| B-458 | (I) | (O.2.3) |
| B-459 | (I) | (O.2.4) |
| B-460 | (I) | (O.2.5) |
| B-461 | (I) | (O.2.6) |
| B-462 | (I) | (O.2.7) |
| B-463 | (I) | (O.2.8) |
| B-464 | (I) | (O.2.9) |
| B-465 | (I) | (O.2.10) |
| B-466 | (I) | (O.2.11) |
| B-467 | (I) | (O.2.12) |
| B-468 | (I) | (O.2.13) |
| B-469 | (I) | (O.2.14) |
| B-470 | (I) | (O.2.15) |
| B-471 | (I) | (O.2.16) |
| B-472 | (I) | (O.3.1) |
| B-473 | (I) | (O.3.2) |
| B-474 | (I) | (O.3.3) |
| B-475 | (I) | (O.3.4) |
| B-476 | (I) | (O.3.5) |
| B-477 | (I) | (O.3.6) |
| B-478 | (I) | (O.3.7) |
| B-479 | (I) | (O.3.8) |
| B-480 | (I) | (O.3.9) |
| B-481 | (I) | (O.3.10) |
| B-482 | (I) | (O.3.11) |
| B-483 | (I) | (O.3.12) |
| B-484 | (I) | (O.3.13) |
| B-485 | (I) | (O.3.14) |

TABLE B-continued

Mixtures comprising as active components one individual compound of the formula I (in column Co. 1), in particular compounds 1 to 38 as defined in table C and compounds II-1 to II-455 as defined in table B, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-486 | (I) | (O.3.15) |
| B-487 | (I) | (O.3.16) |
| B-488 | (I) | (O.3.17) |
| B-489 | (I) | (O.3.18) |
| B-490 | (I) | (O.3.19) |
| B-491 | (I) | (O.3.20) |
| B-492 | (I) | (O.3.21) |
| B-493 | (I) | (O.3.22) |
| B-494 | (I) | (O.3.23) |
| B-495 | (I) | (O.3.24) |
| B-496 | (I) | (O.3.25) |
| B-497 | (I) | (O.3.26) |
| B-498 | (I) | (O.3.27) |
| B-499 | (I) | (O.4.1) |
| B-500 | (I) | (O.4.2) |
| B-501 | (I) | (O.4.3) |
| B-502 | (I) | (O.4.4) |
| B-503 | (I) | (O.4.5) |
| B-504 | (I) | (O.4.6) |
| B-505 | (I) | (O.4.7) |
| B-506 | (I) | (O.4.8) |
| B-507 | (I) | (O.4.9) |
| B-508 | (I) | (O.4.10) |
| B-509 | (I) | (O.4.11) |
| B-510 | (I) | (O.4.12) |
| B-511 | (I) | (O.4.13) |
| B-512 | (I) | (O.4.14) |
| B-513 | (I) | (O.4.15) |
| B-514 | (I) | (O.4.16) |
| B-515 | (I) | (O.4.17) |
| B-516 | (I) | (O.4.18) |
| B-517 | (I) | (O.4.19) |
| B-518 | (I) | (O.4.20) |
| B-519 | (I) | (O.4.21) |
| B-520 | (I) | (O.4.22) |
| B-521 | (I) | (O.4.23) |
| B-522 | (I) | (O.4.24) |
| B-523 | (I) | (O.5.1) |
| B-524 | (I) | (O.5.2) |
| B-525 | (I) | (O.5.3) |
| B-526 | (I) | (O.5.4) |
| B-527 | (I) | (O.5.5) |
| B-528 | (I) | (O.5.6) |
| B-529 | (I) | (O.5.7) |
| B-530 | (I) | (O.5.8) |
| B-531 | (I) | (O.5.9) |
| B-532 | (I) | (O.6.1) |
| B-533 | (I) | (O.6.2) |
| B-534 | (I) | (O.6.3) |
| B-535 | (I) | (O.6.4) |
| B-536 | (I) | (O.6.5) |
| B-537 | (I) | (O.6.6) |
| B-538 | (I) | (O.6.7) |
| B-539 | (I) | (O.7.1) |
| B-540 | (I) | (O.7.2) |
| B-541 | (I) | (O.7.3) |
| B-542 | (I) | (O.7.4) |
| B-543 | (I) | (O.7.5) |
| B-544 | (I) | (O.7.6) |
| B-545 | (I) | (O.8.1) |
| B-546 | (I) | (O.8.2) |
| B-547 | (I) | (O.8.3) |
| B-548 | (I) | (O.8.4) |
| B-549 | (I) | (O.8.5) |
| B-550 | (I) | (O.9.1) |
| B-551 | (I) | (O.9.2) |
| B-552 | (I) | (O.9.3) |
| B-553 | (I) | (O.10.1) |
| B-554 | (I) | (O.11.1) |
| B-555 | (I) | (O.11.2) |
| B-556 | (I) | (O.11.3) |
| B-557 | (I) | (O.11.4) |
| B-558 | (I) | (O.12.1) |
| B-559 | (I) | (O.13.1) |
| B-560 | (I) | (O.14.1) |
| B-561 | (I) | (O.14.2) |
| B-562 | (I) | (O.15.1) |
| B-563 | (I) | (O.15.2) |
| B-564 | (I) | (O.15.3) |
| B-565 | (I) | (O.15.4) |
| B-566 | (I) | (O.15.5) |
| B-567 | (I) | (O.15.6) |
| B-568 | (I) | (O.15.7) |
| B-569 | (I) | (O.15.8) |
| B-570 | (I) | (O.15.9) |
| B-571 | (I) | (O.15.10) |
| B-572 | (I) | (O.15.11) |
| B-573 | (I) | (O.16.1) |
| B-574 | (I) | (O.16.2) |
| B-575 | (I) | (O.16.3) |
| B-576 | (I) | (O.16.4) |
| B-577 | (I) | (O.16.5) |
| B-578 | (I) | (O.16.6) |
| B-579 | (I) | (O.17.1) |
| B-580 | (I) | (O.18.1) |
| B-581 | (I) | (O.18.2) |
| B-582 | (I) | (O.18.3) |
| B-583 | (I) | (O.18.4) |
| B-584 | (I) | (O.18.5) |
| B-585 | (I) | (O.19.1) |
| B-586 | (I) | (O.20.1) |
| B-587 | (I) | (O.20.2) |
| B-588 | (I) | (O.20.3) |
| B-589 | (I) | (O.21.1) |
| B-590 | (I) | (O.21.2) |
| B-591 | (I) | (O.21.3) |
| B-592 | (I) | (O.21.4) |
| B-593 | (I) | (O.21.5) |
| B-594 | (I) | (O.21.6) |
| B-595 | (I) | (O.21.7) |
| B-596 | (I) | (O.22.1) |
| B-597 | (I) | (O.22.2) |
| B-598 | (I) | (O.22.3) |
| B-599 | (I) | (O.22.4) |
| B-600 | (I) | (O.23.1) |
| B-601 | (I) | (O.23.2) |
| B-602 | (I) | (O.23.3) |
| B-603 | (I) | (O.24.1) |
| B-604 | (I) | (O.24.2) |
| B-605 | (I) | (O.24.3) |
| B-606 | (I) | (O.24.4) |
| B-607 | (I) | (O.24.5) |
| B-608 | (I) | (O.25.1) |
| B-609 | (I) | (O.25.2) |
| B-610 | (I) | (O.26.1) |
| B-611 | (I) | (O.26.2) |
| B-612 | (I) | (O.26.3) |
| B-613 | (I) | (O.26.4) |
| B-614 | (I) | (O.26.5) |
| B-615 | (I) | (O.26.6) |
| B-616 | (I) | (O.26.7) |
| B-617 | (I) | (O.26.8) |
| B-618 | (I) | (O.26.9) |
| B-619 | (I) | (O.26.10) |
| B-620 | (I) | (O.26.11) |
| B-621 | (I) | (O.26.12) |
| B-622 | (I) | (O.26.13) |
| B-623 | (I) | (O.26.14) |
| B-624 | (I) | (O.26.15) |
| B-625 | (I) | (O.26.16) |

TABLE B-continued

Mixtures comprising as active components one individual compound of the formula I (in column Co. 1), in particular compounds 1 to 38 as defined in table C and compounds II-1 to II-455 as defined in table B, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-626 | (I) | (O.26.17) |
| B-627 | (I) | (O.26.18) |
| B-628 | (I) | (O.27.1) |
| B-629 | (I) | (O.27.2) |
| B-630 | (I) | (O.27.3) |
| B-631 | (I) | (O.27.4) |
| B-632 | (I) | (O.27.5) |
| B-633 | (I) | (O.27.6) |
| B-634 | (I) | (O.27.7) |
| B-635 | (I) | (O.27.8) |
| B-636 | (I) | (O.27.9) |
| B-637 | (I) | (O.27.10) |
| B-638 | (I) | (O.27.11) |
| B-639 | (I) | (O.27.12) |
| B-640 | (I) | (O.27.13) |
| B-641 | (I) | (O.27.14) |
| B-642 | (I) | (O.27.15) |
| B-643 | (I) | (O.27.16) |
| B-644 | (I) | (O.27.17) |
| B-645 | (I) | (O.27.18) |
| B-646 | (I) | (O.27.19) |
| B-647 | (I) | (O.27.20) |
| B-648 | (I) | (O.27.21) |
| B-649 | (I) | (O.27.22) |
| B-650 | (I) | (O.27.23) |
| B-651 | (I) | (O.27.24) |
| B-652 | (I) | (O.27.25) |
| B-653 | (I) | (O.27.26) |
| B-654 | (I) | (O.27.27) |
| B-655 | (I) | (O.27.28) |
| B-656 | (I) | (O.27.29) |
| B-657 | (I) | (O.27.30) |
| B-658 | (I) | (O.27.31) |
| B-659 | (I) | (O.27.32) |
| B-660 | (I) | (O.27.33) |
| B-661 | (I) | (O.27.34) |
| B-662 | (I) | (O.27.35) |
| B-663 | (I) | (O.27.36) |
| B-664 | (I) | (O.27.37) |
| B-665 | (I) | (O.27.38) |
| B-666 | (I) | (O.27.39) |
| B-667 | (I) | (O.27.40) |
| B-668 | (I) | (O.27.41) |
| B-669 | (I) | (O.27.42) |
| B-670 | (I) | (O.27.43) |
| B-671 | (I) | (O.27.44) |
| B-672 | (I) | (O.27.45) |
| B-673 | (I) | (O.27.46) |
| B-674 | (I) | (O.27.47) |
| B-675 | (I) | (O.27.48) |
| B-676 | (I) | (O.27.49) |
| B-677 | (I) | (O.27.50) |
| B-678 | (I) | (O.27.51) |
| B-679 | (I) | (O.27.52) |
| B-680 | (I) | (O.27.53) |
| B-681 | (I) | (O.27.54) |
| B-682 | (I) | (O.27.55) |
| B-683 | (I) | (O.27.56) |
| B-684 | (I) | (O.27.57) |
| B-685 | (I) | (O.27.58) |
| B-686 | (I) | (O.27.59) |
| B-687 | (I) | (O.27.60) |
| B-688 | (I) | (O.27.61) |
| B-689 | (I) | (O.27.62) |
| B-690 | (I) | (O.27.63) |
| B-691 | (I) | (O.27.64) |
| B-692 | (I) | (O.27.65) |
| B-693 | (I) | (O.27.66) |
| B-694 | (I) | (O.27.67) |
| B-695 | (I) | (O.27.68) |
| B-696 | (I) | (O.27.69) |
| B-697 | (I) | (O.27.70) |
| B-698 | (I) | (O.27.71) |
| B-699 | (I) | (O.27.72) |
| B-700 | (I) | (O.27.73) |
| B-701 | (I) | (O.27.74) |
| B-702 | (I) | (O.27.75) |
| B-703 | (I) | (O.27.76) |
| B-704 | (I) | (O.27.77) |
| B-705 | (I) | (O.27.78) |
| B-706 | (I) | (O.27.79) |
| B-707 | (I) | (O.27.80) |
| B-708 | (I) | (O.27.81) |
| B-709 | (I) | (O.27.82) |
| B-710 | (I) | (O.27.83) |
| B-711 | (I) | (O.27.84) |
| B-712 | (I) | (O.27.85) |
| B-713 | (I) | (O.27.86) |
| B-714 | (I) | (O.27.87) |
| B-715 | (I) | (O.27.88) |
| B-716 | (I) | (O.27.89) |
| B-717 | (I) | (O.27.90) |
| B-718 | (I) | (O.27.91) |
| B-719 | (I) | (O.27.92) |
| B-720 | (I) | (O.27.93) |
| B-721 | (I) | (O.27.94) |
| B-722 | (I) | (O.27.95) |
| B-723 | (I) | (O.27.96) |
| B-724 | (I) | (O.27.97) |
| B-725 | (I) | (O.27.98) |
| B-726 | (I) | (O.27.99) |
| B-727 | (I) | (O.27.100) |

The mixtures of active substances can be prepared as compositions comprising besides the active ingredients at least one inert ingredient (auxiliary) by usual means, e. g. by the means given for the compositions of compounds I. Concerning usual ingredients of such compositions reference is made to the explanations given for the compositions containing compounds I. The mixtures of active substances according to the present invention are suitable as fungicides, as are the compounds I. They are distinguished by an outstanding effectiveness against a broad spectrum of phytopathogenic fungi, especially from the classes of the Ascomycetes, Basidiomycetes, *Deuteromycetes* and Peronosporomycetes (syn. Oomycetes). In addition, it is refered to the explanations regarding the fungicidal activity of the compounds and the compositions containing compounds I, respectively.

I. SYNTHESIS EXAMPLES

With due modification of the starting compounds, the procedures shown in the synthesis examples below were used to obtain further compounds I. The resulting compounds, together with physical data, are listed in Table C below.

Example I.1: 4-[(Z)—N'-hydroxycarbamimidoyl] benzoic acid

To a solution of the 4-cyano benzoic acid (500 g, 1.0 eq) in a mixture of ethanol and water (5 L/2 L) was added hydroxylamine hydrochloride salt (495 g, 2.0 eq.) and potassium carbonate (751 g, 1.5 eq.). The resulting mixture was treated with 8-hydroxyquinoline (6.5 g, 0.1 eq.) and heated under reflux until HPLC indicated complete conversion of the starting material. After cooling to ambient temperature, water was added and the resulting precipitate was collected and dried to afford the title compound sufficiently pure to be used directly without further purification.

Example I.2: 4-[5-(trifluoromethyl)-1,2,4-oxadiazol-3-yl]benzoic acid

A solution of the amidine as obtained from example I.1 (200 g, 1.0 eq) in tetrahydrofuran (2.5 L) was treated with trifluoroacetic anhydride (350 g, 1.5 eq). The resulting mixture was stirred overnight at ambient temperature, before it was diluted with methyl tert-butylether and washed with a saturated aqueous solution of sodium bicarbonate. The organic layer was freed from solvent under reduced pressure to afford a crude product that was recrystallized from di-iso propyl ether to furnish the title compound as light brown solid (220 g, 76%).
$^1$H NMR (400 MHz, DMSO-d$^6$, 298 K): δ [ppm]=13.40 (br. s, 1H), 8.22-8.10 (m, 4H).

Example I.3: 4-[5-(trifluoromethyl)-1,2,4-oxadiazol-3-yl]benzoyl chloride

A 250 mL round-bottom flask was charged with the carboxylic acid of example I.2 (20 g, 1.0 eq) and thionyl chloride was added dropwise (50 mL, 10 eq). To the suspension were added 20 drops of N,N-dimethylformamide and the mixture was warmed to gentle reflux for 2 hours.

When HPLC indicated complete conversion of the starting material, the mixture was cooled to room temperature and all volatiles were removed under reduced pressure. The residue was taken up in toluene and co-evaporated to remove residual thionyl chloride. The title compound was isolated as light brown solid (20.7 g, 97%).
$^1$H NMR (400 MHz, CDCl$_3$, 298 K): δ [ppm]=8.35-8.25 (m, 4H).

Example I.4: N-(2-hydroxy-1-methyl-propyl)-4-[5-(trifluoromethyl)-1,2,4-oxadiazol-3-yl]benzamide A solution of the acid chloride of example I.3 (2.00 g, 1.0 eq) in dichloromethane (10 mL) was added dropwise to a solution of 3-amino-2-butanol (709 mg, 1.1 eq) and triethylamine in dichloromethane (20 mL). The mixture was stirred at ambient temperature until HPLC showed complete conversion of the starting material. The reaction was quenched by adding diluted aqueous hydrochloric acid (1 M) and the product was extracted into dichloromethane. The combined organic layers were washed with brine, dried over sodium sulfate and freed from solvent under reduced pressure. The crude product solidified upon standing over night to yield the title compound as light brown solid (2.09 g, 83%, mp 147° C.) sufficiently pure to be used without further purification.

Example I.5: N-(1-methyl-2-oxo-propyl)-4-[5-(trifluoromethyl)-1,2,4-oxadiazol-3-yl]benzamide To a solution of the product of example 1.4 (1.84 g, 1.0 eq) in dichloromethane (60 mL) was added pyridinium chlorochromate (2.41 g, 2.0 eq) in several portions. The mixture turned dark immediately and was stirred at about room temperature overnight before it was adsorbed to silica gel. Purification by column chromatography afforded the desired ketone as yellow solid (1.12 g, 61%, mp 120° C.).
$^1$H NMR (400 MHz, CDCl$_3$, 298 K): δ [ppm]=8.22 (d, 2H), 7.95 (d, 2H), 7.10 (d, 1H), 4.85-4.75 (d, 1H), 2.27 (s, 3H), 1.50 (d, 3H).

Example I.6: N-[(2E)-2-methoxyimino-1-methyl-propyl]-4-[5-(trifluoromethyl)-1,2,4-oxadiazol-3-yl]benzamide An aqueous solution of O-methylhydroxylamine hydrochloride (280 mg in 3 mL water, 1.1 eq.) was treated with pyridine (36 mg, 1.5 eq.), before a solution of the ketone product of example I.5 (100 mg, 1.0 eq.) in methanol (10 mL) was added dropwise at ambient temperature. The mixture was stirred until HPLC indicated complete conversion. Water was added and the pH was adjusted to ca. 4-5 by adding diluted aqueous hydrochloric acid. The aqueous layer was extracted with methyl tert-butylether (3×25 mL). The combined organic extracts were successively washed twice with diluted aqueous hydrochloric acid and water and dried over sodium sulfate. Removal of the solvent under reduced pressure furnished a crude product that was further purified by column chromatography. The (E)-isomer of the title compound was exclusively isolated as white solid (80.5 mg, 74%, mp 145° C.).
$^1$H NMR (400 MHz, CDCl$_3$, 298 K): δ [ppm]=8.22 (d, 2H), 7.95 (d, 2H), 7.10 (d, 1H), 4.75-4.65 (m, 1H), 3.90 (s, 3H), 1.90 (s, 3H), 1.45 (d, 3H).

TABLE C

Compounds of formula 1

| ex. no | Formula* | R | R$^1$ | R$^2$ | m. p. [° C.]; **R$_t$ [min] |
|---|---|---|---|---|---|
| 1 | I.2.1 | H | CH$_3$ | H | 138° C.; 1.16 min |
| 2 | I.2.1 | H | CH$_2$CH$_3$ | H | 123° C.; 1.20 min |
| 3 | I.2.2.a | CH$_2$CH$_3$ | CH$_3$ | —(C=O)OCH$_2$CH$_3$ | oil; 1.25 min |
| 4 | I.2.2.b | H | CH(CH$_3$)$_2$ | CH$_3$ | 137° C.; 1.31 min |
| 5 | I.2.2.b | H | C(CH$_3$)$_3$ | CH$_3$ | 98° C.; 1.38 min |
| 6 | I.2.2.b | H | CH$_2$CH=CH$_2$ | CH$_3$ | 133° C.; 1.27 min |
| 7 | I.2.2.b | H | CH$_2$C≡CH | CH$_3$ | 135° C.; 1.21 min |
| 8 | I.2.2.a | H | CH$_2$CH$_3$ | H | 143° C.; 1.12 min |
| 9 | I.2.2.a | H | CH$_3$ | H | oil; 1.09 min |
| 10 | I.2.2.b | H | CH$_3$ | CH$_3$ | 145° C.; 1.19 min |
| 11 | I.2.2.c | H | CH(CH$_3$)$_2$ | H | 123° C.; 1.31 min |
| 12 | I.2.2.c | H | CH$_3$ | H | 87° C.; 1.19 min |
| 13 | I.2.2.a | H | CH$_3$ | CH$_3$ | 149° C.; 1.13 min |

TABLE C-continued

Compounds of formula 1

| ex. no | Formula* | R | $R^1$ | $R^2$ | m. p. [° C.]; **$R_t$ [min] |
|---|---|---|---|---|---|
| 14 | I.2.2.a | H | $CH_2CH_3$ | $CH_3$ | 141° C.; 1.17 min |
| 15 | I.2.2.a | H | $CH_2CH=CH_2$ | $CH_3$ | 123° C.; 1.19 min |
| 16 | I.2.2.c | H | $CH_2CH_3$ | H | 105° C.; 1.25 min |
| 17 | I.2.2.c | H | $CH_2CH=CH_2$ | H | 93° C.; 1.27 min |
| 18 | I.2.2.c | H | $C(CH_3)_3$ | H | 139° C.; 1.37 min |
| 19 | I.2.2.b | H | $CH_2CH_3$ | $CH_3$ | 132° C.; 1.22 min |
| 20 | I.2.2.b | H | $C(CH_3)_3$ | $CH_3$ | 78° C.; 1.39 min |
| 21 | I.2.2.b | H | $CH_2CH=CH_2$ | $CH_3$ | 127° C.; 1.24 min |
| 22 | I.2.2.b | H | $CH(CH_3)_2$ | $CH_3$ | 137° C.; 1.28 min |
| 23 | I.2.2.c | H | $CH_3$ | $CH_3$ | 126° C.; 1.24 min |
| 24 | I.2.2.d | H | $CH_3$ | H | 132° C.; 1.10 min |
| 25 | I.2.2.c | H | $CH_2CH_3$ | $CH_3$ | 100° C.; 1.30 min |
| 26 | I.2.2.c | H | $CH_2CH=CH_2$ | $CH_3$ | 102° C.; 1.32 min |
| 27 | I.2.2.c | H | $CH(CH_3)_2$ | $CH_3$ | 113° C.; 1.37 min |
| 28 | I.2.2.c | H | $C(CH_3)_3$ | $CH_3$ | 101° C.; 1.43 min |
| 29 | I.2.2.d | H | $CH_2CH_3$ | H | 107° C.; 1.15 min |
| 30 | I.2.2.d | H | $CH_2CH=CH_2$ | H | 118° C.; 1.18 min |
| 31 | I.2.2.d | H | $CH(CH_3)_2$ | H | 122° C.; 1.23 min |
| 32 | I.2.2.d | H | $C(CH_3)_3$ | H | 150° C.; 1.29 min |
| 33 | I.2.3.a | H | $CH_3$ | $CH_3$ | 109° C.; 1.10 min |
| 34 | I.2.3.a | H | $CH_2CH_3$ | $CH_3$ | oil; 1.15 min |
| 35 | I.2.3.a | H | $CH(CH_3)_2$ | $CH_3$ | 80° C.; 1.21 min |
| 36 | I.2.3.a | H | $C(CH_3)_3$ | $CH_3$ | oil; 1.29 min |
| 37 | I.2.3.a | H | $CH_2CH=CH_2$ | $CH_3$ | 66° C.; 1.23 min |
| 38 | I.2.3.a | H | $CH_2C\equiv CH$ | $CH_3$ | 71° C.; 1.17 min |
| 39 | I.2.3.b | H | $CH_2CH_3$ | $CH_3$ | 78° C. |
| 40 | I.2.3.b | H | $C(CH_3)_3$ | $CH_3$ | 114° C. |
| 41 | I.2.3.b | H | $CH_3$ | $CH_3$ | 98° C. |
| 42 | I.2.3.b | H | $CH(CH_3)_2$ | $CH_3$ | 75° C. |
| 43 | I.2.3.b | H | $CH_2CH=CH_2$ | $CH_3$ | 75° C. |
| 44 | I.2.3.b | H | $CH_2C\equiv CH$ | $CH_3$ | 96° C. |
| 45 | I.2.3.d | H | $CH_3$ | $CH_3$ | 102° C. |
| 46 | I.2.3.f | H | $CH_3$ | $CH_3$ | oil; 1.20 min |
| 47 | I.2.3.f | H | $CH_2CH_3$ | $CH_3$ | oil; 1.26 min |
| 48 | I.2.3.f | H | $CH_2CH=CH_2$ | $CH_3$ | oil; 1.283 min |
| 49 | I.2.3.d | H | $CH_2CH_3$ | $CH_3$ | 88° C. |
| 50 | I.2.3.d | H | $CH_2CH=CH_2$ | $CH_3$ | 56° C. |
| 51 | I.2.3.e | H | $CH_3$ | H | 100° C. |
| 52 | I.2.3.f | H | $CH_3$ | H | 123° C. |
| 53 | I.2.3.f | H | $CH_2CH_3$ | H | 112° C. |
| 54 | I.2.3.e | H | $CH_2CH_3$ | H | 68° C. |
| 55 | I.2.3.f | $CH_3$ | $CH_3$ | H | oil; 1.22 min |
| 56 | I.2.3.f | $CH_3$ | $CH_2CH_3$ | H | oil; 1.31 min |
| 57 | I.2.3.e | $CH_3$ | $CH_3$ | H | oil; 1.29 min |
| 58 | I.2.3.e | $CH_3$ | $CH_2CH_3$ | H | oil; 1.35 min |
| 59 | I.2.1 | H | $CH_2CH_3$ | $CH_3$ | 46° C. |
| 60 | I.2.1 | H | $CH_3$ | $CH_3$ | 138° C. |

*Formula refers to the respective subformula of formula I as defined herein m.p. = melting point.
**HPLC: High Performance Liquid Chromatography; HPLC-column Kinetex XB C18 1.7µ (50 × 2.1 mm); eluent: acetonitrile/water + 0.1% trifluoroacetic acid (gradient from 5/95 to 100/00 in 1.5 min at 60° C., flow gradient from 0.8 to 1.0 ml/min in 1.5 min). $R_t$: retention time in minutes.
MS: Quadrupol Electrospray Ionisation, 80 V (positive mode).

II. BIOLOGICAL EXAMPLES FOR FUNGICIDAL ACTIVITY

The fungicidal action of the compounds of formula I was demonstrated by the following experiments:

A. Glass House Trials

The spray solutions were prepared in several steps: The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to total volume of 100 ml. This stock solution was diluted with the described solvent-emulsifier-water mixture to the given concentration.

II.1) Curative Control of Soy Bean Rust on Soy Beans Caused by *Phakopsora pachyrhizi*

Leaves of pot-grown soy bean seedlings were inoculated with spores of *Phakopsora pachyrhizi* To ensure the success of the artificial inoculation, the plants were transferred to a humid chamber with a relative humidity of about 95% and 20 to 24° C. for 24 hours. The next day the plants were cultivated for 3 days in a greenhouse chamber at 23 to 27° C. and a relative humidity between 60 and 80%. Then the plants were sprayed to run-off with an aqueous suspension, containing the concentration of active ingredient or their mixture as described below. The plants were allowed to air-dry. Then the trial plants were cultivated for 14 days in a greenhouse chamber at 23 to 27° C. and a relative humidity between 60 and 80%. The extent of fungal attack on the leaves was visually assessed as % diseased leaf area. In this test, the plants which had been treated with 32 ppm of the active compounds 1, 2, 7, 8, 9, 10, 11, 12, 13, 14, 15, 16, 19, 22, 23, 24, 32, 33, 34, 35, 37, 38, 39, 41, 42, 43, 44, 45, 46, 47, 48, 49, 50, 51, 52, 54, 56 and 60 of Table C showed a diseased leaf area of at most 20%, whereas the untreated plants showed 90% diseased leaf area.

II.2) Protective Control of Soy Bean Rust on Soy Beans Caused by Phakopsora pachyrhizi Leaves of pot-grown soy bean seedlings were sprayed to run-off with an aqueous suspension, containing the concentration of active ingredient or their mixture as described below. The plants were allowed to air-dry. The trial plants were cultivated for 2 day in a greenhouse chamber at 23 to 27° C. and a relative humidity between 60 and 80%. Then the plants were inoculated with spores of Phakopsora pachyrhizi. To ensure the success the artificial inoculation, the plants were transferred to a humid chamber with a relative humidity of about 95% and 20 to 24° C. for 24 h. The trial plants were cultivated for fourteen days in a greenhouse chamber at 23 to 27° C. and a relative humidity between 60 and 80%. The extent of fungal attack on the leaves was visually assessed as % diseased leaf area.

In this test, the plants which had been treated with 32 ppm of the active compounds 1, 2, 4, 6, 7, 8, 9, 10, 11, 12, 13, 14, 15, 16, 17, 18, 19, 20, 21, 22, 23, 24, 26, 27, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60 of Table C showed a diseased leaf area of at most 18%, whereas the untreated plants showed 90% diseased leaf area.

II.3) Curative Control of Brown Rust on Wheat Caused by Puccinia recondita

The first two developed leaves of pot-grown wheat seedling were dusted with spores of Puccinia recondita. To ensure the success the artificial inoculation, the plants were transferred to a humid chamber without light and a relative humidity of 95 to 99% and 20 to 24° C. for 24 hours. The next day the plants were cultivated for 3 days in a greenhouse chamber at 20 to 24° C. and a relative humidity between 65 and 70%. Then the plants were sprayed to run-off with an aqueous suspension, containing the concentration of active ingredient or their mixture as described below. The plants were allowed to air-dry. Then the trial plants were cultivated for 8 days in a greenhouse chamber at 20 to 24° C. and a relative humidity between 65 and 70%. The extent of fungal attack on the leaves was visually assessed as % diseased leaf area.

In this test, the plants which had been treated with 63 ppm of the active compounds 2, 9, 10, 13, 14, 15, 24, 31, 32, 33, 39, 41, 45, 46, 47, 49, 50, 51, 52 and 54 of Table C showed a diseased leaf area of at most 17%, whereas the untreated plants showed 90% diseased leaf area.

II.4) Preventative Control of Brown Rust on Wheat Caused by Puccinia recondita

The first two developed leaves of pot-grown wheat seedling were sprayed to run-off with an aqueous suspension, containing the concentration of active ingredient or their mixture as described below. Seven days later the plants were inoculated with spores of Puccinia recondita. To ensure the success the artificial inoculation, the plants were transferred to a humid chamber without light and a relative humidity of 95 to 99% and 20 to 24° C. for 24 h. Then the trial plants were cultivated for 6 days in a greenhouse chamber at 20 to 24° C. and a relative humidity between 65 and 70%. The extent of fungal attack on the leaves was visually assessed as % diseased leaf area.

In this test, the plants which had been treated with 63 ppm of the active compounds 9, 10, 13, 14, 15, 24, 31, 33, 39, 41, 45, 46, 47, 49, 50, 51, 52 and 54 of Table C showed a diseased leaf area of at most 9%, whereas the untreated plants showed 90% diseased leaf area.

The invention claimed is:
1. A compound of formula I, or the N-oxides, or the agriculturally acceptable salts thereof

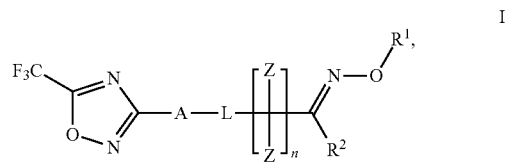

wherein:
A is a phenyl ring, wherein the phenyl ring is unsubstituted or substituted by 1, 2, 3 or 4 identical or different groups $R^A$; wherein
  $R^A$ is halogen, cyano, $diC_1$-$C_6$-alkylamino, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_5$-cycloalkyl or $C_3$-$C_5$-cycloalkoxy; and wherein any of the aliphatic or cyclic moieties are unsubstituted or substituted by 1, 2, 3, 4 or up to the maximum possible number of identical or different groups $R^a$,
    wherein
    $R^a$ is halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_4$-alkoxy-$C_1$-$C_4$-alkyl or $C_3$-$C_5$-cycloalkyl;
L is #-C(=X)—NR—, wherein # denotes the position to which the cyclic group A is attached to; and wherein X is O or S; and
  R is hydrogen, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkenyl, C(=O)-($C_1$-$C_6$-alkyl), C(=O)-($C_1$-$C_6$-alkoxy), phenyl-$C_1$-$C_4$-alkyl, heteroaryl-$C_1$-$C_4$-alkyl, phenyl, naphthyl or a 3- to 10-membered saturated, partially unsaturated or aromatic mono-or bicyclic heterocycle; wherein the heteroaryl group in heteroaryl-$C_1$-$C_4$-alkyl is a 5- or 6-membered aromatic heterocycle, wherein the ring member atoms of said 5- or 6-membered aromatic heterocycle include besides carbon atoms 1, 2, 3 or 4 heteroatoms selected from N, O and S as ring member atoms; and wherein the ring member atoms of said 3-to 10-membered saturated, partially unsaturated or aromatic mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and
    wherein any of the above-mentioned aliphatic or cyclic groups are unsubstituted or substituted by 1, 2, 3 or up to the maximum possible number of identical or different groups $R^{1a}$; wherein $R^{1a}$ is halogen, cyano, NO2, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_4$-alkylamino, $diC_1$-$C_4$-alkylamino, $C_1$-$C_6$-alkylthio, $C_1$-$C_6$-haloalkylthio, $C_3$-$C_8$-cycloalkyl, $NHSO_2$—$C_1$-$C_4$-alkyl, (C=O)—$C_1$-$C_4$-alkyl, C(=O)—$C_1$-$C_4$-alkoxy, $C_1$-$C_6$-alkyl sulfonyl, hydroxy$C_1$-$C_4$-alkyl, C(=O)—N2, C(=O)—NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, $diC_1$-$C_4$-alkylamino-$C_1$-$C_4$-alkyl, aminocarbonyl-$C_1$-$C_4$-alkyl or $C_1$-$C_4$-alkoxy-$C_1$-$C_4$-alkyl;

n is 0, 1, 2 or 3;

Z, which may be the same or different to any other Z, is hydrogen, halogen, $C_1$-$C_6$-alkyl, $C_1$-$C_6$-alkoxy, $C_1$-$C_6$-alkylthio, $C_2$-$C_6$-alkenyl, $C_2$-$C_6$-alkynyl, $C_3$-$C_8$-cycloalkyl, $C_3$-$C_8$-cycloalkenyl, phenyl-$C_1$-$C_4$-alkyl, heteroaryl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the aliphatic or cyclic groups are unsubstituted or substituted by 1, 2, 3, 4 or up to the maximum possible number of identical or different groups $R^{1a}$, or two radicals Z that are bound to the same carbon atom may form together with said carbon atom a $C_3$-$C_8$-cycloalkyl;

$R^1$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, phenyl-$C_1$-$C_4$-alkyl, or a three- to ten-membered saturated, partially unsaturated or aromatic mono- or bicyclic heterocyclyl which, in addition to carbon atoms, contains one to four heteroatoms from the group consisting of O, N and S as ring members; and wherein any of the above-mentioned aliphatic or cyclic groups are unsubstituted or substituted by 1, 2, 3 or up to the maximum possible number of identical or different groups $R^{1a}$, and $R^2$ is hydrogen, halogen, cyano, amino, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, C(=O)-($C_1$-$C_6$-alkyl), C(=O)-($C_1$-$C_6$-alkoxy), $C_1$-$C_4$-alkylamino, $diC_1$-$C_4$-alkylamino, phenyl-$C_1$-$C_4$-alkyl, heteroaryl-$C_1$-$C_4$-alkyl, phenyl, naphthyl or a 3- to 10-membered saturated, partially unsaturated or aromatic mono- or bicyclic heterocycle; wherein the heteroaryl group in heteroaryl-$C_1$-$C_4$-alkyl is a 5- or 6-membered aromatic heterocycle, wherein the ring member atoms of said 5- or 6-membered aromatic heterocycle include besides carbon atoms 1, 2, 3 or 4 heteroatoms selected from N, O and S as ring member atoms; and wherein the ring member atoms of said 3- to 10-membered saturated, partially unsaturated or aromatic mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein any of the above-mentioned aliphatic or cyclic groups are unsubstituted or substituted by 1, 2, 3 or up to the maximum possible number of identical or different groups $R^{1a}$.

2. The compound according to claim 1, wherein A is an unsubstituted phenyl ring.

3. The compound according to claim 1, wherein:
A is 1,4-phenylene;
L is #-C(=O)—NR—;
n is 0;
R is H;
$R^1$ is $CH_3$; and
$R^2$ is H.

4. The compound according to claim 1, wherein X is O.

5. The compound according to claim 1, wherein R is hydrogen or methyl.

6. The compound according to claim 1, wherein n is 0, 1 or 2.

7. The compound according to claim 6, wherein n is 1 or 2 and wherein Z, which may be the same or different to any other Z, is hydrogen, halogen, $C_1$-$C_4$-alkyl; or two radicals Z that are bound to the same carbon atom form together with said carbon atom a cyclopropyl.

8. The compound according to claim 1, wherein $R^1$ is $C_1$-$C_6$-alkyl or $C_2$-$C_6$-alkenyl or $C_2$-$C_6$-alkynyl.

9. The compound according to claim 1, wherein $R^2$ is hydrogen, $C_1$-$C_6$-alkyl or C(=O)-($C_1$-$C_6$-alkoxy).

10. The compound according to claim 9, wherein $R^2$ is hydrogen or methyl.

11. A mixture comprising at least one compound of formula I according to claim 1 and at least one further active substance selected from the group consisting of herbicides, safeners, fungicides, insecticides and plant growth regulators.

12. An agrochemical composition, which comprises an auxiliary and at least one compound of formula I according to claim 1 or a mixture according to claim 11.

13. An agrochemical composition according to claim 12 further comprising seed, wherein the amount of the compound of formula I is from 0.1 g to 10 kg per 100 kg of seed.

14. A method for combating phytopathogenic harmful fungi, which process comprises treating the fungi or the materials, plants, the soil or seeds to be protected against fungal attack, with an effective amount of at least one compound of formula I as defined in claim 1.

15. The method claim 14, wherein A is an unsubstituted phenyl ring.

16. The method claim 14, wherein:
A is 1,4-phenylene;
L is #-C(=O)—NR—;
n is 0;
R is H;
$R^1$ is $CH_3$; and
$R^2$ is H.

17. The method claim 14, wherein X is O.

18. The method claim 14, wherein R is hydrogen or methyl.

19. The method claim 14, wherein n is 0, 1 or 2.

20. The method claim 14, wherein n is 1 or 2 and wherein Z, which may be the same or different to any other Z, is hydrogen, halogen, $C_1$-$C_4$-alkyl; or two radicals Z that are bound to the same carbon atom form together with said carbon atom a cyclopropyl.

21. The method claim 14, wherein $R^1$ is $C_1$-$C_6$-alkyl or $C_2$-$C_6$-alkenyl or $C_2$-$C_6$-alkynyl.

22. The method claim 14, wherein $R^2$ is hydrogen, $C_1$-$C_6$-alkyl or C(=O)-($C_1$-$C_6$-alkoxy).

23. The method claim 14, wherein $R^2$ is hydrogen or methyl.

* * * * *